US012612389B2

(12) United States Patent
Kim et al.

(10) Patent No.: US 12,612,389 B2
(45) **Date of Patent: *Apr. 28, 2026**

(54) BENZOFURAN-BASED N-ACYLHYDRAZONE DERIVATIVE AND PHARMACEUTICAL COMPOSITION COMPRISING SAME

(71) Applicant: KOREA RESEARCH INSTITUTE OF BIOSCIENCE AND BIOTECHNOLOGY, Daejeon (KR)

(72) Inventors: Bo Yeon Kim, Daejeon (KR); Nak Kyun Soung, Daejeon (KR); Mija Ahn, Daejeon (KR); Ho Jin Han, Daejeon (KR); In Ja Ryoo, Daejeon (KR); Joonsung Hwang, Daejeon (KR)

(73) Assignee: Korea Research Institute of Bioscience and Biotechnology, Daejeon (KR)

(*) Notice: Subject to any disclaimer, the term of this patent is extended or adjusted under 35 U.S.C. 154(b) by 1006 days.

This patent is subject to a terminal disclaimer.

(21) Appl. No.: 17/627,547

(22) PCT Filed: Jul. 14, 2020

(86) PCT No.: PCT/KR2020/009262
§ 371 (c)(1),
(2) Date: Jan. 14, 2022

(87) PCT Pub. No.: WO2021/010731
PCT Pub. Date: Jan. 21, 2021

(65) Prior Publication Data
US 2022/0306612 A1 Sep. 29, 2022

(30) Foreign Application Priority Data
Jul. 15, 2019 (KR) ........................ 10-2019-0085045

(51) Int. Cl.
*C07D 405/12* (2006.01)
*A61P 35/04* (2006.01)

(52) U.S. Cl.
CPC ............ *C07D 405/12* (2013.01); *A61P 35/04* (2018.01)

(58) Field of Classification Search
CPC .................................................... C07D 405/12
See application file for complete search history.

(56) References Cited

U.S. PATENT DOCUMENTS

| | | | |
|---|---|---|---|
| 2002/0128292 A1 | 9/2002 | Cai et al. |
| 2014/0357682 A1 | 12/2014 | Lloyd et al. |

FOREIGN PATENT DOCUMENTS

| | | |
|---|---|---|
| KR | 1020140047354 | 1/2015 |
| WO | 02-102301 A2 | 12/2002 |
| WO | 2013/032907 A1 | 3/2013 |

OTHER PUBLICATIONS

International Search Report for corresponding PCT Application No. PCT/KR2020/009262 mailed Nov. 20, 2020.

(Continued)

*Primary Examiner* — Kortney L. Klinkel
*Assistant Examiner* — Jackson J Hernandez
(74) *Attorney, Agent, or Firm* — Wood, Phillips, Katz, Clark & Mortimer

(57) ABSTRACT

A benzofuran-based N-acylhydrazone derivative according to the present invention has an excellent anticancer effect while having low toxicity and excellent solubility, and thus a pharmaceutical composition comprising the derivative can be usefully used to prevent or treat a cell proliferative disorder including various cancers.

19 Claims, 15 Drawing Sheets

(56) References Cited

OTHER PUBLICATIONS

Chemical Abstract Compound. SIN express. RN: 2220348-97-8 (Apr. 27, 2018).
Chemical Abstract Compound. SIN express. RN: 444671-24-3 (Aug. 22, 2002).
Chemical Abstract Compound. SIN express. RN: 444292-03-9 (Aug. 20, 2002).
Office Action for corresponding Korean Application No. 10-2020-0086981 mailed May 12, 2022.
Yu, et al., "Discovery of novel inhibitors for human farnesyltransferase (hFTase) via structure-based virtual screening", Med. Chem. Commun., 2013, 4, 962-971.
Database Registry [Online], CAS Registry No. 2221847-46-5 (Apr. 30, 2018) 1.
Database Registry [Online], CAS Registry No. 2221523-47-1 (Apr. 29, 2018).
Database Registry [Online], CAS Registry No. 872528-89-7 (Jan. 24, 2006).
Database Registry [Online], CAS Registry No. 2218954-87-9 (Apr. 25, 2018).
Database Registry [Online], CAS Registry No. 931849-82-0 (Apr. 23, 2007).
Database Registry [Online], CAS Registry No. 890561-50-9 (Jul. 5, 2006).
Database Registry [Online], CAS Registry No. 890558-18-6 (Jul. 5, 2006).

BENZOFURAN-BASED N-ACYLHYDRAZONE DERIVATIVE AND PHARMACEUTICAL COMPOSITION COMPRISING SAME

TECHNICAL FIELD

The present invention relates to a benzofuran-based N-acylhydrazone derivative and a pharmaceutical composition comprising the same. More specifically, the present invention relates to a novel benzofuran-based N-acylhydrazone derivative that is used to prevent or treat a cell proliferative disease, and a pharmaceutical composition comprising the same.

BACKGROUND ART

Microtubules perform numerous cellular functions, such as cell migration, cell division, maintenance of the cytoskeleton, and intracellular transport. The major protein component of microtubules is tubulin. The rapid growth of cancer cells is highly dependent on tubulin polymerization/depolymerization, and thus tubulin has become an excellent target for the development of anticancer drugs. Intervention on the microtubule complex by inhibiting tubulin polymerization or blocking microtubule degradation increases the number of cells entrapped in metaphase, eventually leading to apoptosis. A method for inhibiting the function of microtubules using tubulin-targeting drugs is a validated approach for anticancer treatment (see Korean Patent Laid-Open Publication No. 2014-0128238).

Drugs targeting microtubules are divided into two groups of microtubule stabilizers and destabilizers depending on the mechanism of action. The microtubule stabilizers include taxane, paclitaxel, docetaxel, and the like, which inhibit microtubule depolymerization and enhance microtubule polymerization. Most microtubule stabilizers bind to the taxane binding site or to the overlapping site of β-tubulin. The second group, i.e., microtubule destabilizers includes colchicines, *vinca* alkaloids, and the like, which inhibit microtubule polymerization and bind mostly to the colchicine binding site or the *vinca* binding site. In addition, two classes of drugs that target microtubules act at lower concentrations than those that affect microtubule polymers.

However, most tubulin inhibitors are drug-resistant, which is a major obstacle in increasing the long-term response or survival of cancer patients. In addition, neurotoxicity as well as resistance problems are one of the main side effects of tubulin inhibitors derived from complex natural products, which affect the quality of life of cancer patients. Furthermore, low oral bioavailability is a restriction for comfortable oral administration. Therefore, in recent years, the development of novel tubulin inhibitors with low side effects, excellent oral bioavailability, and low resistance generation is urgently required.

DISCLOSURE

Technical Problem

The present inventors studied novel tubulin inhibitors, and found that a novel benzofuran-based N-acylhydrazone derivative synthesized through the N-acylhydrazone bond between benzofuran and indole group inhibited the polymerization of tubulin to induce apoptosis, effectively acted even on cancer cells exhibiting multidrug resistance, and had high stability and solubility in the body.

Therefore, an object of the present invention is to provide a novel tubulin inhibitor having excellent anticancer effect, low toxicity, and an excellent solubility. Another object of the present invention is to provide an anticancer composition comprising the novel tubulin inhibitor.

Technical Solution

In one general aspect, the present invention provides a compound represented by Chemical Formula 1 below, a stereoisomer or a pharmaceutically acceptable salt thereof:

Chemical Formula 1

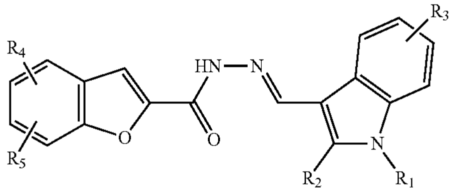

in Chemical Formula 1 above, $R_1$ is H, $C_{1-6}$alkyl, $C_{1-6}$alkoxycarbonyl$C_{1-3}$alkyl, or $C_{1-6}$alkoxy$C_{1-3}$alkyl;

$R_2$ is halogen, $C_{1-6}$alkyl or halo$C_{1-6}$alkyl;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$alkylcarbonylamino, provided that $R_4$ and $R_5$ are not H at the same time.

In another aspect, the present invention provides a pharmaceutical composition for preventing or treating a cell proliferative disease, comprising the compound represented by Chemical Formula 1, a stereoisomer or a pharmaceutically acceptable salt thereof as an active ingredient.

Advantageous Effects

The benzofuran-based N-acylhydrazone derivative represented by Chemical Formula 1 of the present invention, a stereoisomer or a pharmaceutically acceptable salt thereof inhibits the polymerization of tubulin in microtubules to induce apoptosis, effectively acts even on cancer cells exhibiting multidrug resistance, and has excellent cancer metastasis inhibitory activity. In addition, the compound of the present invention exhibits high stability and solubility in the body, thereby having excellent bioavailability. Thus, the pharmaceutical composition comprising the compound of the present invention may be usefully employed for the prevention or treatment of a cell proliferative disease including various cancers.

DESCRIPTION OF DRAWINGS

FIGS. 8A to 8F show the toxicity-testing and open field behavior test of the compound of Example 4, wherein FIG. 8A shows the schedule of the toxicity-testing and the appearance after the final injection of the compound of Example 4, FIG. 8B shows the mouse body weight measured during compound treatment, FIG. 8C is HIT map results showing mouse movements analyzed for 5 minutes in an open field experiment, FIG. 8D shows the time spent in the center zone, FIG. 8E shows a speed, and FIG. 8F shows the total moving distance.

BEST MODE

Figure 1:
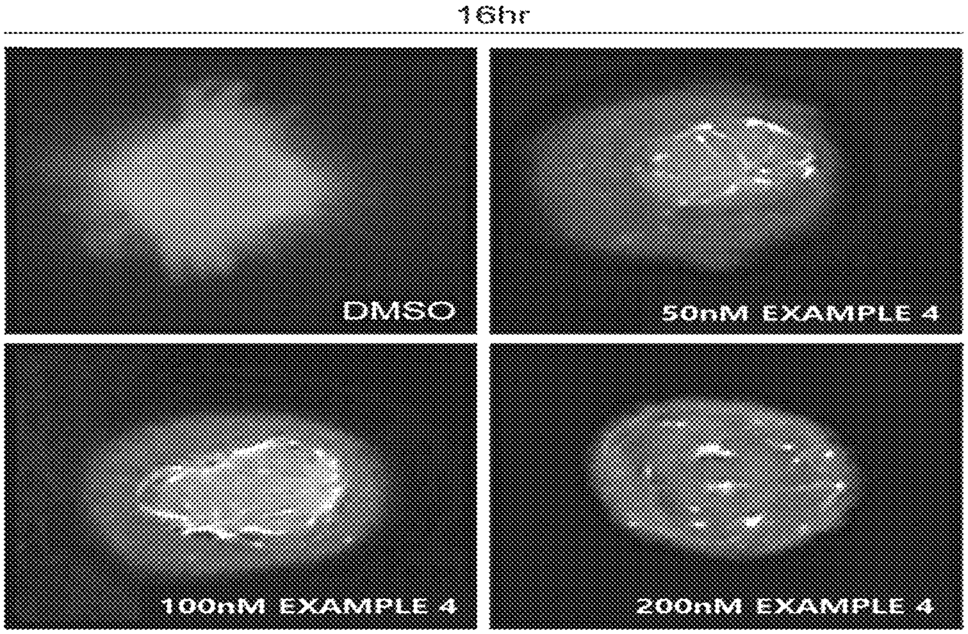
FIG. 1 is images of immunostaining showing the effect on the spindle and chromosome of cells in mitosis depending on the concentration of the Example compound according to the present invention.

In the present specification, the term "halogen" means F, Cl, Br or I unless otherwise specified.

The term "alkyl," unless otherwise specified, refers to a linear or branched saturated hydrocarbon moiety. For example, "$C_{1-6}$alkyl" refers to alkyl having a backbone comprising 1 to 6 carbon atoms. Specifically, $C_{1-6}$alkyl may include methyl, ethyl, n-propyl, i-propyl, n-butyl, i-butyl, t-butyl, n-pentyl, i-pentyl, t-pentyl, sec-pentyl, neopentyl, hexyl; and the like.

The term "alkoxy", unless otherwise specified, refers to a linear or branched alkyl-oxy moiety. For example, "$C_{1-6}$alkoxy" refers to alkyl-oxy having a backbone comprising 1 to 6 carbons. Specifically, $C_{1-6}$alkoxy may include methoxy, ethoxy, n-propoxy, i-propoxy, n-butoxy, i-butoxy, t-butoxy, n-pentoxy, i-pentoxy, t-pentoxy, sec-pentoxy, neopentoxy, hexyloxy, and the like.

The term "haloalkyl" or "haloalkoxy" means an alkyl or alkoxy substituted with one or more halogens. Specifically, haloalkyl or haloalkoxy may be alkyl or alkoxy in which one or more homogeneous or heterogeneous halogens are substituted.

The term "substitution" refers to the replacement of a hydrogen atom in a molecular structure with a substituent so as to form a compound that is chemically stable from this substitution without exceeding the valence on the designated atom. For example, "Group A is substituted with substituent B" may indicate that a hydrogen atom bonded to an atom such as carbon constituting the backbone of Group A is replaced with the substituent B, thereby forming a covalent bond between group A and substituent B.

The present invention provides a compound represented by Chemical Formula 1 below, a stereoisomer or a pharmaceutically acceptable salt thereof:

Chemical Formula 1

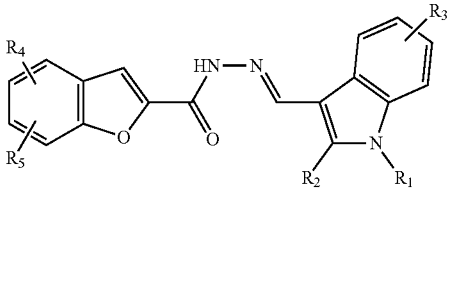

in Chemical Formula 1 above, $R_1$ is H, $C_{1-6}$alkyl, $C_{1-6}$alkoxycarbonyl$C_{1-3}$alkyl, or $C_{1-6}$alkoxy$C_{1-3}$alkyl;

$R_2$ is halogen, $C_{1-6}$alkyl or halo$C_{1-6}$alkyl;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$alkylcarbonylamino, provided that $R_4$ and $R_5$ are not H at the same time.

The $C_{1-6}$alkyl may include $C_{1-3}$alkyl, $C_{3-6}$alkyl, $C_{2-4}$alkyl, $C_{2-6}$alkyl, and the like.

In addition, the $C_{1-6}$alkoxy may include $C_{1-3}$alkoxy, $C_{3-6}$alkoxy, $C_{2-4}$alkoxy, $C_{2-6}$alkoxy, and the like.

Further, the halo$C_{1-6}$alkyl and the halo$C_{1-6}$alkoxy may each have 1 to 10, or 1 to 3, of the same or different halogens.

According to an embodiment, in Chemical Formula 1, $R_1$ is $-CH_3$, $-CH_2CO_2CH_2CH_3$, $-CH_2OCH_2CH_3$, $-CH_2CH_2OCH_2CH_3$ or $-CH_2CH_2OCH_3$.

According to another embodiment, in Chemical Formula 1, $R_2$ is Cl, Br, $-CH_3$, or $-CF_3$.

According to still another embodiment, in Chemical Formula 1, $R_3$ is H, F, Cl, $-CH_3$, $-OCH_3$, or $-OCF_3$.

According to another embodiment, in Chemical Formula 1, $R_4$ and $R_5$ are each independently H, Cl, $-CH_3$, $-OCH_3$, or $-NHCOCH_3$, provided that $R_4$ and $R_5$ are not H at the same time.

According to still another embodiment, in Chemical Formula 1, $R_1$ is H, $-CH_3$, $-CH_2CO_2CH_2CH_3$, $-CH_2OCH_2CH_3$, $-CH_2CH_2OCH_2CH_3$ or $-CH_2CH_2OCH_3$; $R_2$ is Cl, Br, $-CH_3$ or $-CF_3$; $R_3$ is H, F, Cl, $-CH_3$, $-OCH_3$, or $-OCF_3$; and $R_4$ and $R_5$ are each independently H, Cl, $-CH_3$, $-OCH_3$, or $-NHCOCH_3$, provided that $R_4$ and $R_5$ are not H at the same time.

Specific examples of the compound represented by Chemical Formula 1 are as follows:

1. (E)-N'-[(2-chloro-1H-indol-3-yl)methylene]-5-methylbenzofuran-2-carbohydrazide;
2. (E)-N'-[(2-chloro-1-methyl-1H-indol-3-yl)methylene]-5-methylbenzofuran-2-carbohydrazide;
3. Ethyl (E)-2-{2-chloro-3-[(2-(5-methylbenzofuran-2-carbonyl)hydrazinylidene)methyl]-1H-indol-1-yl}acetate;
4. (E)-N'-[(2-chloro-1-(2-ethoxyethyl)-1H-indol-3-yl]methylene}-5-methylbenzofuran-2-carbohydrazide;
5. (E)-N'-[(2-bromo-1-(2-ethoxyethyl)-1H-indol-3-yl]methylene}-5-methylbenzofuran-2-carbohydrazide;
6. (E)-N'-{[1-(2-ethoxyethyl)-2-(trifluoromethyl)-1H-indol-3-yl]methylene}-5-methylbenzofuran-2-carbohydrazide;
7. (E)-N'-[(2-chloro-1-(2-methoxyethyl)-1H-indol-3-yl]methylene}-5-methylbenzofuran-2-carbohydrazide;
8. (E)-N'-[(2-chloro-1-(2-ethoxyethyl)-5-methoxy-1H-indol-3-yl]methylene}-5-methylbenzofuran-2-carbohydrazide;
9. (E)-N'-[(2-chloro-1-(2-ethoxyethyl)-6-methoxy-1H-indol-3-yl]methylene}-5-methylbenzofuran-2-carbohydrazide;
10. (E)-N'-[(2-chloro-1-(2-ethoxyethyl)-5-fluoro-1H-indol-3-yl]methylene}-5-methylbenzofuran-2-carbohydrazide;
11. (E)-N'-{[2,5-dichloro-1-(2-ethoxyethyl)-1H-indol-3-yl]methylene}-5-methylbenzofuran-2-carbohydrazide;
12. (E)-N'-{[2-chloro-1-(2-ethoxyethyl)-5-(trifluoromethoxy)-1H-indol-3-yl]methylene}-5-methylbenzofuran-2-carbohydrazide;
13. (E)-N'-[(2-chloro-1-(2-ethoxyethyl)-5-methyl-1H-indol-3-yl]methylene}-5-methylbenzofuran-2-carbohydrazide;
14. (E)-N'-[(2-chloro-1-(2-ethoxyethyl)-1H-indol-3-yl]methylene}-5-methoxybenzofuran-2-carbohydrazide;

15. (E)-N'-[(2-chloro-1-(2-ethoxyethyl)-5-methoxy-1H-indol-3-yl]methylene}-5-methoybenzofuran-2-carbohydrazide;
16. (E)-5-chloro-N'-{[2-chloro-1-(2-ethoxyethyl)-1H-indol-3-yl]methylene}benzofuran-2-carbohydrazide;
17. (E)-N'-{[2-chloro-1-(2-ethoxyethyl)-1H-indol-3-yl]methylene}-4,7-dimethylbenzofuran-2-carbohydrazide;
18. (E)-N'-[(2-chloro-1-(2-ethoxyethyl)-1H-indol-3-yl]methylene}-4,6-dimethoxybenzofuran-2-carbohydrazide;
19. (E)-N'-{2-[2-((2-chloro-1-(2-ethoxyethyl)-1H-indol-3-yl)methylene]hydrazine-1-carbonyl}benzofuran-5-yl)acetamide; and
20. (E)-ethyl-2-(3-((2-(4,6-dimethoxybenzofuran-2-carbonyl)hydrazinylidene)methyl)-2-methyl-1H-indol-1-yl)acetate.

The present invention includes a pharmaceutically acceptable salt of the compound represented by Chemical Formula 1 above.

The pharmaceutically acceptable salt should have low toxicity to humans and should not have any negative effect on the biological activity and physicochemical properties of the parent compound.

For example, the pharmaceutically acceptable salt may be an acid addition salt formed by a pharmaceutically acceptable free acid.

The free acid may be an inorganic acid or an organic acid, wherein the inorganic acid may be hydrochloric acid, sulfuric acid, nitric acid, phosphoric acid, perchloric acid, hydrobromic acid, and the like, and the organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like.

The acid addition salt may be prepared by a conventional method, for example, by dissolving the compound of Chemical Formula 1 in an excess of aqueous acid solution, and precipitating the salt using a water-miscible organic solvent such as methanol, ethanol, acetone or acetonitrile.

In addition, the pharmaceutically acceptable salt may be an alkali metal salt (such as a sodium salt, and the like) or an alkaline earth metal salt (such as a potassium salt, and the like).

The alkali metal salt or alkaline earth metal salt may be obtained by, for example, dissolving the compound of Chemical Formula 1 in an excess of alkali metal hydroxide or alkaline earth metal hydroxide solution, and filtering the undissolved compound salt, followed by evaporating and drying the filtrate.

In addition, the compounds of the present invention may have chiral carbon centers and may therefore exist in the form of R or S isomers, racemic compounds, individual enantiomers or mixtures, individual diastereomers or mixtures, wherein all these stereoisomers and mixtures thereof may be included within the scope of the present invention.

Further, the compound of the present invention may include hydrates and solvates of the compound of Chemical Formula 1 above. The hydrates and solvates may be prepared using known methods, and preferably nontoxic and water-soluble. In particular, preferably, the hydrate and the solvate may be prepared by binding 1 to 5 molecules of water and an alcoholic solvent (particularly, ethanol, or the like), respectively.

The compound of the present invention, that is, the compound of Chemical Formula 1, a stereoisomer or a pharmaceutically acceptable salt thereof, inhibits the polymerization of tubulin in microtubules to induce apoptosis, effectively acts even on cancer cells exhibiting multidrug resistance, and has excellent cancer metastasis inhibitory activity. In addition, the compound of the present invention exhibits high stability and solubility in the body, thereby having excellent bioavailability.

Accordingly, the compound of the present invention or a pharmaceutical composition comprising the same may be used for the prevention or treatment of a cell proliferative disease. In addition, the compounds of the present invention may be employed to depolymerize microtubules. Specifically, the compounds of the present invention may be used to inhibit tubulin, more specifically, to inhibit polymerization of tubulin. In addition, the compound of the present invention may act on the colchicine binding site of tubulin, and may induce apoptosis by arresting the cell cycle in either G2 or M phase. Further, the compound of the present invention may act on cancer cells exhibiting multidrug resistance.

For example, the compound of the present invention or a pharmaceutical composition comprising the same may be used as a tubulin inhibitor or an anticancer agent.

Accordingly, the present invention provides the use of the compound of Chemical Formula 1, a stereoisomer or a pharmaceutically acceptable salt thereof, for preventing or treating a cell proliferative disease.

Further, the present invention provides the use of the compound of Chemical Formula 1, a stereoisomer or a pharmaceutically acceptable salt thereof, for inhibiting polymerization of tubulin.

In addition, the present invention provides the use of the compound of Chemical Formula 1, a stereoisomer or a pharmaceutically acceptable salt thereof, for the preparation of a medicament for preventing or treating a cell proliferative disease.

Further, the present invention provides the use of the compound of Chemical Formula 1, a stereoisomer or a pharmaceutically acceptable salt thereof, for the preparation of a medicament for inhibiting polymerization of tubulin.

In addition, the present invention provides a method for inhibiting polymerization of tubulin, comprising administering to a subject in need thereof the compound of Chemical Formula 1, a stereoisomer or a pharmaceutically acceptable salt thereof.

Further, the present invention provides a method for preventing or treating a cell proliferative disease, comprising administering to a subject in need thereof the compound of Chemical Formula 1, a stereoisomer or a pharmaceutically acceptable salt thereof.

Herein, "prevention" means any action that inhibits or delays the occurrence, spread, and recurrence of the disease by administration of the compound, and "treatment" refers to any action in which the symptoms of the disease are ameliorated or beneficially changed by administration of the compound.

Herein, the term "subject in need" refers to all animals such as monkeys, cows, horses, sheep, pigs, chickens, turkeys, quails, cats, dogs, mice, rats, rabbits, guinea pigs, and the like, including humans (patients) who have or are likely to develop the cell proliferative disease, and may specifically refer to mammals. In addition, the subject in need may refer to a biological sample.

In addition, "administration" means providing a predetermined substance to a subject in need thereof by any suitable method, and the administration route of the compound of the present invention may be achieved through any general route as long as it is able to reach the target tissue.

Further, the present invention provides a pharmaceutical composition comprising the compound of Chemical Formula 1, a stereoisomer or a pharmaceutically acceptable salt thereof as an active ingredient.

In addition, the present invention provides a pharmaceutical composition for inhibiting polymerization of tubulin, comprising the compound of Chemical Formula 1, a stereoisomer or a pharmaceutically acceptable salt thereof, as an active ingredient.

Further, the present invention provides a pharmaceutical composition for preventing or treating a cell proliferative disease, comprising the compound of Chemical Formula 1, a stereoisomer or a pharmaceutically acceptable salt thereof as an active ingredient.

The cell proliferative disease may be cancer. As used herein, "cancer" refers to the abnormal growth of cells that tend to proliferate or metastasize in an uncontrolled manner.

Specifically, the cancer may be a solid cancer, a blood cancer, or a metastatic cancer. More specifically, the cancer may be rectal cancer, breast cancer, lung cancer, stomach cancer, liver cancer, leukemia, glioma, skin cancer, cervical cancer, or metastases derived therefrom.

Accordingly, the pharmaceutical composition comprising the compound of the present invention may be used as a therapeutic agent for various cancers exemplified above or as an inhibitor of cancer metastasis.

Further, the present invention provides a pharmaceutical composition comprising the compound of Chemical Formula 1, a stereoisomer or a pharmaceutically acceptable salt thereof, and a pharmaceutically acceptable additive.

The pharmaceutical composition of the present invention may contain, as an active ingredient, the compound of Chemical Formula 1, a stereoisomer or a pharmaceutically acceptable salt thereof, in an amount of 0.1% to 90% by weight, specifically 0.1% by weight to 75% by weight, and more specifically 1 wt % to 50 wt %, based on the total weight of the composition.

The pharmaceutical composition of the present invention may include conventional and non-toxic pharmaceutically acceptable additives according to conventional methods. For example, the pharmaceutical composition may further include a pharmaceutically acceptable carrier, diluent or excipient.

Examples of additives used in the composition of the present invention may include sweeteners, binders, solvents, dissolution aids, wetting agents, emulsifiers, isotonic agents, absorbents, disintegrants, antioxidants, preservatives, lubricants, fillers, flavoring agents, and the like. For example, the additive may include lactose, dextrose, sucrose, mannitol, sorbitol, cellulose, glycine, silica, talc, stearic acid, stearin, magnesium stearate, magnesium aluminosilicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, and the like.

The composition of the present invention may be mixed in the form of various formulations for oral administration (for example, tablets, pills, powders, capsules, syrups or emulsions) or for parenteral administration (for example, intramuscular, intravenous or subcutaneous injection).

Preferably, the composition of the present invention may be mixed as a formulation for oral administration, wherein additives to be used may include cellulose, calcium silicate, corn starch, lactose, sucrose, dextrose, calcium phosphate, stearic acid, magnesium stearate, calcium stearate, gelatin, talc, surfactants, suspensions, emulsifiers, diluents, and the like.

Specifically, solid formulations for oral administration may include tablets, pills, powders, granules, capsules, and the like, and the solid formulations may be prepared by mixing, at least one excipient such as starch, calcium carbonate, sucrose, lactose, gelatin, and the like, in the composition. Further, in addition to simple excipients, lubricants such as magnesium stearate and talc may be used.

In addition, examples of liquid formulations for oral administration may include suspensions, emulsions, syrups, and the like, and various excipients, for example, wetting agents, sweeteners, flavorants, preservatives, and the like, in addition to the commonly used simple diluents such as water and liquid paraffin.

Further, formulations for parenteral administration may include sterilized aqueous solution, non-aqueous solvents, suspensions, emulsions, lyophilized formulations and suppositories. The non-aqueous solvents and suspensions may include propylene glycol, polyethylene glycol, vegetable oils such as olive oil, and injectable esters such as ethyl oleate. For the suppository, witepsol, macrogol, Tween 61, cacao butter, laurin butter, glycerogelatin, and the like, may be used as a base. Meanwhile, the injection may include conventional additives such as solubilizers, isotonic agents, suspending agents, emulsifiers, stabilizers, and preservatives, and the like.

The compound or composition of the present invention may be administered to a patient in a therapeutically effective amount or a pharmaceutically effective amount.

Herein, "therapeutically effective amount" or "pharmaceutically effective amount" refers to an amount of a compound or composition effective to prevent or treat a target disease, which is an amount sufficient to treat a disease with a reasonable benefit/risk ratio applicable to medical treatment and that does not cause side effects. The level of the effective amount may be determined according to factors including the patient's health condition, type and severity of disease, the activity of drug, the patient's sensitivity to drug, the method of administration, administration time, administration route and excretion rate, duration of treatment, and drugs used in combination or at the same time, and other factors well known in the medical field.

The compound or composition of the present invention may be administered as individual therapeutic agents or in combination with other therapeutic agents, may be administered sequentially or simultaneously with conventional therapeutic agents, or may be administered in a single dose or in multiple doses. It is important to administer the compound or composition of the present invention in an amount that is able to achieve the maximum effect with the minimum amount without side effects in consideration of all of the above factors, which may be readily determined by those skilled in the art.

Specifically, the effective amount of the compound in the composition of the present invention may vary depending on the age, sex, and weight of the patient, and in general, 0.1 mg to 100 mg, or 0.5 mg to 10 mg per 1 kg of body weight may be administered daily or every other day, or divided into 2 or 3 times a day. However, since the effective amount may be increased or decreased depending on the route of administration, the severity of disease, sex, weight, age, and the like, the scope of the present invention is not limited thereto.

Preferably, the compound or composition of the present invention may be administered for tumor therapy in combination with chemotherapy, radiation therapy, immunotherapy, hormone therapy, bone marrow transplantation, stem cell replacement therapy, other biological therapy, surgical intervention or a combination thereof. For example, the compound or composition of the present invention may be used as an adjuvant therapy in combination with other long-term treatment strategies, or may be used to maintain the patient's condition after tumor regression or chemopreventive therapy in critically ill patients.

Preferably, the pharmaceutical composition of the present invention may further contain one or more active ingredients, wherein examples of the active ingredient to be further contained may include, but are not limited to, anti-proliferative compounds, such as aromatase inhibitors, anti-estrogens, topoisomerase I inhibitors, topoisomerase II inhibitors, microtubule active compounds, alkylating compounds, histone deacetylase inhibitors, compounds that induce cell differentiation processes, cyclooxygenase inhibitors, MMP inhibitors, mTOR inhibitors, anti-neoplastic anti-metabolites, platin compounds, compounds that target/reduce protein or lipid kinase activity, anti-angiogenic compounds, compounds that target, reduce or inhibit the activity of proteins or lipid phosphatases, gonadorelin agonists, anti-androgens, methionine aminopeptidase inhibitors, bisphosphonates, biological response modifiers, anti-proliferative antibodies, heparanase inhibitors, inhibitors of the Ras tumorigenic isoform, telomerase inhibitors, proteasome inhibitors, compounds used in the treatment of hematologic malignancies, compounds that target, reduce or inhibit the activity of Flt-3, Hsp90 inhibitors, kinesin spindle protein inhibitors, MEK inhibitors, leucovorin, EDG binding agents, anti-leukemia compounds, ribonucleotide reductase inhibitors, S-adenosylmethionine decarboxylase inhibitors, hemostatic steroids, corticosteroids, other chemotherapeutic compounds, and photosensitizing compounds.

MODES FOR CARRYING OUT THE INVENTION

Hereinafter, the present invention will be described in more detail by way of Examples. However, the following Examples are merely provided for easier understanding of the present invention, and the contents of the present invention are not limited by these Examples.

Abbreviations used in the Examples below are defined as follow:

| |
|---|
| EA: ethyl acetate, |
| EtOH: ethanol, |
| Et: ethyl, |
| DMF: dimethylformamide, |
| n-Hex: n-hexane, |
| PrOH: propanol, |
| DMSO: dimethyl sulfoxide. |

Preparation of Aromatic Substituted benzofuran-2-Carbohydrazide Derivative

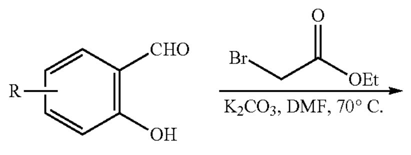

-continued

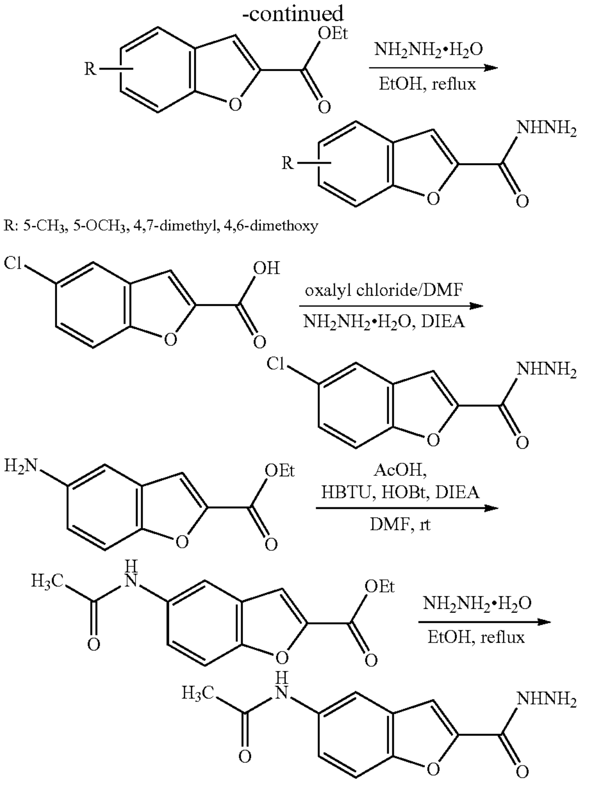

Preparation Example 1: Ethyl 5-methylbenzofuran-2-carboxylate

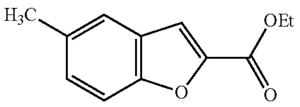

5-Methylsalicylaldehyde (1.40 g, 10.3 mmol) was dissolved in DMF (30 mL), then $Ce_2SO_4$ (10.07 g, 30.9 mmol) and ethyl bromoacetate (1.38 mL, 12.4 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=10:1) to obtain 1.28 g of the title compound (yield 61%, colorless liquid).

$^1H$ NMR (400 MHz, $CDCl_3$): δ 7.49-7.46 (m, 3H), 7.26 (m, 1H), 4.45 (q, J=7.2 Hz, 2H), 2.46 (s, 3H), 1.44 (t, J=7.2 Hz, 3H); $^{13}C$ NMR (100 MHz, $CDCl_3$): δ 159.85, 154.37, 145.92, 133.51, 129.27, 127.22, 122.45, 113.74, 112.02, 61.61, 21.45, 14.51; mp 38-39° C.

Preparation Example 2: 5-Methylbenzofuran-2-carbohydrazide

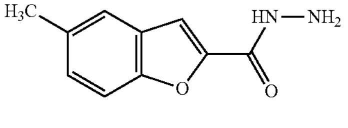

Ethyl 5-methylbenzofuran-2-carboxylate (2.04 g, 10.0 mmol) obtained in Preparation Example 1 was dissolved in EtOH (30 mL), then hydrazine monohydrate (1.50 g, 30.0 mmol) was added thereto, and refluxed for 24 hours. The reaction solution was distilled under reduced pressure to obtain a solid, and the obtained solid was washed with water and dried to obtain 1.72 g of the title compound (yield 90%, white solid).

$^1$H NMR (400 MHz, DMSO-$d_6$): δ 9.97 (s, 1H), 7.52-7.49 (m, 2H), 7.43 (s, 1H), 7.25 (dd, J=8.4, 1.6 Hz, 1H), 4.55 (br s, 2H), 2.40 (s, 3H); $^{13}$C NMR (100 MHz, DMSO-$d_6$): δ 157.92, 152.64, 148.48, 132.68, 127.84, 127.11, 122.04, 111.27, 108.47, 20.81; MS (MALDI-TOF) m/z 213 $[M+Na]^+$; mp 159° C.

Preparation Example 3: Ethyl 5-methoxybenzofuran-2-carboxylate

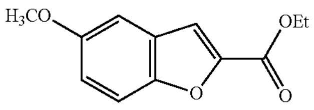 [SMILES: CCOC(=O)c1cc2cc(OC)ccc2o1]

2-Hydroxy-5-methoxybenzaldehyde (1.25 mL, 10.0 mmol) was dissolved in DMF (30 mL), then $K_2CO_3$ (6.91 g, 50.0 mmol) and ethyl bromoacetate (1.33 mL, 12.0 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=3:1) to obtain 1.1 g of the title compound (yield 50%, white solid).

$^1$H NMR (400 MHz, $CDCl_3$): δ 7.50-7.47 (m, 2H), 7.08-7.05 (m, 2H), 4.45 (q, 2H, J=7.2 Hz), 3.86 (s, 3H), 1.44 (t, 3H, J=7.2 Hz); mp 53° C.

Preparation Example 4: 5-Methoxybenzofuran-2-carbohydrazide

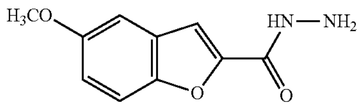

Ethyl 5-methoxybenzofuran-2-carboxylate (1.03 g, 4.68 mmol) obtained in Preparation Example 3 was dissolved in EtOH (30 mL), then hydrazine monohydrate (702.8 mg, 14.04 mmol) was added thereto, and refluxed for 24 hours. The reaction solution was distilled under reduced pressure to obtain a solid, and the obtained solid was washed with $CH_2Cl_2$ and dried to obtain 918 mg of the title compound (yield 95%, white solid).

$^1$H NMR (400 MHz, DMSO-$d_6$): δ 9.98 (s, 1H), 7.53 (d, 1H, J=9.0 Hz), 7.44 (s, 1H), 7.25 (d, 1H, J=2.7 Hz), 7.02 (dd, 1H, J=9.0, 2.7 Hz), 4.55 (br s, 2H), 3.79 (s, 3H); $^{13}$C NMR (100 MHz, DMSO-$d_6$): δ 157.85, 155.97, 149.10, 149.03, 127.65, 115.80, 112.34, 108.34, 104.09, 55.58; MS (MALDI-TOF): m/z 229.0 $[M+Na]^+$, 245 $[M+K]^+$; mp 163-164° C.

Preparation Example 5: 5-Chlorobenzofuran-2-carbohydrazide

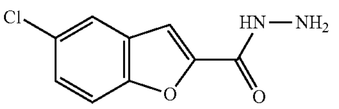 [SMILES: NNC(=O)c1cc2cc(Cl)ccc2o1]

Oxalic chloride (257.2 μL, 3.0 mmol) and DMF (50 μL) were added to $CH_2Cl_2$ (5 mL) at 0° C., stirred for 5 minutes, and a mixed solution of 5-chlorobenzofuran-2-carboxylic acid (393.2 mg, 2.0 mmol) in $CH_2Cl_2$/DMF (5 mL, 4:1) was then added thereto, and stirred at room temperature for 2 hours. The reaction solution was distilled under reduced pressure, $CH_2Cl_2$ (5 mL) was added again, and a solution of hydrazine monohydrate (120.1 mg, 2.4 mmol) in $CH_2Cl_2$ (5 mL) and N,N-diisopropylethylamine (DIEA, 1.74 mL, 10 mmol) were added at 0° C. and stirred at room temperature for 15 hours. The reaction solution was diluted with water and extracted with EA. The organic layer was dried over $Na_2SO_4$, filtered, and distilled under reduced pressure. The residue was washed with $CH_2Cl_2$ and dried to obtain 295 mg of the title compound (yield 70%, pale yellow solid).

$^1$H NMR (400 MHz, DMSO-$d_6$): δ 10.10 (s, 1H), 7.86 (d, J=2.4 Hz, 1H), 7.68 (d, J=9.2 Hz, 1H), 7.48 (s, 1H), 7.46 (dd, J=9.2, 2.4 Hz, 1H), 4.59 (br s, 2H); $^{13}$C NMR (100 MHz, DMSO-$d_6$): δ 157.41, 152.66, 149.79, 128.65, 127.99, 126.56, 122.02, 113.44, 108.25; MS (MALDI-TOF): m/z 233 $[M+Na]^+$; mp 174-175° C.

Preparation Example 6: Ethyl 4,7-dimethylbenzofuran-2-carboxylate

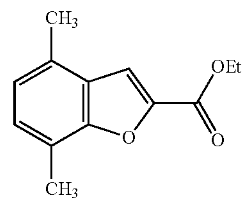 [SMILES: CCOC(=O)c1cc2c(C)ccc(C)c2o1]

3,6-dimethylsalicylaldehyde (450.5 mg, 3.0 mmol) was dissolved in DMF (30 mL), then $Ce_2SO_4$ (2.93 g, 9.0 mmol) and ethyl bromoacetate (399.2 μL, 3.60 mmol) were added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=20:1) to obtain 360 mg of the title compound (yield 55%, colorless liquid).

$^1$H NMR (400 MHz, $CDCl_{13}$) δ 7.56 (s, 1H), 7.14 (d, J=7.2 Hz, 1H), 6.99 (d, J=7.2 Hz, 1H), 4.45 (q, J=7.2 Hz, 2H), 2.55 (s, 3H), 2.52 (s, 3H), 1.44 (t, J=7.2 Hz, 3H); $^{13}$C NMR (100 MHz, $CDCl_3$) δ 159.91, 154.90, 145.08, 130.19, 128.30, 126.63, 123.90, 119.85, 113.01, 61.43, 18.29, 15.00, 14.46

Preparation Example 7: 4,7-Dimethylbenzofuran-2-carbohydrazide

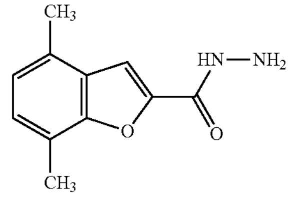

Ethyl 4,7-dimethylbenzofuran-2-carboxylate (290.3 mg, 1.33 mmol) obtained in Preparation Example 6 was dissolved in EtOH (30 mL), then hydrazine monohydrate (199.7 mg, 3.99 mmol) was added thereto, and refluxed for 24 hours. The reaction solution was distilled under reduced pressure to obtain a solid, and the obtained solid was washed with water and dried to obtain 236 mg of the title compound (yield 87%, white solid).

$^1$H NMR (400 MHz, DMSO-$d_6$): δ 9.97 (s, 1H), 7.55 (s, 1H), 7.13 (d, J=7.4 Hz, 1H), 7.00 (d, J=7.4 Hz, 1H), 4.59 (br s, 2H), 2.46 (s, 6H, $CH_3$×2); $^{13}$C NMR (100 MHz, DMSO-$d_6$): δ 158.05, 153.07, 147.65, 129.34, 127.07, 126.47, 123.64, 118.65, 107.94, 17.86, 14.38; MS (MALDI-TOF): m/z 227 [M+Na]$^+$; mp 187° C.

Preparation Example 8: Ethyl 4,6-dimethoxybenzofuran-2-carboxylate

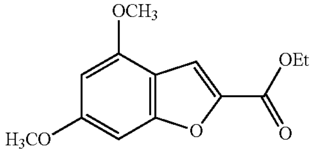

4,6-Dimethoxysalicylaldehyde (499.2 mg, 2.74 mmol) was dissolved in DMF (10 mL), and $K_2CO_3$ (1.89 g, 13.7 mmol) and ethyl bromoacetate (364.8 μL, 3.29 mmol) were then added thereto, and reacted at 70° C. for 15 hours. The reaction solution was diluted with water and extracted with EA. The organic layer was dried over $MgSO_4$, filtered, and distilled under reduced pressure. The residue was separated by column chromatography (n-Hex:EA=20:1) to obtain 460 mg of the title compound (yield 67%, white solid).

$^1$H NMR (400 MHz, $CDCl_3$): δ 7.54 (m, 1H), 6.67 (m, 1H), 6.35 (d, J=1.9 Hz, 1H), 4.41 (q, J=7.2 Hz, 2H), 3.90 (s, 3H), 3.857 (s, 3H), 1.40 (t, J=7.2 Hz, 3H); (MALDI-TOF) m/z 251 [M+H]$^+$; mp 98° C.

Preparation Example 9: 4,6-Dimethoxybenzofuran-2-carbohydrazide

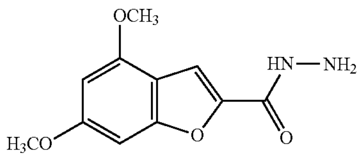

Ethyl 4,6-dimethoxybenzofuran-2-carboxylate (450.5 mg, 1.80 mmol) obtained in Preparation Example 8 was dissolved in EtOH (20 mL), and hydrazine monohydrate (450.5 mg, 9.0 mmol) was then added thereto, and refluxed for 6 hours. The reaction solution was poured into cold water to obtain a solid, and the resulting solid was filtered, washed with ethyl ether, and dried to obtain 360 mg of the title compound (yield 85%, white solid).

$^1$H NMR (400 MHz, DMSO-$d_6$): δ 9.78 (s, 1H), 7.40 (d, J=0.8 Hz, 1H), 6.79 (m, 1H), 6.45 (d, J=2.0 Hz, 1H), 4.49 (br s, 2H), 3.88 (s, 3H), 3.82 (s, 3H); $^{13}$C NMR (100 MHz, DMSO-$d_6$): δ 160.64, 158.10, 156.16, 153.94, 146.15, 110.83, 105.97, 94.98, 88.36, 55.79, 55.71; MS (MALDI-TOF): m/z 259 [M+Na]$^+$; mp 194° C.

Preparation Example 10: Ethyl 5-acetamidobenzofuran-2-carboxylate

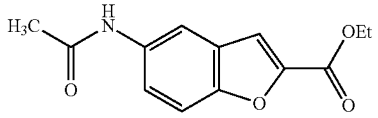 [SMILES: CCOC(=O)c1cc2cc(NC(C)=O)ccc2o1]

Ethyl 5-aminobenzofuran-2-carboxylate (205.2 mg, 1.0 mmol) was dissolved in DMF (3 mL), and (2-(1H-benzotriazol-1-yl)-1,1,3,3-tetramethyluronium hexafluorophosphate (HBTU, 417.2 mg, 1.1 mmol), hydroxybenzotriazole (HOBt, 148.6 mg, 1.1 mmol), N,N-diisopropylethylamine (DIEA, 209.0 μL, 1.2 mmol), and acetic acid (63.0 μL, 1.1 mmol) were then added thereto, and reacted at room temperature for 15 hours. The reaction solution was diluted with water and extracted with EA. The organic layer was dried over $MgSO_4$, filtered, and distilled under reduced pressure. The residue was separated by column chromatography ($CH_2Cl_2$:EA=3:1) to obtain 162 mg of the title compound (yield 66%, white solid).

$^1$H NMR (400 MHz, DMSO-$d_6$): δ 10.06 (s, 1H), 8.19 (d, J=2.0 Hz, 1H), 7.75 (d, J=0.8 Hz, 1H), 7.65 (d, J=8.8 Hz, 1H), 7.53 (dd, J=8.8, 2.0 Hz, 1H), 4.35 (q, J=7.2 Hz, 2H), 2.07 (s, 3H), 1.33 (t, J=7.2 Hz, 3H); $^{13}$C NMR (100 MHz, DMSO-$d_6$) δ 168.76, 159.66, 152.77, 146.68, 134.10, 127.54, 121.15, 114.18, 114.07, 112.66, 61.79, 24.64, 14.49; mp 181-182° C.

Preparation Example 11: N-(2-(hydrazinecarbonyl)benzofuran-5-yl)acetamide

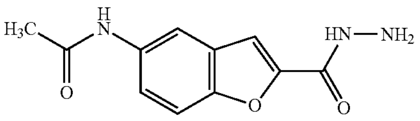 [SMILES: CC(=O)Nc1ccc2oc(C(=O)NN)cc2c1]

Ethyl 5-acetamidobenzofuran-2-carboxylate (514.3 mg, 2.08 mmol) obtained in Preparation Example 10 was dissolved in 1-PrOH (20 mL), then hydrazine monohydrate (312.4 mg, 6.24 mmol) was added thereto, and refluxed for 24 hours. The reaction solution was distilled under reduced pressure to obtain a solid, and the obtained solid was washed with a mixed solvent of n-Hex and $CH_2Cl_2$ (1:1) and dried to obtain 392 mg of the title compound (yield 81%, [Yong-Yang1]white solid)

$^1H$ NMR (400 MHz, DMSO-$d_6$): δ 10.02 (s, 1H), 9.97 (s, 1H), 8.10 (d, J=1.6 Hz, 1H), 7.55 (d, J=9.2 Hz, 1H), 7.48-7.45 (m, 2H), 4.55 (br s, 2H), 2.06 (s, 3H); $^{13}C$ NMR (100 MHz, DMSO-$d_6$) δ 168.23, 157.84, 150.42, 148.93, 135.37, 127.10, 119.12, 111.98, 111.72, 109.06, 23.96; MS (MALDI-TOF) m/z 256 $[M+Na]^+$, 272 $[M+K]^+$; mp 219-220° C.

Preparation of Aromatic/N-Substituted indol-3-Carboxaldehyde Derivative

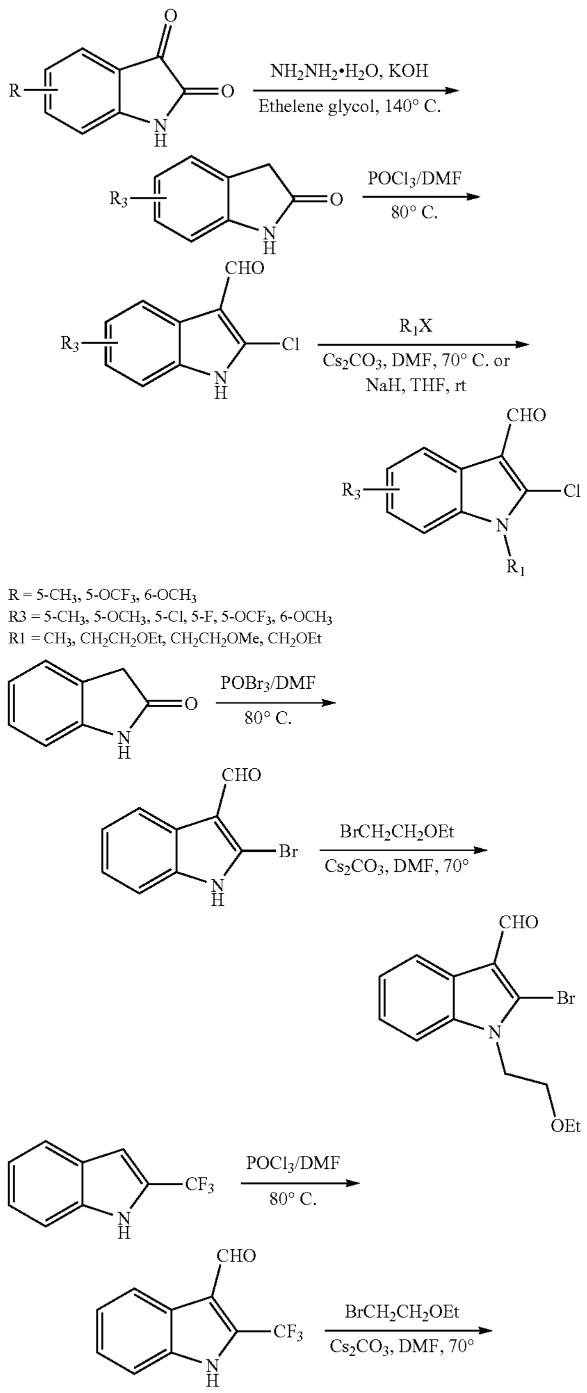

-continued

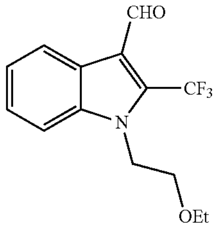

Preparation Example 12: 2-Chloro-1-methyl-1H-indol-3-carboxaldehyde

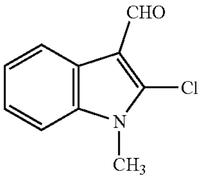

THF (20 μmL) was added to 2-chloro-1H-indol-3-carboxaldehyde (359.2 mg, 2.0 mmol) and NaH (120.0 mg, 3.0 mmol, 60% in oil) at 0° C. and stirred for 5 minutes. Then, iodomethane (149.4 μL, 2.4 mmol) was added and stirred at room temperature for 5 hours. The reaction solution was diluted with water and extracted with EA. The organic layer was dried over $MgSO_4$, filtered, and distilled under reduced pressure. The residue was separated by column chromatography ($CH_2Cl_2$:EA=15:1) to obtain 330 mg of the title compound (yield 85%, white solid).

$^1H$ NMR (400 MHz, $CDCl_3$): δ 10.13 (s, 1H), 8.30 (m, 1H), 7.36-7.32 (m, 3H), 3.82 (s, 3H); $^{13}C$ NMR (100 MHz, DMSO-$d_6$): 184.07, 136.99, 136.13, 124.44, 124.20, 123.69, 121.43, 113.02, 109.64, 30.28; MS (MALDI-TOF): m/z 194 $[M+H]^+$; mp 97-98° C.

Preparation Example 13: Ethyl 2-(2-chloro-3-formyl-1H-indol-1-yl)acetate

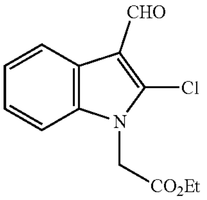 [SMILES: CCOC(=O)Cn1c(Cl)c(C=O)c2ccccc21]

THF (10 μmL) was added to 2-chloro-1H-indol-3-carboxaldehyde (200.0 mg, 1.11 mmol) and NaH (66.8 mg, 1.67 mmol, 60% in oil) at 0° C. and stirred for 5 minutes. Then, ethyl bromoacetate (147.5 μL, 1.33 mmol) was added and stirred at room temperature for 7 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 244 mg of the title compound (yield 83%, white solid).

$^1H$ NMR (400 MHz, $CDCl_3$): δ 10.16 (s, 1H), 8.32 (m, 1H), 7.36-7.32 (m, 2H), 7.23 (m, 1H), 4.95 (s, 2H), 4.26 (q,

J=7.2 Hz, 2H), 1.28 (t, J=7.2 Hz, 3H); $^{13}C$ NMR (100 MHz, $CDCl_3$): δ 184.09, 166.47, 136.48, 135.70, 124.45, 124.34, 123.78, 121.55, 113.62, 109.03, 62.36, 44.81, 14.05; MS (MALDI-TOF): m/z 266 $[M+H]^+$; mp 110° C.

Preparation Example 14: 2-Chloro-1-(2-ethoxyethyl)-1H-indol-3-carboxaldehyde

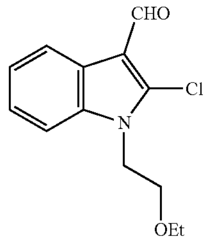 [SMILES: CCOCCn1c(Cl)c(C=O)c2ccccc21]

2-chloro-1H-indol-3-carboxaldehyde (2.69 g, 15.0 mmol) was dissolved in DMF (50 mL), then 2-bromoethyl ethyl ether (2.01 mL, 18.0 mmol) and $Cs_2CO_3$ (14.7 g, 45.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=4:2:1) to obtain 2.95 g of the title compound (yield 78%, pale yellow solid).

$^1H$ NMR (400 MHz, $CDCl_3$): δ 10.14 (s, 1H), 8.30 (m, 1H), 7.41 (m, 1H), 7.34-7.30 (m, 2H), 4.42 (t, J=5.6 Hz, 2H), 3.76 (t, J=5.6 Hz, 2H), 3.44 (q, J=7.2 Hz, 2H), 1.12 (t, J=7.2 Hz, 3H); $^{13}C$ NMR (100 MHz, $CDCl_3$): δ 184.09, 136.58, 135.80, 124.41, 123.95, 123.43, 121.24, 113.08, 110.04, 68.13, 66.91, 43.97, 14.97; MS (MALDI-TOF): m/z 252 $[M+H]^+$; mp 52° C.

Preparation Example 15: 2-Chloro-1-(2-methoxyethyl)-1H-indol-3-carboxaldehyde

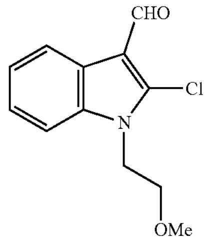 [SMILES: COCCn1c(Cl)c(C=O)c2ccccc21]

2-Chloro-1H-indol-3-carboxaldehyde (538.8 mg, 3.0 mmol) was dissolved in DMF (10 mL), then 2-bromoethyl methyl ether (422.6 μL, 4.5 mmol) and $Cs_2CO_3$ (2.93 g, 9.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex:EA=2:1) to obtain 468 mg of the title compound (yield 66%, pale yellow solid).

$^1H$ NMR (400 MHz, $CDCl_3$): δ 10.14 (s, 1H), 8.30 (m, 1H), 7.42-7.31 (m, 3H), 4.43 (t, J=5.7 Hz, 2H), 3.74 (t, J=5.7 Hz, 2H), 3.32 (s, 3H); $^{13}C$ NMR (100 MHz, $CDCl_3$): δ 184.27, 136.79, 135.97, 124.56, 124.21, 123.64, 121.44, 113.25, 110.17, 70.49, 59.35, 44.00; MS (MALDI-TOF): m/z 238 $[M+H]^+$, 260 $[M+Na]^+$; mp 66-67° C.

Preparation Example 16: 5-Methyloxyindole

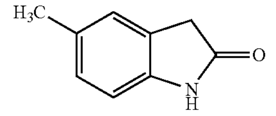

Ethylene glycol (10 mL) was added to 5-methylisatin (1.50 g, 9.31 mmol), then KOH (522.4 mg, 9.31 mmol) and hydrazine monohydrate (1.40 g, 27.9 mmol) were added thereto, and heated at 140° C. for 4 hours. The reaction solution was cooled, acidified with 1N HCl, and extracted with EA. The organic layer was distilled under reduced pressure, and the residue was separated by column chromatography (n-Hex:EA=3:2) to obtain 1.0 g of the title compound (yield 73%, light brown solid).

$^1H$ NMR (400 MHz, DMSO-$d_6$): δ 10.23 (br s, 1H), 7.01 (s, 1H), 6.96 (d, J=7.9 Hz, 1H), 6.69 (d, J=7.9 Hz, 1H), 3.41 (s, 2H), 2.23 (s, 3H)

Preparation Example 17: 2-Chloro-5-methyl-1H-indol-3-carboxaldehyde

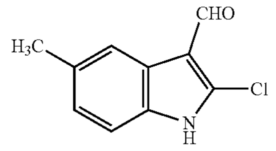

$POCl_3$ (2.65 mL, 28.9 mmol) was added to DMF (10 mL) at 0° C., and stirred for 10 minutes. Then, a solution of 5-methyloxyindole (850.0 mg, 5.78 mmol) in DMF (10 mL) was added and heated at 80° C. for 3 hours. The reaction solution was alkalized by addition of 1N NaOH, and extracted with EA. The organic layer was washed with water, dried over $Na_2SO_4$, filtered, and distilled under reduced pressure. The residue was separated by column chromatography (n-Hex:EA=3:2) to obtain 600 mg of the title compound (yield 54%, pale yellow solid).

$^1H$ NMR (400 MHz, DMSO-$d_6$): δ 12.96 (s, 1H), 9.96 (s, 1H), 7.87 (s, 1H), 7.31 (d, J=8.3 Hz), 7.10 (dd, J=8.3, 1.5 Hz, 1H), 2.39 (s, 3H); mp 215° C.

Preparation Example 18: 2-Chloro-1-(2-ethoxyethyl)-5-methyl-1H-indol-3-carboxaldehyde

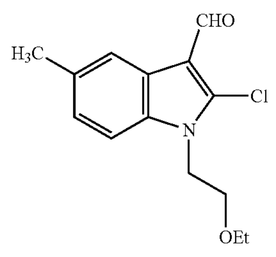 [SMILES: CCOCCn1c(Cl)c(C=O)c2cc(C)ccc21]

To a solution of 2-chloro-5-methyl-1H-indol-3-carboxaldehyde (440.0 mg, 2.27 mmol) in $CH_3CN$ (20 mL), 2-bromoethyl ethyl ether (303.8 μL, 2.72 mmol) and $Cs_2CO_3$ (3.71 g, 11.4 mmol) were added and refluxed for 15 hours. The reaction solution was distilled under reduced pressure, and water was added to the residue, followed by extraction with EA. The organic layer was dried over $MgSO_4$, filtered, and distilled under reduced pressure. The residue was separated by column chromatography (n-Hex:EA=9:1) to obtain 570 mg of the title compound (yield 94%, white solid).

$^1H$ NMR (400 MHz, $CDCl_3$): δ 10.09 (s, 1H), 8.10 (s, 1H), 7.28 (d, J=8.5 Hz, 1H), 7.14 (d, J=8.5, 1.5 Hz, 1H), 4.39 (t, J=5.5 Hz, 2H), 3.74 (t, J=5.5 Hz, 2H), 3.43 (q, J=7.0 Hz, 2H), 2.46 (s, 3H), 1.11 (t, J=7.0 Hz, 3H); $^{13}C$ NMR (400 MHz, DMSO-$d_6$) δ 184.35, 136.69, 134.28, 133.48, 125.59, 124.73, 121.19, 112.92, 109.89, 68.30, 67.09, 44.19, 21.61, 15.17; MS (MALDI-TOF) m/z 266 $[M+H]^+$; mp 54° C.

Preparation Example 19: 2-Chloro-5-methoxy-1H-indol-3-carboxaldehyde

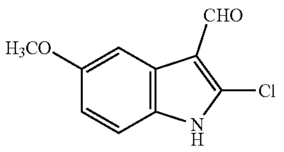 [SMILES: COc1ccc2[nH]c(Cl)c(C=O)c2c1]

$POCl_3$ (2.65 mL, 24.5 mmol) was added to DMF (10 mL) at 0° C., and stirred for 10 minutes. Then, a solution of 5-methoxyoxyindole (1.60 g, 9.81 mm) in DMF (10 mL) was added and heated at 80° C. for 2 hours. After alkalizing the reaction solution by adding 1N NaOH, the resulting solid was washed with water and dried to obtain the title compound. The filtrate was again extracted with EA, dried over $Na_2SO_4$, filtered, and distilled under reduced pressure. The residue was separated by column chromatography (n-Hex:EA=1:2) to obtain 1.27 g of the title compound (yield 62%, light brown solid).

$^1H$ NMR (300 MHz, DMSO-$d_6$): δ 12.96 (br s, 1H), 9.96 (s, 1H), 7.57 (d, J=2.7 Hz, 1H), 7.33 (d, J=8.7 Hz, 1H), 6.90 (dd, J=8.7, 2.7 Hz, 1H), 3.79 (s, 3H); mp 225° C.

Preparation Example 20: 2-Chloro-1-(2-ethoxyethyl)-5-methoxy-1H-indol-3-carboxaldehyde

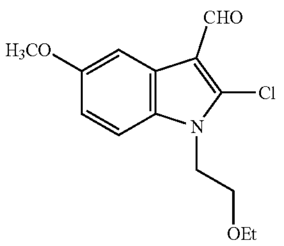 [SMILES: CCOCCn1c(Cl)c(C=O)c2cc(OC)ccc21]

5-Methoxy-2-chloro-1H-indol-3-carboxaldehyde (1.97 g, 9.40 mmol) was dissolved in DMF (70 mL), then 2-bromoethyl ethyl ether (1.26 mL, 11.3 mmol) and $Cs_2CO_3$ (15.3 g, 47.0 mmol) were added thereto, and heated at 70° C. for 11 hours. The reaction solution was diluted with water and extracted with EA. The organic layer was dried over $MgSO_4$, filtered, and distilled under reduced pressure. The residue was separated by column chromatography (n-Hex:EA=3:1) to obtain 2.18 g of the title compound (yield 82%, pale yellow solid).

$^1H$ NMR (400 MHz, $CDCl_3$): δ 10.09 (s, 1H), 7.79 (d, J=2.7 Hz, 1H), 7.29 (d, J=9.0 Hz, 1H), 6.94 (dd, J=9.0, 2.7 Hz, 1H), 4.37 (t, J=5.7 Hz, 2H), 3.89 (s, 3H), 3.74 (t, J=5.7 Hz, 2H), 3.43 (q, J=7.2 Hz, 2H), 1.11 (t, J=7.2 Hz, 3H); $^{13}C$ NMR (100 MHz, $CDCl_3$): δ 184.10, 156.90, 135.99, 130.59, 125.12, 114.17, 112.95, 111.06, 102.64, 68.21, 66.90, 55.77, 44.16, 14.96; MS (MALDI-TOF) m/z 282 $[M+H]^+$; mp 48° C.

Preparation Example 21: 6-Methoxyoxyindole

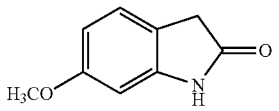 [SMILES: COc1ccc2c(c1)NC(=O)C2]

Ethylene glycol (10 mL) was added to 6-methoxyisatin (500 mg, 2.82 mmol), then KOH (158.2 mg, 2.82 mmol) and hydrazine monohydrate (282.3 mg, 5.64 mmol) were added thereto, and heated at 140° C. for 4 hours. The reaction solution was cooled, acidified with 1N HCl, and extracted with EA. The organic layer was distilled under reduced pressure, and the residue was separated by column chromatography (n-Hex:EA=1:1) to obtain 278 mg of the title compound (yield 60%, pale yellow solid).

$^1H$ NMR (400 MHz, DMSO-$d_6$): δ 10.30 (br s, 1H), 7.08 (d, J=8.0 Hz, 1H), 6.48 (d, J=8.0, 2.4 Hz, 1H), 6.38 (d, J=2.4 Hz, 1H), 3.71 (s, 3H), 3.37 (s, 2H)

Preparation Example 22: 2-Chloro-6-methoxy-1H-indol-3-carboxaldehyde

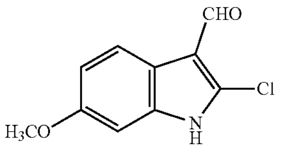 [SMILES: COc1ccc2c(C=O)c(Cl)[nH]c2c1]

$POCl_3$ (1.79 mL, 19.5 mmol) was added to DMF (5 mL) at 0° C., and stirred for 10 minutes. Then, a solution of 6-methoxyoxyindole (1.27 g, 7.78 mmol) in DMF (15 mL) was added and heated at 80° C. for 2 hours. After alkalizing the reaction solution by adding 1N NaOH, the resulting solid was filtered, washed with water, and dried to obtain the title compound. The filtrate was again extracted with EA, dried over $Na_2SO_4$, filtered, and distilled under reduced pressure. The residue was separated by column chromatography ($CH_2Cl_2$:EA=10:1) to obtain 945 mg of the title compound (yield, [Yong Yang2] white solid).

$^1H$ NMR (400 MHz, DMSO-$d_6$): δ 12.87 (br s, 1H), 9.94 (s, 1H), 7.91 (m, 1H), 6.89-6.87 (m, 2H), 3.79 (s, 3H); $^{13}C$ NMR (100 MHz, DMSO-$d_6$) δ 183.09, 156.90, 135.57, 133.26, 120.73, 118.09, 112.23, 112.10, 95.09, 55.31; mp 230° C.

Preparation Example 23: 2-Chloro-1-(2-ethoxyethyl)-6-methoxy-1H-indol-3-carboxaldehyde

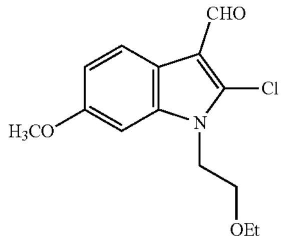 [SMILES: CCOCCn1c(Cl)c(C=O)c2ccc(OC)cc21]

6-Methoxy-2-chloro-1H-indol-3-carboxaldehyde (765.1 mg, 3.65 mmol) was dissolved in DMF (15 mL), then 2-bromoethyl ethyl ether (489.2 μL, 4.38 mmol) and $Cs_2CO_3$ (3.58 g, 11.0 mmol) were added thereto, and heated at 70° C. for 5 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=3:1:0.5) to obtain 420 mg of the title compound (yield 41%, white solid).

$^1$H NMR (400 MHz, $CDCl_3$): δ 10.08 (s, 1H), 8.15 (d, J=8.8 Hz, 1H), 6.95 (dd, J=8.8, 2.4 Hz, 1H), 6.89 (d, J=2.4 Hz, 1H), 4.36 (t, J=5.6 Hz, 2H), 3.87 (s, 3H), 3.75 (t, J=5.6 Hz, 2H), 3.45 (q, J=7.2 Hz, 2H), 1.13 (t, J=7.2 Hz, 3H); $^{13}$C NMR (100 MHz, DMSO-$d_6$): δ 184.02, 157.51, 136.85, 135.25, 122.00, 118.29, 113.20, 112.31, 94.46, 68.25, 66.92, 55.68, 44.00, 15.04; MS (MALDI-TOF): m/z 281 $[M]^+$; mp 82° C.

Preparation Example 24: 2-Chloro-5-fluoro-1H-indol-3-carboxaldehyde

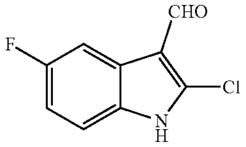 [SMILES: O=Cc1c(Cl)[nH]c2ccc(F)cc12]

$POCl_3$ (1.36 mL, 14.9 mmol) was added to DMF (5 mL) at 0° C., and stirred for 10 minutes. Then, a solution of 5-fluorooxyindole (900.0 mg, 5.95 mmol) in DMF (15 mL) was added and heated at 80-C for 4 hours. The reaction solution was alkalized by addition of 1N NaOH, and extracted with EA. The organic layer was dried over $Na_2SO_4$, filtered, and distilled under reduced pressure. The residue was separated by column chromatography (n-Hex: EA=1:1) to obtain 235 mg of the title compound (yield 20%, white solid).

$^1$H NMR (300 MHz, DMSO-$d_6$): δ 13.22 (br s, 1H), 9.96 (s, 1H), 7.73 (dd, J=9.0, 2.7 Hz, 1H), 7.45 (dd, J=9.0, 4.5 Hz, 1H), 7.13 (m, 1H); $^{13}$C NMR (100 MHz, DMSO-$d_6$) δ 183.27, 158.93 (d, J=235.2 Hz), 135.60, 131.21, 124.89 (d, J=11.3 Hz), 113.27 (d, J=9.9 Hz), 112.11 (d, J=4.4 Hz), 111.92 (d, J=25.9 Hz), 105.09 (d, J=25.1 Hz); mp 208-210° C.

Preparation Example 25: 2-Chloro-1-(2-ethoxyethyl)-5-fluoro-1H-indol-3-carboxaldehyde

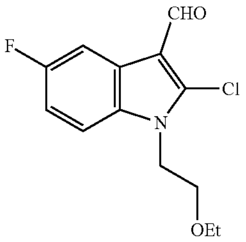 [SMILES: CCOCCn1c(Cl)c(C=O)c2cc(F)ccc21]

2-Chloro-5-fluoro-1H-indol-3-carboxaldehyde (197.6 mg, 1.0 mmol) was dissolved in DMF (5 mL), then 2-bromoethyl ethyl ether (134.0 μL, 1.2 mmol) and $Cs_2CO_3$ (977.5 mg, 3.0 mmol) were added thereto, and heated at 70° C. for 15 hours. The reaction solution was diluted with water and extracted with EA. The organic layer was dried over $MgSO_4$, filtered, and distilled under reduced pressure. The residue was separated by column chromatography (n-Hex: $CH_2Cl_2$:EA=3:1:0.5) to obtain 125 mg of the title compound (yield 46%, white solid).

$^1$H NMR (400 MHz, $CDCl_3$): δ 10.09 (s, 1H), 7.98 (d, J=9.2, 2.4 Hz, 1H), 7.36 (d, J=9.2, 4.4 Hz, 1H), 7.06 (m, 1H), 4.41 (t, J=5.6 Hz, 2H), 3.76 (t, J=5.6 Hz, 2H), 3.43 (q, J=7.2 Hz, 2H), 1.11 (t, J=7.2 Hz, 3H); $^{13}$C NMR (400 MHz, DMSO-$d_6$): δ 183.79, 159.96 (d, J=238.6 Hz), 137.13, 132.38, 124.95 (d, J=11.3 Hz), 113.07 (d, J=4.4 Hz), 112.19 (d, J=26.2 Hz), 111.30 (d, J=9.4 Hz), 106.80 (d, J=25.1 Hz), 68.23, 66.91, 44.37, 14.93; MS (MALDI-TOF): m/z 270 $[M+H]^+$; mp 83-84° C.

Preparation Example 26: 2,5-Dichloro-1H-indol-3-carboxaldehyde

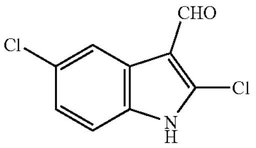 [SMILES: O=Cc1c(Cl)[nH]c2ccc(Cl)cc12]

$POCl_3$ (2.74 mL, 29.9 mmol) was added to DMF (5 mL) at 0° C., and stirred for 10 minutes. Then, a solution of 5-chlorooxyindole (1.0 g, 5.97 mmol) in DMF (5 mL) was added and heated at 80° C. for 3 hours. The reaction solution was alkalized by addition of 1N NaOH, and extracted with EA. The organic layer was washed with water, dried over $Na_2SO_4$, filtered, and distilled under reduced pressure. The residue was separated by column chromatography (n-Hex: EA=2:1) to obtain 530 mg of the title compound (yield 41%, light brown solid).

$^1$H NMR (400 MHz, DMSO-$d_6$): δ 13.31 (br s, 1H), 9.97 (s, 1H), 8.04 (d, J=2.0 Hz, 1H), 7.47 (d, J=8.5 Hz, 1H), 7.31 (dd, J=8.5, 2.0 Hz, 1H); mp 245-248° C.

Preparation Example 27: 2,5-Dichloro-1-(2-ethoxyethyl)-1H-indol-3-carboxaldehyde

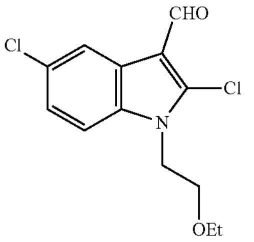 [SMILES: CCOCCn1c(Cl)c(C=O)c2cc(Cl)ccc21]

To a solution in which 2,5-dichloro-1H-indol-3-carboxaldehyde (350 mg, 1.64 mmol) obtained in Preparation Example 26 was dissolved in $CH_3CN$ (20 mL), 2-bromoethyl ethyl ether (274.8 μL, 2.46 mmol) and $Cs_2CO_3$ (2.67 g, 8.20 mmol) were added and refluxed for 15 hours. The reaction solution was distilled under reduced pressure, and water was added to the residue, followed by extraction with EA. The organic layer was dried over $MgSO_4$, filtered, and distilled under reduced pressure. The residue was separated by column chromatography (n-Hex:EA=9:1) to obtain 360 mg of the title compound (yield 77%, pale yellow solid).

$^1H$ NMR (400 MHz, $CDCl_3$): δ 10.06 (s, 1H), 8.26 (d, J=2.0 Hz, 1H), 7.32-7.23 (m, 2H), 4.38 (t, J=5.6 Hz, 2H), 3.73 (t, J=5.6 Hz, 2H), 3.41 (q, J=7.2 Hz, 2H), 1.08 (t, J=7.2 Hz, 3H); $^{13}C$ NMR (100 MHz, DMSO-$d_6$): δ 184.01, 137.39, 134.50, 129.64, 125.40, 124.51, 120.95, 112.84, 111.60, 68.41, 67.13, 44.55, 15.15; MS (MALDI-TOF): m/z 286 $[M+H]^+$; mp 104° C.

Preparation Example 28: 5-(Trifluoromethoxy)oxyindole

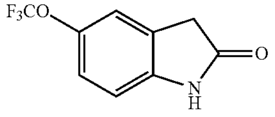 [SMILES: O=C1Cc2cc(OC(F)(F)F)ccc2N1]

Ethylene glycol (10 mL) was added to 5-(trifluoromethoxy)isatin (1.75 g, 7.57 mmol), then KOH (424.8 mg, 7.57 mmol) and hydrazine monohydrate (1.14 g, 22.7 mmol) were added thereto, and heated at 140° C. for 4 hours. The reaction solution was cooled, acidified with 1N HCl, and extracted with EA. The organic layer was distilled under reduced pressure, and the residue was separated by column chromatography (n-Hex:EA=1:2) to obtain 855 mg of the title compound ([Yong Yang3] yield 52%, light brown solid).

$^1H$ NMR (400 MHz, DMSO-$d_6$) δ 10.52 (br s, 1H), 7.24 (s, 1H), 7.16 (m, 1H), 6.86 (d, J=8.0 Hz, 1H), 3.54 (s, 2H)

Preparation Example 29: 2-Chloro-5-(trifluoromethoxy)-1H-indol-3-carboxaldehyde

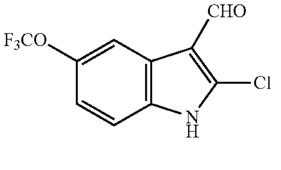 [SMILES: O=Cc1c(Cl)[nH]c2ccc(OC(F)(F)F)cc12]

$POCl_3$ (727.7 μL, 7.95 mmol) was added to DMF (1 mL) at 0° C., and stirred for 10 minutes. Then, a solution of 5-(trifluoromethoxy)oxyindole (575.0 mg, 2.65 mmol) in DMF (5 mL) was added and heated at 80° C. for 3 hours. The reaction solution was alkalized by addition of 1N NaOH, and extracted with EA. The organic layer was dried over $Na_2SO_4$, filtered, and distilled under reduced pressure. The residue was separated by column chromatography (n-Hex:EA=1:1) to obtain 120 mg of the title compound (yield 17%, white solid).

$^1H$ NMR (400 MHz, DMSO-$d_6$): δ 13.40 (br s, 1H), 9.99 (s, 1H), 7.95 (m, 1H), 7.54 (d, J=8.8 Hz, 1H), 7.29 (m, 1H); mp 191-192° C.

Preparation Example 30: 2-Chloro-1-(2-ethoxyethyl)-5-(trifluoromethoxy)-1H-indol-3-carboxaldehyde

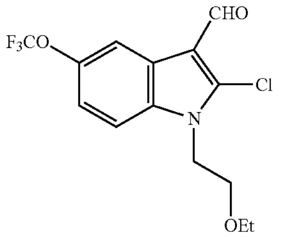 [SMILES: CCOCCn1c(Cl)c(C=O)c2cc(OC(F)(F)F)ccc21]

2-Chloro-5-(trifluoromethoxy)-1H-indol-3-carboxaldehyde (100 mg, 0.38 mmol) was dissolved in DMF (3 mL), then 2-bromoethyl ethyl ether (51.4 μL, 0.46 mmol) and $Cs_2CO_3$ (371.4 mg, 1.14 mmol) were added thereto, and heated at 70° C. for 8 hours. The reaction solution was diluted with water and extracted with EA. The organic layer was dried over $MgSO_4$, filtered, and distilled under reduced pressure. The residue was separated by column chromatography (n-Hex:$CH_2Cl_2$:EA=4:4:1) to obtain 43 mg of the title compound (yield 34%, pale yellow solid).

$^1H$ NMR (400 MHz, $CDCl_3$): δ 10.11 (s, 1H), 8.18 (s, 1H), 7.42 (d, J=8.8 Hz, 1H), 7.20 (dd, J=8.8, 1.6 Hz, 1H), 4.42 (t, J=5.6 Hz, 2H), 3.77 (t, J=5.6 Hz, 2H), 3.44 (q, J=5.2 Hz, 2H), 1.11 (t, J=7.2 Hz, 3H); $^{13}C$ NMR (100 MHz, $CDCl_3$): δ 183.78, 145.66 (q, J=1.9 Hz), 137.58, 134.20, 124.73, 120.62 (q, J=255.0 Hz), 117.81, 113.86 (q, J=0.8 Hz), 113.23, 111.29, 68.25, 66.96, 44.46, 14.94; MS (MALDI-TOF): m/z 335 $[M]^+$; mp 79° C.

Preparation Example 31: 2-Bromo-1H-indol-3-carboxaldehyde

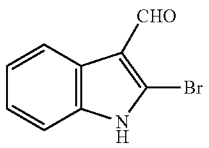 [SMILES: O=Cc1c(Br)[nH]c2ccccc12]

DMF (1.8 mL) was added to $CH_2Cl_2$ (6 mL) at 0° C., and then a solution of $POBr_3$ (5.33 g, 18.6 mmol) in $CH_2Cl_2$ (10 mL) was slowly added and refluxed for 15 minutes. Thereafter, oxyindole (1.03 g, 7.74 mmol) was added little by little, and the mixture was refluxed for 1 hour more. The reaction solution was put in cold water and stirred for 20 minutes to separate the water layer. The water layer was neutralized with solid $K_2CO_3$ and the resulting solid was filtered. The obtained solid was purified by column chromatography (n-Hex:EA=2:1) to obtain 1.2 g of the title compound (yield 70|Yong Yang4]%, light brown solid).

$^1$H NMR (400 MHz, DMSO-$d_6$): δ 13.04 (br s, 1H), 9.90 (s, 1H), 8.08 (m, 1H), 7.43 (m, 1H), 7.29-7.21 (m, 2H)

Preparation Example 32: Ethyl 2-(2-bromo-3-formyl-1H-indol-1-yl)acetate

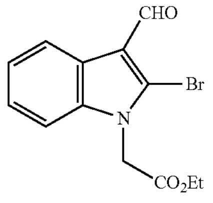 [SMILES: CCOC(=O)Cn1c(Br)c(C=O)c2ccccc21]

THF (5 mL) and DMF (2 mL) were added to 2-bromo-1H-indol-3-carboxaldehyde (120.0 mg, 0.54 mmol) obtained in Preparation Example 31 and NaH (32.4 mg, 0.81 mmol, 60% in oil) at 0° C. and stirred for 5 minutes. Then, ethyl bromoacetate (72.1 μL, 0.65 mmol) was added and stirred at room temperature for 15 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 91 mg of the title compound (yield 54%, white solid).

$^1$H NMR (400 MHz, $CDCl_3$): δ 10.07 (s, 1H), 8.33 (m, 1H), 7.34-7.31 (m, 2H), 7.25 (m, 1H), 4.99 (s, 2H), 4.26 (q, J=7.2 Hz, 2H), 1.28 (t, J=7.2 Hz, 3H); $^{13}$C NMR (100 MHz, $CDCl_3$): δ 185.45, 166.55, 137.11, 126.09, 125.18, 124.49, 123.62, 121.40, 116.07, 109.21, 62.35, 46.27, 14.06; MS (MALDI-TOF): m/z 309 $[M]^+$; mp 94° C.

Preparation Example 33: 2-Bromo-1-(2-ethoxyethyl)-1H-indol-3-carboxaldehyde

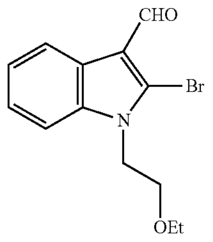 [SMILES: CCOCCn1c(Br)c(C=O)c2ccccc21]

2-Bromo-1H-indol-3-carboxaldehyde (400.0 mg, 1.79 mmol) obtained in Preparation Example 31 was dissolved in DMF (10 mL), then 2-bromoethyl ethyl ether (240.1 μL, 2.15 mmol) and $Cs_2CO_3$ (1.75 g, 5.37 mmol) were added thereto, and heated at 70° C. for 6 hours. The reaction solution was diluted with water and extracted with EA. The organic layer was dried over $MgSO_4$, filtered, and distilled under reduced pressure. The residue was separated by column chromatography ($CH_2Cl_2$:EA=20:1) to obtain 436 mg of the title compound (yield 82%, white solid).

$^1$H NMR (400 MHz, $CDCl_3$): δ 10.06 (s, 1H), 8.32 (m, 1H), 7.43 (m, 1H), 7.34-7.30 (m, 2H), 4.46 (t, J=5.6 Hz, 2H), 3.77 (t, J=5.6 Hz, 2H), 3.45 (q, J=7.2 Hz, 2H), 1.23 (t, J=7.2 Hz, 3H); $^{13}$C NMR (100 MHz, $CDCl_3$): δ 185.61, 137.43, 126.59, 125.43, 124.25, 123.57, 121.30, 115.60, 110.47, 68.40, 67.14, 45.59, 15.17; MS (MALDI-TOF): m/z 295 $[M]^+$; mp 56-57° C.

Preparation Example 34: 2-(Trifluoromethyl)-1H-indol-3-carboxaldehyde

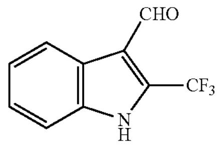 [SMILES: O=Cc1c(C(F)(F)F)[nH]c2ccccc12]

$POCl_3$ (1.83 mL, 20.0 mmol) was added to DMF (10 mL) at 0° C., and stirred for 10 minutes. Then, a solution of 2-trifluoromethylindole (740.6 mg, 4.0 mmol (Yong Yang5f) in DMF (10 mL) was added and heated at 80° C. for 5 hours. The reaction solution was alkalized by addition of 1N NaOH, and extracted with EA. The organic layer was washed with brine, dried over $Na_2SO_4$, filtered, and distilled under reduced pressure. The residue was separated by column chromatography (n-Hex:EA=7:1) to obtain 324 mg of the title compound (yield 38%, white solid).

$^1$H NMR (400 MHz, DMSO-$d_6$): δ 13.42 (br s, 1H), 10.24 (s, 1H), 8.25 (d, J=8.0 Hz, 1H), 7.61 (d, J=8.0 Hz, 1H), 7.44 (m, 1H), 7.36 (m, 1H); mp 171-173° C.

Preparation Example 35: 1-(2-Ethoxyethyl)-2-(trifluoromethyl)-1H-indol-3-carboxaldehyde

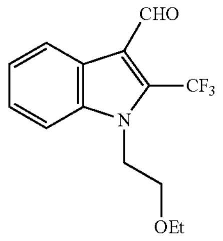 [SMILES: CCOCCn1c(C(F)(F)F)c(C=O)c2ccccc21]

2-(Trifluoromethyl)-1H-indol-3-carboxaldehyde (350.0 mg, 1.64 mmol) was dissolved in DMF (10 mL), then 2-bromoethyl ethyl ether (220.0 μL, 1.97 mmol) and $Cs_2CO_3$ (1.60 g, 4.92 mmol) were added thereto, and heated at 70-C for 15 hours. The reaction solution was diluted with water and extracted with EA. The organic layer was dried over $MgSO_4$, filtered, and distilled under reduced pressure. The residue was separated by column chromatography (n-Hex:EA=5:1) to obtain 184 mg of the title compound (yield 39%, white solid).

$^1$H NMR (400 MHz, $CDCl_3$): δ 10.41 (s, 1H), 8.52 (d, J=8.0 Hz, 1H), 7.58 (d, J=8.0 Hz, 1H), 7.46 (m, 1H), 7.39 (m, 1H), 4.52 (t, J=6.0 Hz, 2H), 3.80 (t, J=6.0 Hz, 2H), 3.45 (q, J=7.2 Hz, 2H), 1.13 (t, J=7.2 Hz, 3H); $^{13}$C NMR (100 MHz, $CDCl_3$): δ 185.81, 137.63, 131.27 (q, J=37.9 Hz), 126.02, 124.30, 124.21, 123.66, 121.29 (q, J=270.3 Hz), 117.84 (q, J=1.5 Hz), 111.18, 68.82, 66.93, 45.58 (q, J=2.5 Hz), 14.94; MS (MALDI-TOF): m/z 286 $[M+H]^+$; mp 46° C.

Preparation of Benzofuran-Based N-Acylhydrazone Derivative

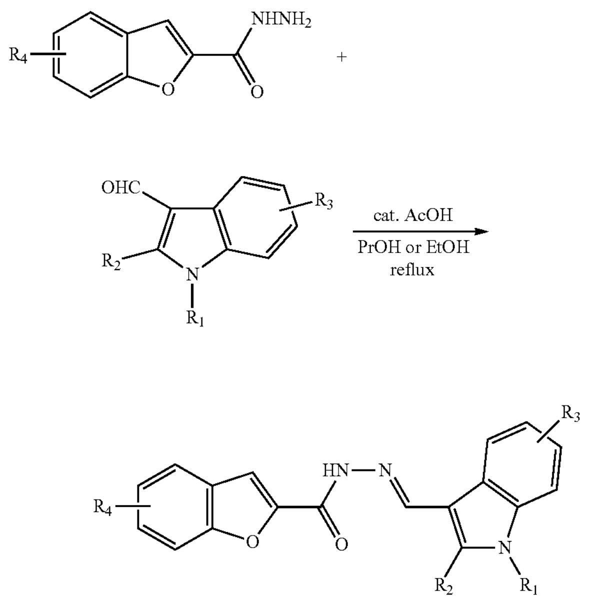

$R_1$ = H, $CH_3$, $—CH_2CO_2Et$, $—CH_2CH_2OEt$, $—CH_2CH_2OMe$
$R_2$ = Cl, Br, $CF_3$, $CH_3$
$R_3$ = H, 5-$CH_3$, 5-$OCH_3$, 6-$OCH_3$, 5-F, 5-Cl, 5-$OCF_3$
$R_4$ = 5-$CH_3$, 5-$OCH_3$, 5-Cl, 4,7-Dimethyl, 4,6-Dimethoxy, 5-$HNCOCH_3$ Example 1: Preparation of (E)-N'-[(2-chloro-1H-indol-3-yl)methylene]-5-methylbenzofuran-2-carbohydrazide

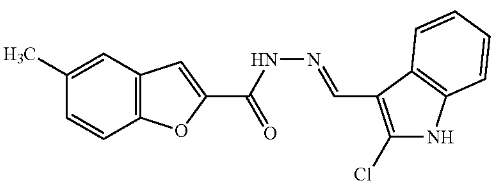 [SMILES: Cc1ccc2oc(C(=O)N/N=C/c3c(Cl)[nH]c4ccccc34)cc2c1]

To 5-methylbenzofuran-2-carbohydrazide (95.1 mg, 0.50 mmol) and 2-chloro-1H-indol-3-carboxaldehyde (89.8 mg, 0.50 mmol), 1-PrOH (15 mL) and acetic acid (1-2 drops) were added and refluxed for 8 hours. The reaction solution was distilled under reduced pressure, and the residue was washed with a mixed solvent of n-Hex/$CH_2Cl_2$ (1:1) to obtain 153 mg of the title compound (yield 87%, pale yellow solid).

$^1$H NMR (300 MHz, DMSO-$d_6$) δ 12.48 (s, 1H), 11.98 (s, 1H), 8.73 (s, 1H), 8.28 (d, J=7.2 Hz, 1H), 7.63-7.58 (m, 3H), 7.39 (d, J=7.2 Hz, 1H), 7.32 (d, J=8.8 Hz, 1H), 7.27-7.19 (m, 2H), 2.44 (s, 3H); $^{13}$C NMR (100 MHz, DMSO-$d_6$) δ 154.20, 152.86, 148.41, 142.86, 135.02, 132.91, 128.33, 127.26, 127.16, 124.06, 123.20, 122.24, 121.33, 121.28, 111.37, 111.21, 110.03, 107.39, 20.83; HRMS (TOF MS $ES^-$): m/z calcd for $C_{19}H_{13}ClN_3O_2$ $(M-H)^-$ 350.0696, found 350.0700; mp 242° C. dec.

Example 2: Preparation of (E)-N'-[(2-chloro-1-methyl-1H-indol-3-yl)methylene]-5-methylbenzofuran-2-carbohydrazide

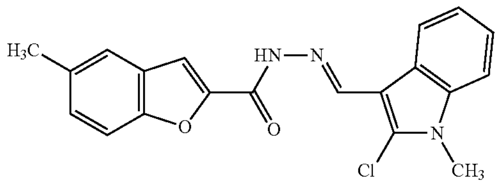 [SMILES: Cc1ccc2oc(C(=O)N/N=C/c3c(Cl)n(C)c4ccccc34)cc2c1]

To 5-methylbenzofuran-2-carbohydrazide (95.1 mg, 0.50 mmol) and 2-chloro-1-methyl-1H-indol-3-carboxaldehyde (96.8 mg, 0.50 mmol), 1-PrOH (15 mL) and acetic acid (1-2 drops) were added and refluxed for 24 hours. The reaction solution was cooled, and the solid was filtered and washed with EtOH to obtain 100 mg of the title compound (yield 55%, light brown solid).

$^1$H NMR (400 MHz, DMSO-$d_6$): δ 12.00 (s, 1H), 8.75 (s, 1H), 8.32 (d, J=7.6 Hz, 1H), 7.63-7.57 (m, 4H), 7.35-7.25 (m, 3H), 3.81 (s, 3H), 2.43 (s, 3H); $^{13}$C NMR (100 MHz, DMSO-$d_6$): δ 154.22, 152.87, 148.40, 142.93, 136.08, 132.92, 129.29, 128.34, 127.16, 123.24, 123.21, 122.25, 121.67, 121.42, 111.38, 110.34, 110.06, 107.28, 30.19, 20.84; HRMS (TOF MS $ES^-$): m/z calcd for $C_{20}H_{15}ClN_3O_2$ $(M-H)^-$ 364.0853, found 364.0847; mp 246-247° C.

Example 3: Preparation of ethyl (E)-2-{2-chloro-3-[(2-(5-methylbenzofuran-2-carbonyl)hydrazinylidene)methyl]-1H-indol-1-yl}acetate

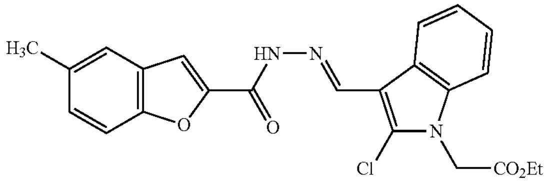 [SMILES: CCOC(=O)Cn1c(Cl)c(/C=N/NC(=O)c2cc3cc(C)ccc3o2)c2ccccc21]

To 5-methylbenzofuran-2-carbohydrazide (60.9 mg, 0.32 mmol) and ethyl 2-(2-chloro-3-formyl-1H-indol-1-yl)acetate (85.0 mg, 0.32 mmol), 1-PrOH (15 mL) and acetic acid (1-2 drops) were added and refluxed for 30 hours. The reaction solution was distilled under reduced pressure, and the residue was washed with $Et_2O$ to obtain 85 mg of the title compound (yield 61%, white solid).

$^1$H NMR (400 MHz, DMSO-$d_6$): δ 12.06 (s, 1H), 8.76 (s, 1H), 8.34 (d, J=6.8 Hz, 1H), 7.64-7.58 (m, 4H), 7.34-7.27 (m, 3H), 5.26 (s, 2H), 4.19 (q, J=7.2 Hz, 2H), 2.43 (s, 3H), 1.22 (t, J=7.2 Hz, 3H); $^{13}$C NMR (100 MHz, DMSO-$d_6$): δ 167.84, 154.28, 152.88, 148.33, 142.65, 136.14, 132.94, 129.17, 128.39, 127.15, 123.57, 123.29, 122.27, 121.97, 121.49, 111.39, 110.30, 110.19, 108.22, 61.45, 44.78, 20.84, 14.00; HRMS (TOF MS $ES^-$): m/z calcd for $C_{23}H_{19}ClN_3O_4$ $(M-H)^-$ 436.1064, found 436.1068; mp 198° C.

Example 4: Preparation of (E)-N'-[(2-chloro-1-(2-ethoxyethyl)-1H-indol-3-yl]methylene}-5-methylbenzofuran-2-carbohydrazide

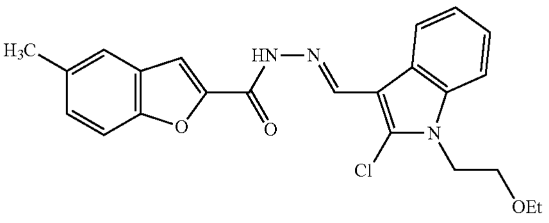 [SMILES: CCOCCn1c(Cl)c(/C=N/NC(=O)c2cc3cc(C)ccc3o2)c2ccccc21]

To 5-methylbenzofuran-2-carbohydrazide (98.9 mg, 0.52 mmol) and 2-chloro-1-(2-ethoxyethyl)-1H-indol-3-carboxaldehyde (130.9 mg, 0.52 mmol), 1-PrOH (15 mL) and acetic acid (1-2 drops) were added and refluxed for 24 hours. The reaction solution was distilled under reduced pressure, and the residue was separated by column chromatography (n-Hex:EA=1:1) to obtain 179 mg of the title compound (yield 81%, pale yellow solid).

$^1$H NMR (400 MHz, DMSO-$d_6$): δ 12.01 (s, 1H), 8.75 (s, 1H), 8.32 (d, J=7.6 Hz, 1H), 7.63-7.58 (m, 4H), 7.33-7.24 (m, 3H), 4.46 (t, J=5.6 Hz, 2H), 3.71 (t, J=5.6 Hz, 2H), 3.39 (q, J=6.8 Hz, 2H), 2.43 (s, 3H), 1.00 (t, J=6.8 Hz, 3H); $^{13}$C NMR (100 MHz, DMSO-$d_6$): δ 154.23, 152.87, 148.40, 142.99, 135.76, 132.92, 129.26, 128.34, 127.16, 123.35, 123.21, 122.25, 121.67, 121.43, 111.37, 110.67, 110.08, 107.53, 67.85, 65.63, 43.52, 20.83, 14.90; HRMS (TOF MS $ES^-$): m/z calcd for $C_{23}H_{21}ClN_3O_3$ $(M-H)^-$ 422.1271, found 422.1261; mp 172° C.

Example 5: Preparation of (E)-N'-[(2-bromo-1-(2-ethoxyethyl)-1H-indol-3-yl]methylene}-5-methylbenzofuran-2-carbohydrazide

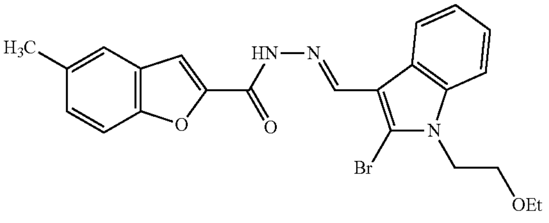 [SMILES: CCOCCn1c(Br)c(/C=N/NC(=O)c2cc3cc(C)ccc3o2)c2ccccc21]

To 5-methylbenzofuran-2-carbohydrazide (108.4 mg, 0.57 mmol) and 2-bromo-1-(2-ethoxyethyl)-1H-indol-3-carboxaldehyde (168.8 mg, 0.57 mmol), 1-PrOH (15 mL) and acetic acid (1-2 drops) were added and refluxed for 24 hours. The reaction solution was distilled under reduced pressure, dissolved in a small amount of $CH_2Cl_2$, and then added dropwise to n-Hex solution. The resulting solid was filtered to obtain 209 mg of the title compound (yield 78%, pale yellow solid).

$^1$H NMR (400 MHz, DMSO-$d_6$): δ 12.03 (s, 1H), 8.72 (s, 1H), 8.35 (d, J=7.2 Hz, 1H), 7.63-7.58 (m, 4H), 7.33-7.22 (m, 3H), 4.48 (t, J=5.6 Hz, 2H), 3.71 (t, J=5.6 Hz, 2H), 3.39 (q, J=7.2H, 2H), 2.44 (s, 3H), 1.01 (t, J=7.2 Hz, 3H); $^{13}$C NMR (100 MHz, DMSO-$d_6$): δ 154.21, 152.86, 148.41, 144.36, 137.00, 132.90, 128.32, 127.16, 124.14, 123.13, 122.23, 121.46, 121.29, 119.80, 111.36, 110.77, 110.43, 110.03, 67.96, 65.69, 44.81, 20.83, 14.91; HRMS (TOF MS $ES^-$): m/z calcd for $C_{23}H_{21}BrN_3O_3$ $(M-H)^-$ 466.0766, found 466.0776; mp 190° C.

Example 6: Preparation of (E)-N'-{[1-(2-ethoxyethyl)-2-(trifluoromethyl)-1H-indol-3-yl]methylene}-5-methylbenzofuran-2-carbohydrazide

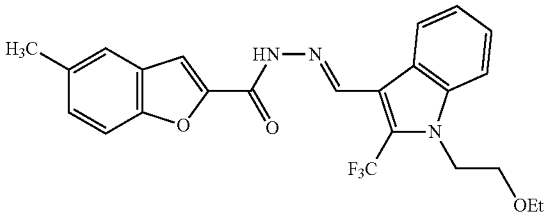 [SMILES: CCOCCn1c(C(F)(F)F)c(/C=N/NC(=O)c2cc3cc(C)ccc3o2)c2ccccc21]

To 5-methylbenzofuran-2-carbohydrazide (93.2 mg, 0.49 mmol) and 1-(2-ethoxyethyl)-2-trifluoromethyl-1H-indol-3-carboxaldehyde (139.8 mg, 0.49 mmol), 1-PrOH (15 mL) and acetic acid (1-2 drops) were added and refluxed for 24 hours. The reaction solution was distilled under reduced pressure, and the residue was separated by column chromatography (n-Hex:EA=2:1) to obtain 176 mg of the title compound (yield 79%, white solid).

$^1$H NMR (400 MHz, DMSO-$d_6$): δ 12.24 (s, 1H), 9.00 (s, 1H), 8.63 (d, J=8.0 Hz, 1H), 7.75 (d, J=8.4 Hz, 1H), 7.67 (s, 1H), 7.61-7.59 (m, 2H), 7.47 (m, 1H), 7.37-7.32 (m, 2H), 4.54 (t, J=5.4 Hz, 2H), 3.72 (t, J=5.4 Hz, 2H), 3.37 (q, J=7.0 Hz, 2H), 2.44 (s, 3H), 10.00 (t, J=7.0 Hz, 3H); $^{13}$C NMR (100 MHz, DMSO-$d_6$): δ 154.52, 152.93, 148.17, 142.47, 137.83, 133.01, 128.53, 127.12, 125.66, 125.10 (q, J=35.8 Hz), 124.20, 123.14, 122.48, 122.32, 121.75 (q, J=269.0 Hz), 113.45, 111.85, 111.42, 110.56, 68.36, 65.79, 45.01, 20.84, 14.85; $^{19}$F NMR (376 MHz, DMSO-$d_6$): δ −52.9 (s, 3F); HRMS (TOF MS $ES^-$): m/z calcd for $C_{24}H_{21}F_3N_3O_3$ $(M-H)^-$ 456.1535, found 456.1531; mp 183° C.

Example 7: Preparation of (E)-N'-[(2-chloro-1-(2-methoxyethyl)-1H-indol-3-yl]methylene}-5-methylbenzofuran-2-carbohydrazide

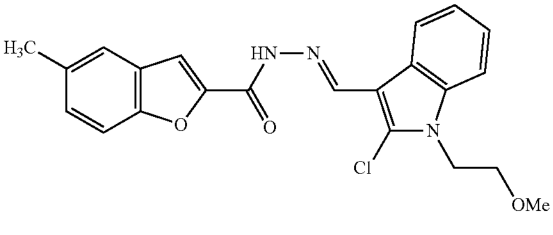 [SMILES: COCCn1c(Cl)c(/C=N/NC(=O)c2cc3cc(C)ccc3o2)c2ccccc21]

To 5-methylbenzofuran-2-carbohydrazide (319.5 mg, 1.68 mmol) and 2-chloro-1-(2-methoxyethyl)-1H-indol-3-carboxaldehyde (399.3 mg, 1.68 mmol), 1-PrOH (20 mL) and acetic acid (1-2 drops) were added and refluxed for 15 hours. The reaction solution was cooled, and the solid was filtered and washed with n-Hex to obtain 630 mg of the title compound (yield 91%, pale yellow solid).

$^1$H NMR (400 MHz, DMSO-$d_6$): δ 12.01 (s, 1H), 8.75 (s, 1H), 8.33 (d, J=7.5 Hz, 1H), 7.63-7.58 (m, 4H), 7.33-7.24 (m, 3H), 4.48 (t, J=5.4 Hz, 2H), 3.68 (t, J=5.4 Hz, 2H), 3.21 (s, 3H), 2.43 (s, 3H); $^{13}$C NMR (100 MHz, DMSO-$d_6$): δ

154.23, 152.88, 148.40, 142.97, 135.76, 132.93, 129.20, 128.36, 127.16, 123.34, 123.25, 122.25, 121.68, 121.44, 111.38, 110.68, 110.10, 107.55, 70.11, 58.29, 43.34, 20.84; HRMS (TOF MS $ES^-$): m/z calcd for $C_{22}H_{19}ClN_3O_3$ $(M-H)^-$ 408.1115, found 408.1099; mp 243° C.

Example 8: Preparation of (E)-N'-[(2-chloro-1-(2-ethoxyethyl)-5-methoxy-1H-indol-3-yl]methylene}-5-methylbenzofuran-2-carbohydrazide

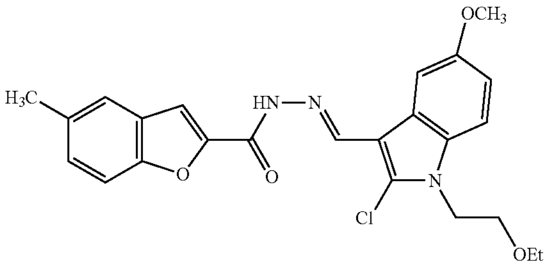 [SMILES: CCOCCn1c(Cl)c(/C=N/NC(=O)c2cc3cc(C)ccc3o2)c2cc(OC)ccc21]

To 5-methylbenzofuran-2-carbohydrazide (127.4 mg, 0.67 mmol) and 2-chloro-1-(2-ethoxyethyl)-5-methoxy-1H-indol-3-carboxaldehyde (188.8 mg, 0.67 mmol), 1-PrOH (15 mL) and acetic acid (1-2 drops) were added and refluxed for 24 hours. The reaction solution was distilled under reduced pressure, and the residue was separated by column chromatography (n-Hex:EA=1:2) to obtain 213 mg of the title compound (yield 70%, pale yellow solid).

$^1H$ NMR (400 MHz, DMSO-$d_6$): δ 12.01 (s, 1H), 8.73 (s, 1H), 7.91 (d, J=2.4 Hz, 1H), 7.61-7.57 (m, 3H), 7.52 (d, J=9.2 Hz, 1H), 7.32 (dd, J=8.8, 1.6 Hz, 1H), 6.95 (dd, J=8.8, 2.4 Hz, 1H), 4.42 (t, J=5.2 Hz, 2H), 3.82 (s, 3H), 3.68 (t, J=5.2 Hz, 2H), 3.38 (q, J=7.2 Hz, 2H), 2.43 (s, 3H), 1.00 (t, J=7.2 Hz, 3H); $^{13}C$ NMR (400 MHz, DMSO-$d_6$): δ 155.20, 154.17. 152.85, 148.48, 142.94, 132.91, 130.74, 128.95, 128.31, 127.17, 124.01, 122.23, 112.24, 111.53, 111.35, 110.04, 107.24, 104.11, 67.91, 65.62, 55.33, 43.65, 20.83, 14.90; HRMS (TOF MS $ES^-$): m/z calcd for $C_{24}H_{23}ClN_3O_4$ $(M-H)^-$ 452.1377, found 452.1355; mp 208° C.

Example 9: Preparation of (E)-N'-[(2-chloro-1-(2-ethoxyethyl)-6-methoxy-1H-indol-3-yl]methylene}-5-methylbenzofuran-2-carbohydrazide

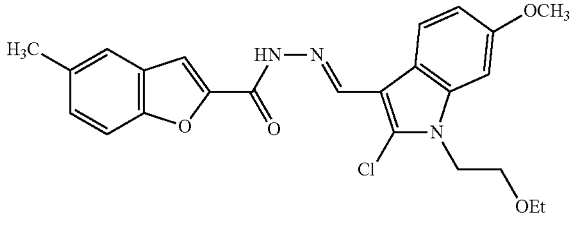 [SMILES: CCOCCn1c(Cl)c(/C=N/NC(=O)c2cc3cc(C)ccc3o2)c2ccc(OC)cc21]

To 5-methylbenzofuran-2-carbohydrazide (95.1 mg, 0.50 mmol) and 2-chloro-1-(2-ethoxyethyl)-6-methoxy-1H-indol-3-carboxaldehyde (140.9 mg, 0.50 mmol), 1-PrOH (15 mL) and acetic acid (1-2 drops) were added and refluxed for 16 hours.

The reaction solution was distilled under reduced pressure, dissolved in a small amount of $CH_2Cl_2$, and then added dropwise to n-Hex solution. The resulting solid was filtered to obtain 205 mg of the title compound (yield 90%, pale yellow solid).

$^1H$ NMR (400 MHz, DMSO-$d_6$): δ 11.98 (s, 1H), 8.70 (s, 1H), 8.16 (d, J=8.8 Hz, 1H), 7.62-7.58 (m, 3H), 7.32 (dd, J=8.4, 1.2 Hz, 1H), 7.17 (d, J=2.0 Hz, 1H), 6.90 (dd, J=8.8, 2.4 Hz, 1H), 4.42 (t, J=5.6 Hz, 2H), 3.83 (s, 3H), 3.70 (t, J=5.6 Hz, 2H), 3.40 (q, J=7.2 Hz, 2H), 2.43 (s, 3H), 1.02 (t, J=7.2 Hz, 3H); $^{13}C$ NMR (100 MHz, DMSO-$d_6$): δ 156.75, 154.17. 152.85, 148.39, 142.91, 136.73, 132.91, 128.33, 127.54, 127.15, 122.24, 122.16, 117.27, 111.37, 111.24, 110.03, 107.62, 94.53, 67.88, 65.62, 55.44, 43.41, 20.83, 14.97; HRMS (TOF MS $ES^-$): m/z calcd for $C_{24}H_{23}ClN_3O_4$ $(M-H)^-$ 452.1377, found 452.1372; mp 210° C.

Example 10: Preparation of (E)-N'-[(2-chloro-1-(2-ethoxyethyl)-5-fluoro-1H-indol-3-yl]methylene}-5-methylbenzofuran-2-carbohydrazide

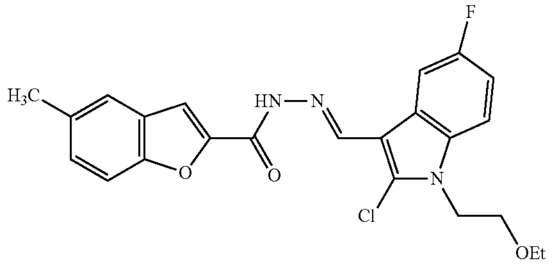

To 5-methylbenzofuran-2-carbohydrazide (66.6 mg, 0.35 mmol) and 2-chloro-1-(2-ethoxyethyl)-5-fluoro-1H-indol-3-carboxaldehyde (94.4 mg, 0.35 mmol), 1-PrOH (10 mL) and acetic acid (1-2 drops) were added and refluxed for 8 hours. The reaction solution was distilled under reduced pressure, dissolved in a small amount of $CH_2Cl_2$, and then added dropwise to n-Hex solution. The resulting solid was filtered to obtain 137 mg of the title compound (yield 89%, white solid).

$^1H$ NMR (400 MHz, DMSO-$d_6$): δ 12.06 (s, 1H), 8.73 (s, 1H), 8.02 (dd, J=9.6, 2.8 Hz, 1H), 7.67 (dd, J=9.2, 4.8 Hz, 1H), 7.63-7.58 (m, 3H), 7.32 (d, J=9.6 Hz, 1H), 7.18 (m, 1H), 4.47 (t, J=5.6 Hz, 2H), 3.69 (t, J=5.6 Hz, 2H), 3.38 (q, J=6.8 Hz, 2H), 2.43 (s, 3H), 0.99 (t, J=6.8 Hz, 3H); $^{13}C$ NMR (100 MHz, DMSO-$d_6$): δ 158.31 (d, J=233.8 Hz), 154.27, 152.88, 148.31, 142.49, 132.93, 132.47, 130.35, 128.37, 127.14, 123.65 (d, J=11.3 Hz), 122.24, 112.30 (d, J=9.4 Hz), 111.36, 111.21 (d, J=25.9 Hz), 110.19, 107.65 (d, J=4.4 Hz), 106.37 (d, J=25.1 Hz), 67.88, 65.64, 43.85, 20.82, 14.88; $^{19}F$ NMR (376 MHz, DMSO-$d_6$): δ-121.3 (s, 1F); HRMS (TOF MS $ES^-$): m/z calcd for $C_{23}H_{20}ClFN_3O_3$ $(M-H)^-$ 440.1177, found 440.1185; mp 187° C.

Example 11: Preparation of (E)-N'-[(2,5-dichloro-1-(2-ethoxyethyl)-1H-indol-3-yl]methylene}-5-methylbenzofuran-2-carbohydrazide

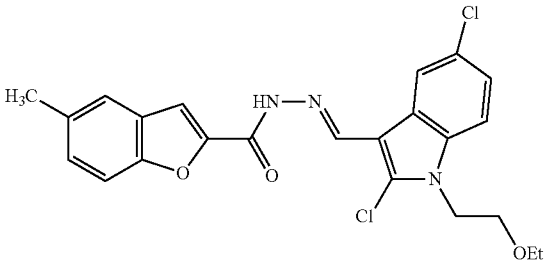 [SMILES: CCOCCn1c(Cl)c(/C=N/NC(=O)c2cc3cc(C)ccc3o2)c2cc(F)ccc21]

To 5-methylbenzofuran-2-carbohydrazide (165.5 mg, 0.87 mmol) and 2,5-dichloro-1-(2-ethoxyethyl)-1H-indol-3-carboxaldehyde (249.0 mg, 0.87 mmol), 1-PrOH (30 mL) and acetic acid (1-2 drops) were added and refluxed for 3 hours. The reaction solution was distilled under reduced pressure and recrystallized from EtOH. The resulting solid was filtered and washed with cold EtOH to obtain 270 mg of the title compound (yield 68%, white solid).

$^{1}$H NMR (400 MHz, DMSO-$d_6$) δ 12.07 (s, 1H), 8.73 (s, 1H), 8.32 (s, 1H), 7.67 (d, J=8.8 Hz, 1H), 7.63-7.58 (m, 3H), 7.35-7.31 (m, 2H), 4.46 (t, J=5.0 Hz, 2H), 3.69 (t, J=5.0 Hz, 2H), 3.38 (q, J=7.0 Hz, 2H), 2.43 (s, 3H), 0.98 (t, J=7.0 Hz, 3H); $^{13}$C NMR (100 MHz, DMSO-$d_6$): δ 154.31, 152.92, 148.30, 142.52, 134.40, 132.98, 130.52, 128.44, 127.17, 126.42, 124.25, 123.16, 122.30, 120.44, 112.65, 111.42, 110.30, 107.33, 67.89, 65.68, 43.88, 20.88, 14.93; HRMS (ESI): m/z calcd for $C_{23}H_{22}Cl_2N_3O_3$ $(M+H)^+$ 458.1038, found 458.1037; mp 98° C.

Example 12: Preparation of (E)-N'-[(2-chloro-1-(2-ethoxyethyl)-5-(trifluoromethoxy)-1H-indol-3-yl]methylene}-5-methylbenzofuran-2-carbohydrazide

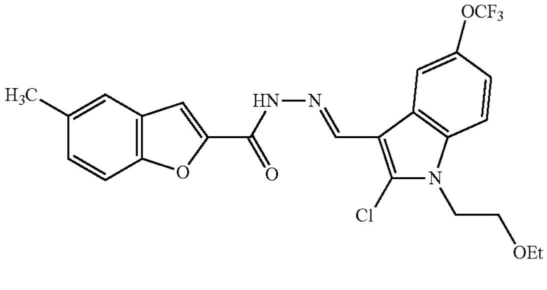 [SMILES: CCOCCn1c(Cl)c(/C=N/NC(=O)c2cc3cc(C)ccc3o2)c2cc(OC(F)(F)F)ccc21]

To 5-methylbenzofuran-2-carbohydrazide (22.8 mg, 0.12 mmol) and 2-chloro-1-(2-ethoxyethyl)-5-trifluoromethoxy-1H-indol-3-carboxaldehyde (40.3 mg, 0.12 mmol), 1-PrOH (10 mL) and acetic acid (1-2 drops) were added and refluxed for 18 hours. The reaction solution was distilled under reduced pressure, and the residue was separated by column chromatography (n-Hex:EA=1:2) to obtain 52 mg of the title compound (yield 85%, pale yellow solid).

$^{1}$H NMR (400 MHz, DMSO-$d_6$) δ 12.10 (s, 1H), 8.75 (s, 1H), 8.26 (s, 1H), 7.45 (d, J=9.2 Hz, 1H), 7.63-7.58 (m, 3H), 7.33-7.29 (m, 2H), 4.49 (t, J=5.2 Hz, 2H), 3.71 (t, J=5.2 Hz, 2H), 3.39 (q, J=7.2 Hz, 2H), 2.43 (s, 3H), 0.99 (t, J=7.2 Hz, 3H); $^{13}$C NMR (100 MHz, DMSO-$d_6$): δ 154.27, 152.88, 148.29, 143.57, 142.30, 134.32, 132.95, 130.87, 128.41, 127.13, 123.45, 122.27, 120.34 (q, J=253.9 Hz), 116.68, 113.47, 112.43, 111.37, 110.27, 107.92, 67.84, 65.63, 43.93, 20.83, 14.87; $^{19}$F NMR (376 MHz, DMSO-$d_6$): δ −56.8 (s, 3F); HRMS (TOF MS $ES^-$): m/z calcd for $C_{24}H_{20}ClF_3N_3O_4$ $(M-H)^-$ 506.1094, found 506.1087; mp 84-85° C.

Example 13: Preparation of (E)-N'-[(2-chloro-1-(2-ethoxyethyl)-5-methyl-1H-indol-3-yl]methylene}-5-methylbenzofuran-2-carbohydrazide

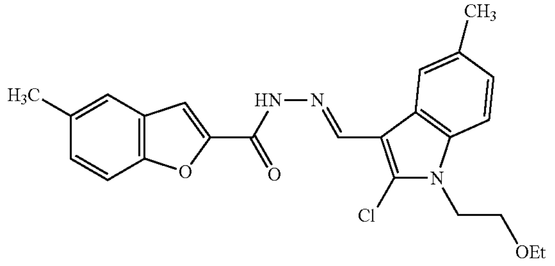 [SMILES: CCOCCn1c(Cl)c(/C=N/NC(=O)c2cc3cc(C)ccc3o2)c2cc(C)ccc21]

To 5-methylbenzofuran-2-carbohydrazide (374.7 mg, 1.97 mmol) and 2-chloro-1-(2-ethoxyethyl)-5-methyl-1H-indol-3-carboxaldehyde (523.5 mg, 1.97 mmol), 1-PrOH (30 mL) and acetic acid (1-2 drops) were added and heated to reflux for 3 hours. The reaction solution was distilled under reduced pressure and recrystallized from EtOH. The resulting solid was filtered and washed with cold EtOH to obtain 690 mg of the title compound (yield 80%, pale yellow solid).

$^{1}$H NMR (400 MHz, DMSO-$d_6$): δ 11.99 (s, 1H), 8.75 (s, 1H), 8.11 (s, 1H), 7.63-7.59 (m, 3H), 7.50 (d, J=8.4 Hz, 1H), 7.33 (dd, J=8.4, 1.4 Hz, 1H), 7.14 (dd, J=8.4, 1.4 Hz, 1H), 4.43 (t, J=5.4 Hz, 2H), 3.69 (t, J=5.4 Hz, 2H), 3.39 (q, J=7.0 Hz, 2H), 2.45 (s, 3H), 2.44 (s, 3H), 1.01 (t, J=7.0 Hz, 3H); $^{13}$C NMR (100 MHz, DMSO-$d_6$): δ 154.21, 152.90, 148.46, 143.38, 134.16, 132.95, 130.58, 129.22, 128.37, 127.20, 124.64, 123.54, 122.28, 121.08, 111.41, 110.42, 110.10, 107.09, 67.90, 65.66, 43.57, 21.34, 20.88, 14.95; HRMS (TOF MS $ES^-$): m/z calcd for $C_{24}H_{23}ClN_3O_3$ $(M-H)^-$ 436.1428, found 436.1442; mp 197° C.

Example 14: Preparation of (E)-N'-[(2-chloro-1-(2-ethoxyethyl)-1H-indol-3-yl]methylene}-5-methoxybenzofuran-2-carbohydrazide

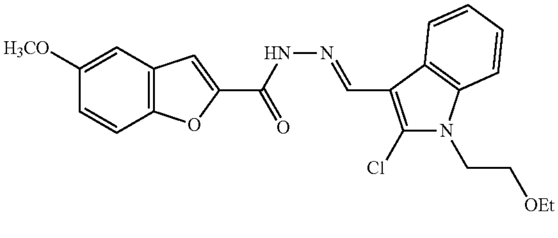 [SMILES: CCOCCn1c(Cl)c(/C=N/NC(=O)c2cc3cc(OC)ccc3o2)c2ccccc21]

To 5-methoxybenzofuran-2-carbohydrazide (103.1 mg, 0.50 mmol) and 2-chloro-1-(2-ethoxyethyl)-1H-indol-3-carboxaldehyde (125.9 mg, 0.50 mmol), 1-PrOH (15 mL) and acetic acid (1-2 drops) were added and refluxed for 7 hours. The reaction solution was distilled under reduced pressure, and the residue was washed with a mixed solvent of n-Hex/$CH_2Cl_2$ (1:1) to obtain 204 mg of the title compound (yield 93%, pale yellow solid).

$^1$H NMR (400 MHz, DMSO-$d_6$): δ 12.01 (s, 1H), 8.75 (s, 1H), 8.32 (d, J=7.6 Hz, 1H), 7.63-7.60 (m, 3H), 7.33-7.24 (m, 3H), 7.10 (dd, J=8.8, 2.4 Hz, 1H), 4.46 (t, J=5.6 Hz, 2H), 3.82 (s, 3H), 3.70 (t, J=5.6 Hz, 2H), 3.39 (q, J=7.2 Hz, 2H), 1.00 (t, J=7.2 Hz, 3H); $^{13}$C NMR (100 MHz, DMSO-$d_6$): δ 156.11, 154.16, 149.34, 148.94, 143.01, 135.76, 129.27, 127.72, 123.35, 123.21, 121.68, 121.43, 116.39, 112.47, 110.68, 110.43, 107.53, 104.20, 67.85, 65.63, 55.63, 43.53, 14.90; HRMS (TOF MS $ES^-$): m/z calcd for $C_{23}H_{21}ClN_3O_4$ $(M-H)^-$ 438.1221, found 438.1218; mp 185° C.

Example 15: Preparation of (E)-N'-[(2-chloro-1-(2-ethoxyethyl)-5-methoxy-1H-indol-3-yl]methylene}-5-methoxybenzofuran-2-carbohydrazide

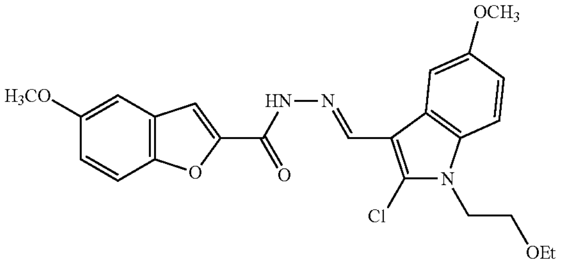 [SMILES: CCOCCn1c(Cl)c(/C=N/NC(=O)c2cc3cc(OC)ccc3o2)c2cc(OC)ccc21]

To 5-methoxybenzofuran-2-carbohydrazide (103.1 mg, 0.50 mmol) and 2-chloro-1-(2-ethoxyethyl)-5-methoxy-1H-indol-3-carboxaldehyde (140.9 mg, 0.50 mmol), 1-PrOH (15 mL) and acetic acid (1-2 drops) were added and refluxed for 8 hours. The reaction solution was distilled under reduced pressure, and the residue was separated by column chromatography (n-Hex:EA=2:3) to obtain 222 mg of the title compound (yield 94%, pale yellow solid).

$^1$H NMR (400 MHz, DMSO-$d_6$): δ 12.01 (s, 1H), 8.73 (s, 1H), 7.91 (d, J=2.4 Hz, 1H), 7.62-7.59 (m, 2H), 7.52 (d, J=8.8 Hz, 1H), 7.32 (d, J=2.4 Hz, 1H), 7.09 (dd, J=8.8, 2.4 Hz, 1H), 6.95 (dd, J=8.8, 2.4 Hz, 1H), 4.42 (t, J=5.2 Hz, 2H), 3.82 (s, 3H), 3.817 (s, 3H), 3.68 (t, J=5.2 Hz, 2H), 3.38 (q, J=7.2 Hz, 2H), 1.00 (t, J=7.2 Hz, 3H); $^{13}$C NMR (100 MHz, DMSO-$d_6$): δ 156.11, 155.21, 154.12, 149.33, 149.03, 142.97, 130.75, 128.96, 127.74, 124.02, 116.37, 112.45, 112.27, 111.54, 110.42, 107.25, 104.20, 104.09, 67.92, 65.63, 55.63, 55.33, 43.67, 14.91; HRMS (TOF MS $ES^-$): m/z calcd for $C_{24}H_{23}ClN_3O_5(M-H)^-$ 468.1326, found 468.1322; mp 128-129° C.

Example 16: Preparation of (E)-5-chloro-N'-{[2-chloro-1-(2-ethoxyethyl)-1H-indol-3-yl] methylene}benzofuran-2-carbohydrazide

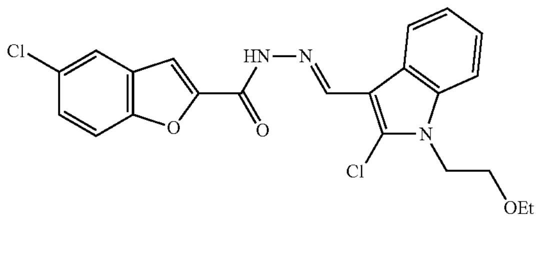 [SMILES: CCOCCn1c(Cl)c(/C=N/NC(=O)c2cc3cc(Cl)ccc3o2)c2ccccc21]

To 5-chlorobenzofuran-2-carbohydrazide (103.2 mg, 0.49 mmol) and 2-chloro-1-(2-ethoxyethyl)-1H-indol-3-carboxaldehyde (123.3 mg, 0.49 mmol), 1-PrOH (15 mL) and acetic acid (1-2 drops) were added and refluxed for 24 hours. The reaction solution was distilled under reduced pressure, and the residue was separated by column chromatography ($CH_2Cl_2$:EA=5:1) to obtain 188 mg of the title compound (yield 86%, pale yellow solid).

$^1$H NMR (400 MHz, DMSO-$d_6$) δ 12.10 (s, 1H), 8.75 (s, 1H), 8.32 (d, J=7.6 Hz, 1H), 7.94 (d, J=2.0 Hz, 1H), 7.76 (d, J=9.2 Hz, 1H), 7.69 (s, 1H), 7.61 (d, J=7.6 Hz, 1H), 7.53 (dd, J=9.2, 2.0 Hz, 1H), 7.33-7.24 (m, 2H), 4.46 (t, J=5.2 Hz, 2H), 3.70 (t, J=5.2 Hz, 2H), 3.39 (q, J=7.2 Hz, 2H), 1.00 (t, J=7.2 Hz, 3H); $^{13}$C NMR (100 MHz, DMSO-$d_6$): δ 153.79, 152.86, 149.68, 143.29, 135.76, 129.43, 128.66, 128.15, 126.97, 123.33, 123.23, 122.21, 121.72, 121.39, 113.52, 110.71, 109.75, 107.44, 67.84, 65.63, 43.55, 14.90; HRMS (ESI): m/z calcd for $C_{22}H_{20}Cl_2N_3O_3$ $(M+H)^+$ 444.0882, found 444.0884; mp 117° C.

Example 17: Preparation of (E)-N'-[(2-chloro-1-(2-ethoxyethyl)-1H-indol-3-yl]methylene}-4,7-dimethylbenzofuran-2-carbohydrazide

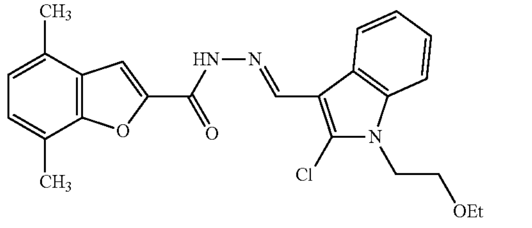 [SMILES: CCOCCn1c(Cl)c(/C=N/NC(=O)c2cc3c(C)ccc(C)c3o2)c2ccccc21]

To 4,7-dimethylbenzofuran-2-carbohydrazide (81.7 mg, 0.40 mmol) and 2-chloro-1-(2-ethoxyethyl)-1H-indol-3-carboxaldehyde (100.7 mg, 0.40 mmol), 1-PrOH (15 mL) and acetic acid (1-2 drops) were added and refluxed for 24 hours. The reaction solution was distilled under reduced pressure and separated by column chromatography ($CH_2Cl_2$:EA=5:1) to obtain 158 mg of the title compound (yield 90%, white solid).

$^1$H NMR (400 MHz, DMSO-$d_6$) δ 11.87 (s, 1H), 8.76 (s, 1H), 8.34 (d, J=7.2 Hz, 1H), 7.76 (s, 1H), 7.61 (d, J=8.0 Hz, 1H), 7.34-7.25 (m, 2H), 7.19 (d, J=8.0 Hz, 1H), 7.05 (d, J=7.2 Hz, 1H), 4.46 (t, J=5.6 Hz, 2H), 3.71 (t, J=5.6 Hz, 2H), 3.39 (q, J=7.2 Hz, 2H), 2.54 (s, 3H), 2.51 (s, 3H), 1.00 (t, J=7.2 Hz, 3H); $^{13}$C NMR (100 MHz, DMSO-$d_6$): δ 154.34, 153.35, 147.46, 142.86, 135.76, 129.60, 129.25, 127.53, 126.50, 123.81, 123.35, 123.22, 121.67, 121.42, 118.71, 110.69, 109.48, 107.50, 67.85, 65.62, 43.53, 17.88, 14.90, 14.52; HRMS (ESI): m/z calcd for $C_{24}H_{25}ClN_3O_3$ $(M+H)^+$ 438.1584, found 438.1584; mp 202° C.

Example 18: Preparation of (E)-N'-[(2-chloro-1-(2-ethoxyethyl)-1H-indol-3-yl]methylene}-4,6-dimethoxybenzofuran-2-carbohydrazide

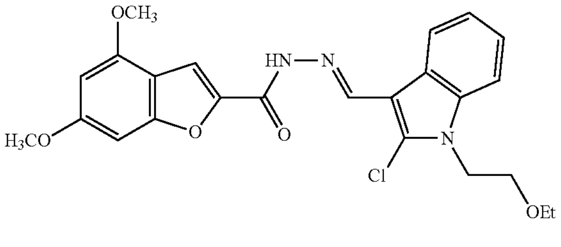 [SMILES: CCOCCn1c(Cl)c(/C=N/NC(=O)c2cc3c(OC)cc(OC)cc3o2)c2ccccc21]

To 4,6-dimethoxybenzofuran-2-carbohydrazide (118.1 mg, 0.50 mmol) and 2-chloro-1-(2-ethoxyethyl)-1H-indol-3-carboxaldehyde (125.9 mg, 0.50 mmol), 1-PrOH (15 mL) and acetic acid (1-2 drops) were added and refluxed for 4 hours. The reaction solution was cooled, and the solid was filtered and washed with EtOH to obtain 210 mg of the title compound (yield 89%, white solid).

$^1H$ NMR (400 MHz, DMSO-$d_6$) δ 11.82 (s, 1H), 8.69 (s, 1H), 8.32 (d, J=7.6 Hz, 1H), 7.63 (s, 1H), 7.60 (d, J=7.6 Hz, 1H), 7.33-7.23 (m, 2H), 6.87 (s, 1H), 6.50 (d, J=2.0 Hz, 1H), 4.45 (t, J=5.6 Hz, 2H), 3.92 (s, 3H), 3.85 (s, 3H), 3.70 (t, J=5.6 Hz, 2H), 3.38 (q, J=7.2 Hz, 2H), 1.00 (t, J=7.2 Hz, 3H); $^{13}C$ NMR (100 MHz, DMSO-$d_6$): δ 161.07, 156.44, 154.11, 146.03, 142.31, 135.74, 129.04, 123.33, 123.18, 121.60, 121.41, 110.98, 110.65, 107.58, 107.53, 95.13, 88.44, 67.85, 65.62, 55.84, 43.50, 14.90; HRMS (ESI): m/z calcd for $C_{24}H_{25}ClN_3O_5(M+H)^+$ 470.1483, found 470.1482; mp 215° C.

Example 19: Preparation of (E)-N'-{2-[2-((2-chloro-1-(2-ethoxyethyl)-1H-indol-3-yl)methylene]hydrazine-1-carbonyl}benzofuran-5-yl)acetamide

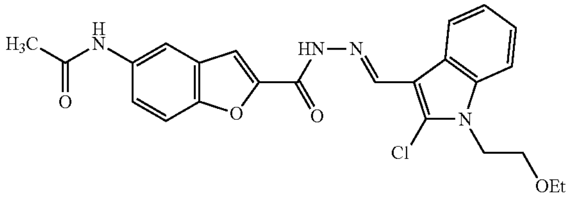 [SMILES: CCOCCn1c(Cl)c(/C=N/NC(=O)c2cc3cc(NC(C)=O)ccc3o2)c2ccccc21]

To N-((2-hydrazinecarbonyl)benzofuran-5-yl)acetamide (116.6 mg, 0.50 mmol) and 2-chloro-1-(2-ethoxyethyl)-1H-indol-3-carboxaldehyde (125.9 mg, 0.50 mmol), 1-PrOH (20 mL) and acetic acid (1-2 drops) were added and refluxed for 12 hours. The reaction solution was cooled, and the solid was filtered and washed with EtOH to obtain 166 mg of the title compound (yield 71|[Yon Yang6], pale yellow solid).

$^1H$ NMR (400 MHz, DMSO-$d_6$) δ 12.02 (s, 1H), 10.07 (s, 1H), 8.76 (s, 1H), 8.32 (d, J=7.2 Hz, 1H), 8.17 (d, J=2.4 Hz, 1H), 7.68 (s, 1H), 7.65-7.60 (m, 2H), 7.53 (dd, J=9.2, 2.4 Hz, 1H), 7.33-7.24 (m, 2H), 4.46 (t, J=5.6 Hz, 2H), 3.70 (t, J=5.6 Hz, 2H), 3.39 (q, J=7.2 Hz, 2H), 2.08 (s, 3H), 1.00 (t, J=7.2 Hz, 3H); $^{13}C$ NMR (100 MHz, DMSO-$d_6$): δ 168.24, 154.15, 150.62, 148.84, 143.08, 135.77, 135.54, 129.32, 127.18, 123.36, 123.24, 121.70, 121.44, 119.61, 112.10, 111.83, 110.72, 110.66, 107.53, 67.88, 65.65, 43.55, 23.97, 14.94; HRMS (TOF MS $ES^-$) m/z calcd for $C_{24}H_{22}ClN_4O_4$ $(M-H)^-$ 465.1330, found 465.1323; mp 226° C.

Example 20: Preparation of (E)-ethyl-2-(3-((2-(4,6-dimethoxybenzofuran-2-carbonyl) hydrazinylidene) methyl)-2-methyl-1H-indol-1-yl)acetate

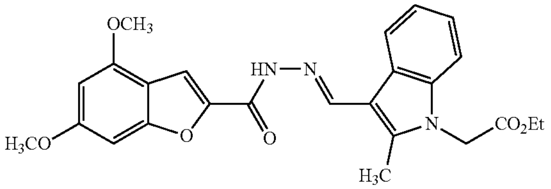 [SMILES: CCOC(=O)Cn1c(C)c(/C=N/NC(=O)c2cc3c(OC)cc(OC)cc3o2)c2ccccc21]

To 4,6-dimethoxybenzofuran-2-carbohydrazide (118.1 mg, 0.50 mmol) and ethyl 2-(3-formyl-2-methyl-1H-indol-1-yl)acetate (122.6 mg, 0.50 mmol), 1-PrOH (15 mL) and acetic acid (1-2 drops) were added and refluxed for 4 hours. The reaction solution was cooled, and the solid was filtered and washed with EtOH to obtain 197 mg of the title compound (yield 85%, white solid).

HRMS (ESI): m/z calcd for $C_{25}H_{25}N_3O_6Na$ (M+Na) 486.1641, found 486.1642.

Comparative Example 1: Preparation of (E)-ethyl 2-(2-methyl-3-((2-(naphtho[2,1-b]furan-2-carbonyl) hydrazono)methyl)-1H-indol-1-yl)acetate

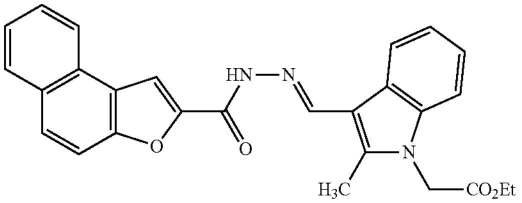 [SMILES: CCOC(=O)Cn1c(C)c(/C=N/NC(=O)c2cc3c(ccc4ccccc43)o2)c2ccccc21]

The title compound (yield 75%, light yellow solid) was obtained by the synthesis method disclosed in Korean Patent Laid-Open Publication No. 2014-0128238.

$^1H$ NMR (400 MHz, DMSO-d6) δppm: 11.838 (1H, s, —NHCO—), 8.862 (1H, s, —N═CH—Ar), 8.438-8.418 (1H, d, J=8, Ar—H), 8.355-8.307 (2H, dd, J=8.8, 3.6, Ar—H), 8.114-8.094 (1H, d, J=8.0, Ar—H), 8.041-8.018 (1H, d, J=8.0, Ar—H), 7.891-7.869 (1H, d, J=8.8, Ar—H), 7.731-7.694 (1H, t, J=7.2, Ar—H), 7.622-7.585 (1H, t, J=8.0, Ar—H), 7.483-7.461 (1H, t, J=8.8, Ar—H), 7.217-7.198 (2H, m, Ar—H), 5.192 (2H, s, —N—$CH_2$), 4.211-4.158 (2H, q, J=7.2, —O—$CH_2$), 2.505 (3H, s, —$CH_3$), 1.249-1.214 (3H, t, J=7.2, —$CH_3$); $^{13}C$ NMR (100 MHz, DMSO-$d_6$): δppm: 168.602, 153.88, 152.217, 148.131, 145.138, 141.430, 137.031, 130.101, 128.833, 128.178, 127.482, 127.271, 125.388, 124.674, 123.720, 122.755, 122.242, 121.368, 120.985, 112.485, 109.656, 109.539, 108.235, 61.201, 44.431, 14.026, 9.961. ESIMS found: m/z 452.6 $[M-H]^-$, 454.6 $[M+H]^+$, 476.5 $[M+Na]^+$; Rf=0.50 (n-Hex:EA=1:2) The following experiments were carried out on the Example compounds as prepared above.

Experimental Example 1: Anti-Proliferative Activity Test 1.1. Anti-Proliferative Activity Test in HeLa Cell Line The following experiments were carried out to test the anti-proliferative activity of the Example compounds according to the present invention.

HeLa cells (American Type Culture Collection: ATCC, USA), a human cervical cancer cell line, were seeded in a 96-well plate at $3\times10^3$ cells/well, and the cells were then treated with compounds of Examples or Comparative Example according to the present invention and grown for 2 days. Then, MTT (3-(4,5-dimethylthiazol-2-yl)-2,5-diphenyltetrazolium bromide) reagent was added at 10 μL/well. After 2 hours, absorbance was measured at "OD 450" and statistical values were obtained using Prism™6 program. The data shown in Table below are mean values of results obtained by repeating the analysis twice.

TABLE 1

| Material to be treated | $IC_{50}$ (nM) | Compound class |
|---|---|---|
| Control | — | DMSO |
| Example 1 | 3878.8 | Benzofuran |
| Example 2 | 892.3 | Benzofuran |
| Example 3 | 243.4 | Benzofuran |
| Example 4 | 180.0 | Benzofuran |
| Example 5 | 262.8 | Benzofuran |
| Example 6 | 1216.5 | Benzofuran |
| Example 7 | 232.8 | Benzofuran |
| Example 8 | 82.0 | Benzofuran |
| Example 9 | 232.1 | Benzofuran |
| Example 10 | 221.3 | Benzofuran |
| Example 11 | 242.6 | Benzofuran |
| Example 12 | 618.9 | Benzofuran |
| Example 13 | 337.0 | Benzofuran |
| Example 14 | 261.7 | Benzofuran |
| Example 15 | 123.2 | Benzofuran |
| Example 16 | 455.2 | Benzofuran |
| Example 18 | 563 (±37) | Benzofuran |
| Example 19 | 4524.3 | Benzofuran |
| Example 20 | 500 (±45) | Benzofuran |
| Comparative Example 1 | 562.3 | Naphthofuran |

As shown in Table above, it could be appreciated that the compounds of Examples according to the present invention had excellent anti-proliferative activity in the HeLa cell line (cervical cancer cell line).

1.2. Anti-Proliferative Activity Test in Other Cancer Cell Lines

The following experiment was performed to test whether the Example compound according to the present invention exhibited the anti-proliferative activity not only in the HeLa cell line (cervical cancer cell line) but also in other cancer cells.

Specifically, various cancer cell lines were cultured in a microtiter plate (1-$3\times10^3$ cells/well), treated with the compound of Example 4 according to the present invention, and cultured for 4 days. Cytotoxicity was tested by MTT assay in the same manner as in Experimental Example 1-1, and $IC_{50}$ was obtained by a log-dose response curve. The data shown in Table below are mean values of results obtained by repeating the analysis three times.

TABLE 2

| Cell Line Derived Tissue | Cell Line | $IC_{50}$ (μM)-Example 4 |
|---|---|---|
| Bone | U-2-OS | 0.42 ± 0.06 |
| Brain | A172 | 0.79 ± 0.09 |
| | SK-N-MC | 0.98 ± 0.11 |
| | U373MG | 0.36 ± 0.01 |
| Breast | HCC1954 | 0.41 ± 0.05 |
| | MDA-MB-468 | 0.69 ± 0.03 |
| CNS | SNB75 | 0.39 ± 0.03 |
| Colon | Colo 205 | 0.36 ± 0.49 |
| | HCT 116 | 0.45 ± 0.22 |
| | HCT-15 | 0.28 ± 0.07 |
| Kidney | 786-O | 0.13 ± 0.05 |
| | A498 | 0.17 ± 0.008 |
| Marrow (leukemia) | K562 | 0.47 ± 0.012 |
| | MOLT4 | 0.30 ± 0.01 |
| | RPMI-8226 | 0.52 ± 0.13 |
| Liver | Hep3B | 0.19 ± 0.05 |
| | A549 | 0.63 ± 0.12 |
| Lung | NCI-H125 | 0.37 ± 0.2 |
| | NCI-H1299 | 0.56 ± 0.15 |
| | NCI-H226 | 0.42 ± 0.06 |
| | NCI-H460 | 0.5 ± 0.09 |
| | NCI-H522 | 0.37 ± 0.13 |
| Peripheral blood | CCRF-CEM | 0.34 ± 0.02 |
| Prostate | DU145 | 0.49 ± 0.09 |
| | PC3 | 0.71 ± 0.18 |
| Skin | A431 | 0.22 ± 0.017 |
| | SK-MEL 5 | 0.46 ± 0.14 |
| Stomach | SNU 484 | 0.35 ± 0.07 |
| Cervix | HeLa CCL2 | 0.18 ± 0.004 |
| Normal cell | MEF (mouse) | 4.01 ± 4.58 |
| | HDF (human) | 27.0 ± 7.89 |

As shown in Table above, it could be appreciated that the Example compound according to the present invention had excellent anti-proliferative activity even in various cancer cell lines.

1.3. Anti-Proliferative Activity Test in Cancer Cells Exhibiting Multidrug Resistance The following experiment was performed to test whether the Example compound according to the present invention had an effect even on cancer cell lines exhibiting multidrug resistance.

Specifically, K562 and MCF7 (Bio Evaluation Center, Korea Research Institute of Bioscience and Biotechnology, Korea) and multidrug-resistant cell lines of each of these cell lines, i.e., K562/ADR and MCF7/ADR (Bio Evaluation Center, Korea Research Institute of Bioscience and Biotechnology, Korea), were cultured on microtiter plates (1-$3\times10^3$ cells/well). Thereafter, the cells were treated with the compound of Example 4 according to the present invention, taxol, doxorubicin, vinblastine or colchicine, and cultured for 4 days. Cytotoxicity was tested by MTT assay in the same manner as in Experimental Example 1-1, and $IC_{50}$ was obtained by a log-dose response curve (unit: nM). The data shown in Table below are mean values of results obtained by repeating the analysis three times.

The resistance factor of the cell line exhibiting multidrug resistance refers to a ratio of the $IC_{50}$ of the multidrug resistant cell line to the $IC_{50}$ of the non-resistant parent cell line.

TABLE 3

| $IC_{50}$ (nM) | Example 4 | Taxol | Doxorubicin | Vinblastine | Colchicine |
|---|---|---|---|---|---|
| K562 | 350 | 1.347 | 2.848 | 17.13 | 15.86 |
| K562/ADR | 200.8 | 699.9 | 2187 | 267.8 | 363.4 |
| Resistance Factor | 0.57 | 519.6 | 767.91 | 15.63 | 22.91 |

TABLE 4

| $IC_{50}$ (nM) | Example 4 | Taxol | Doxorubicin | Vinblastine | Colchicine |
|---|---|---|---|---|---|
| MCF7 | 822 | 2.345 | 15.38 | 5.275 | 2.71 |
| MCF7/ADR | 331.5 | 1028 | 2608 | 95.87 | 92.54 |
| Resistance Factor | 0.40 | 438.38 | 169.57 | 18.17 | 34.15 |

As shown in Table above, the multidrug-resistant cell line exhibited great resistance corresponding to tens to hundreds of times the resistance factor to the existing anticancer drugs. However, the Example compound according to the present invention had the resistance factor of 0.40 to 0.57, which indicated that the Example compound according to the present invention exhibited a stronger cytotoxic effect on cancer cell lines exhibiting multidrug resistance compared to the existing anticancer drugs.

Experimental Example 2: Effect Test on Cell Cycle Progression

The HeLa CCL2 cell line was cultured in a 12-well plate ($3\times10^4$ cells/well), treated with DMSO or the compound of Example 4 for 17 hours. Then, propidium iodine dye was added to stain the cell DNA, and the cells were measured using FACS. Table below showed the concentration at which cells were collected in the mitotic phase and the number of cells as a percentage.

TABLE 5

| Cell line | Effect (μM) (%, G2/M phase) |
|---|---|
| HeLa CCL2 | 0.2 (82.36) |

As shown in Table above, the compound of Example 4 showed an $IC_{50}$ value at 0.2 μM for HeLa CCL2 which is a representative cancer cell line. In particular, it was observed that 80% or more of the cells were stopped in the mitotic phase in 16 hours post treatment on the cells, which was expected to inhibit the polymerization reaction of tubulin, and this expectation was confirmed in Experimental Example 3.

Experimental Example 3: Effect Test on Tubulin Polymerization

In order to confirm the effect of the Example compound according to the present invention on intracellular microtubules, HeLa cells were treated with DMSO or the compound of Example 4 (50 nM, 100 nM, and 200 nM) for 16 hours.

The cells were immobilized and stained with an anti-tubulin antibody and Alexa Fluor™ 488, and nuclei of the cells were subjected to immunostaining using Hoechst 33342 to test α-tubulin and DNA. As shown in FIG. 1, when treated with the Example compound according to the present invention compared to the DMSO control group, the shape of tubulin became coarser and shortened as the concentration increased. In addition, the DNA morphology deviating from the central alignment was also increased.

Therefore, it could be appreciated that the Example compound according to the present invention is an agent for depolymerizing microtubules.

Experimental Example 4: Anticancer Effect Test in Human Cervical Cancer Cell (HeLa CCL2) Transplantation Model 4.1. Cancer Cell Culture and Cancer Cell Transplantation After thawing the human skin cancer cell line HeLa CCL2 that was stored frozen in liquid nitrogen, cell culture was performed. The cells were cultured for an appropriate period in a $CO_2$ incubator (Forma, USA) at a temperature of 37° C. and a $CO_2$ concentration of 5%.

On the last day of culture, all cancer cells were collected and counted, and the cell concentration was adjusted to $1\times10^7$ cells/mL using serum free media. The cell culture solution as adjusted above was injected subcutaneously into the axillary region between the shoulder blade and the chest wall in an amount of 0.3 mL ($3\times10^6$ cells/mouse) per BALB/C female nude mouse (5 weeks old, Nara Biotech).

4.2. Preparation and Administration Method of Samples

Example compounds according to the present invention were used as test substances, and solvents (carriers) were used as negative controls.

Immediately prior to administration, the compounds were dissolved in a mixture of DMAC (dimethylacetamide) 20%+ Tween80 5%+20% HPbCD (2-hydroxypropyl-β-cyclodextrin) 75% at an appropriate concentration and used. The prepared substances were repeatedly administered intraperitoneally in an amount of 0.2 mL (10 mL/kg) per 20 g of a mouse according to the following administration schedule.

carrier, the compound of Example 4, the compound of Example 8, and the compound of Example 15 (25 mg/kg), 0-28 days 4.3. Confirmation of Change in Tumor Size After cancer cell transplantation, the tumor size of each animal subject was measured a total of 11 times in 3 directions using a vernier caliper from when the mean tumor size reached 57.0 $mm^3$ until Day 28, and calculated by the formula of length×width×height/2.

Figure 2A:
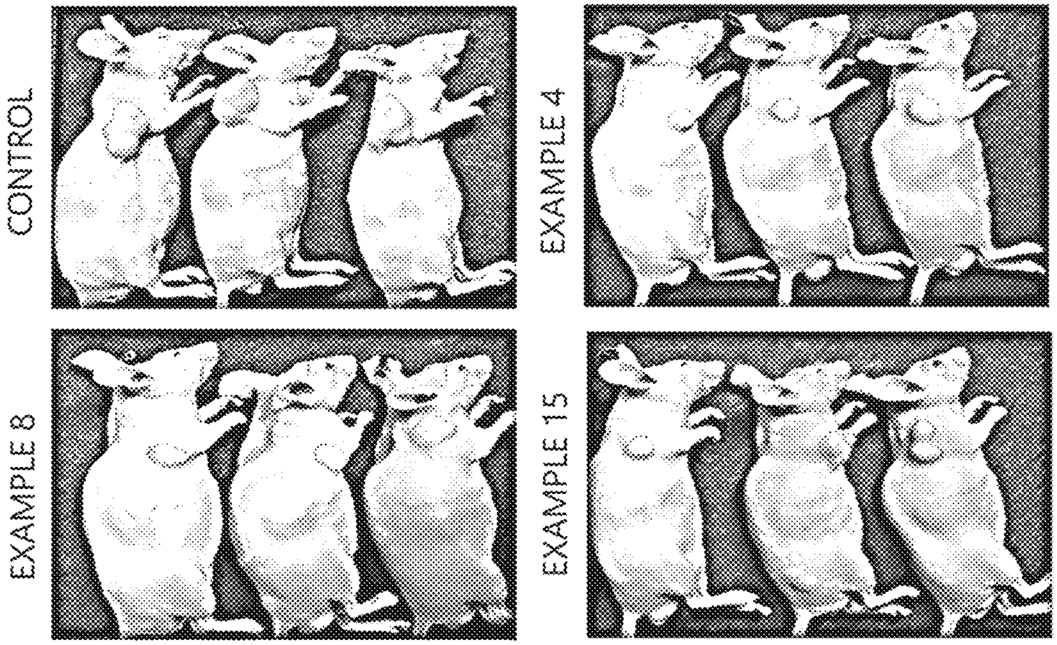
FIGS. 2A to 2E show results of anticancer effect tests in human cervical cancer cell (HeLa CCL2) transplantation models of the Example compounds according to the present invention.
Figure 2B:
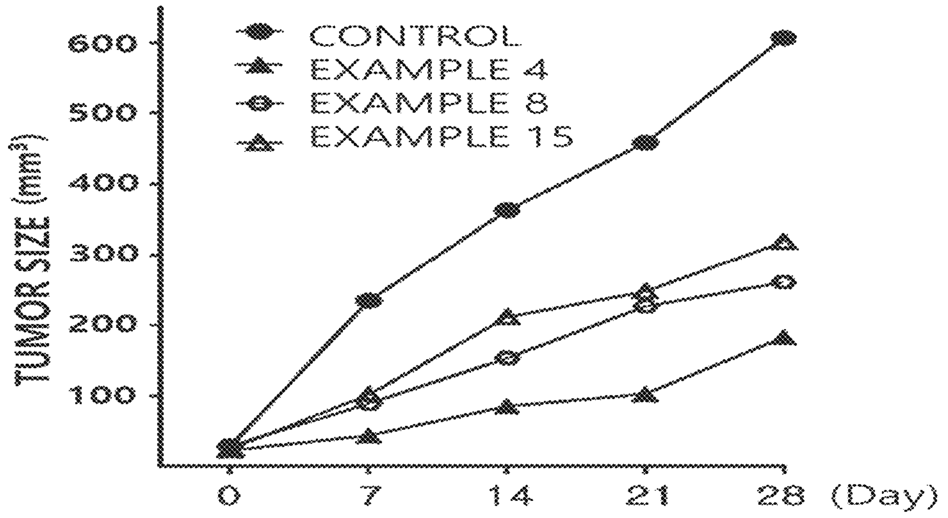

Referring to the results of the last day (Day 28), when the tumor growth inhibition of the control group was 0%, tumor growth inhibition of 56.71%, 38.35% and 40.13% ($p<0.001$) was observed in groups administered with the compounds of Examples 4, 8 and 15 (25 mg/kg), respectively (see FIGS. 2A and 2B).

4.4 Confirmation of General Symptoms and Weight Change

In order to test the degree of toxicity upon repeated intraperitoneal administration of the Example compound to HeLa CCL2 cancer cell transplantation nude mice, general symptoms and body weight changes of the animal subjects were observed during the administration period.

Figure 2C:
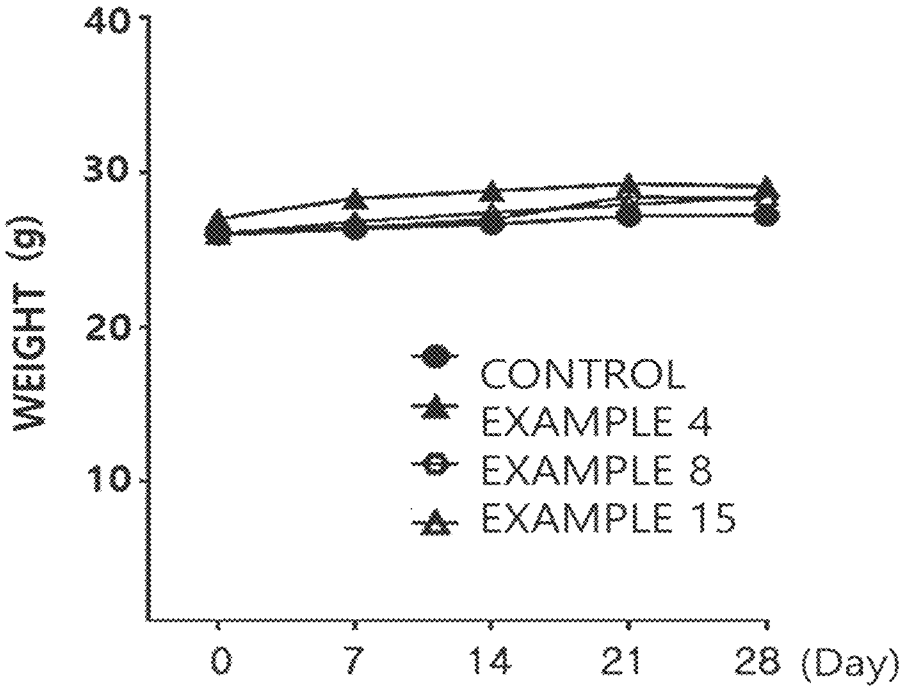

As a result, when compared to the solvent control group during the test period, statistically significant weight loss was not observed and there were no specific general symptoms in all drug administration groups (see FIG. 2C).

4.5. Confirmation of Change in Tumor Weight

On Day 28 after drug administration, blood was collected from the mouse ophthalmic veins in 2 hours post the last administration, and the mice were killed using $CO_2$ gas. Images of the mice were taken, and the tumor was separated and weighed on an electronic scale. After taking the images, each tumor was divided in half and fixed in liquid nitrogen and formalin, respectively. On Day 16 after drug administration, the HeLa CCL2 tumor was excised and weighed.

Figure 2D:
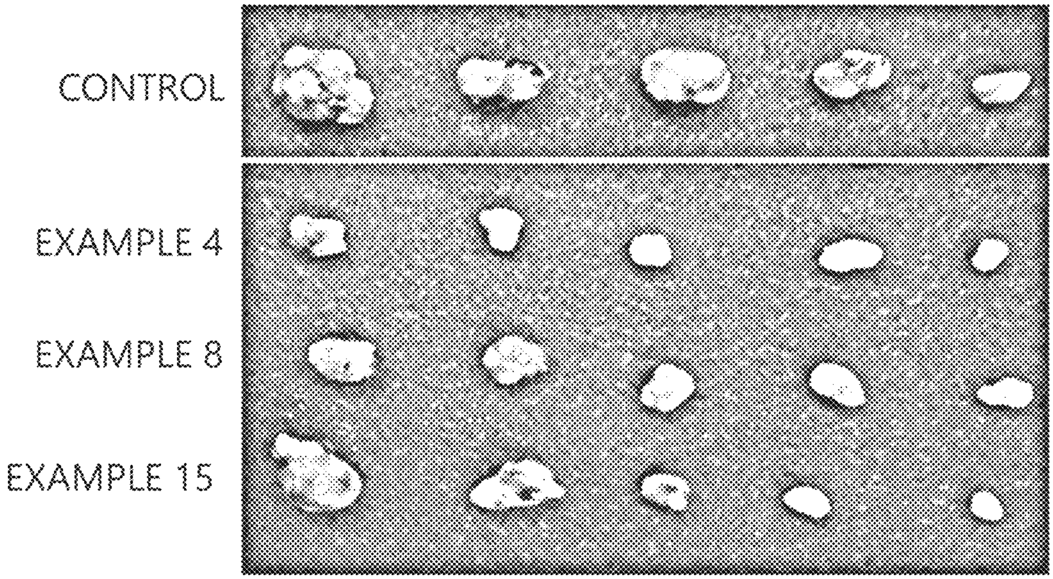
Figure 2E:
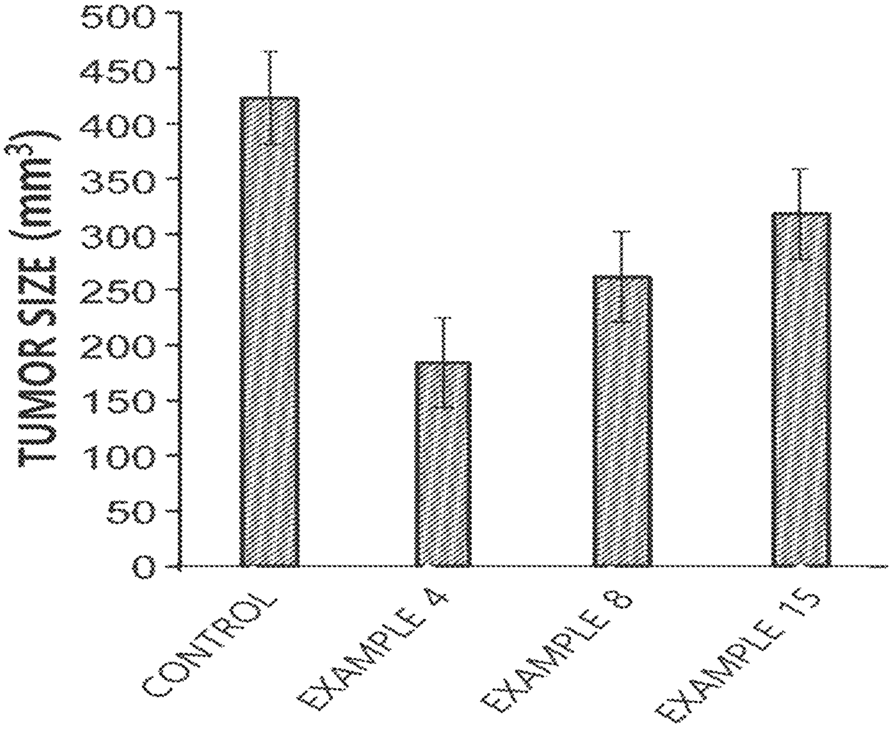
Figure 3A:
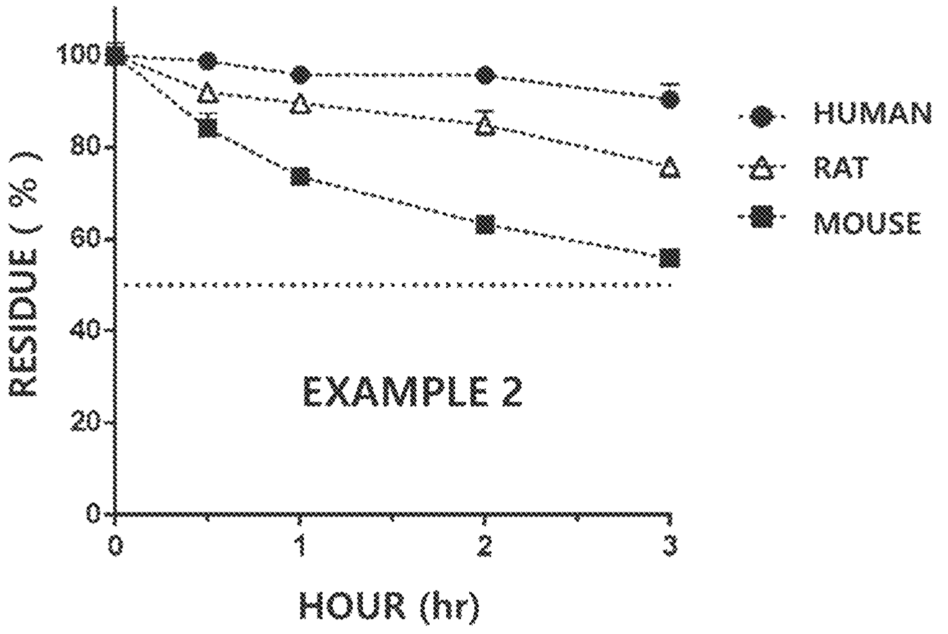
FIGS. 3A to 3E show results of stability tests in plasma of the Example compounds according to the present invention.
Figure 3B:
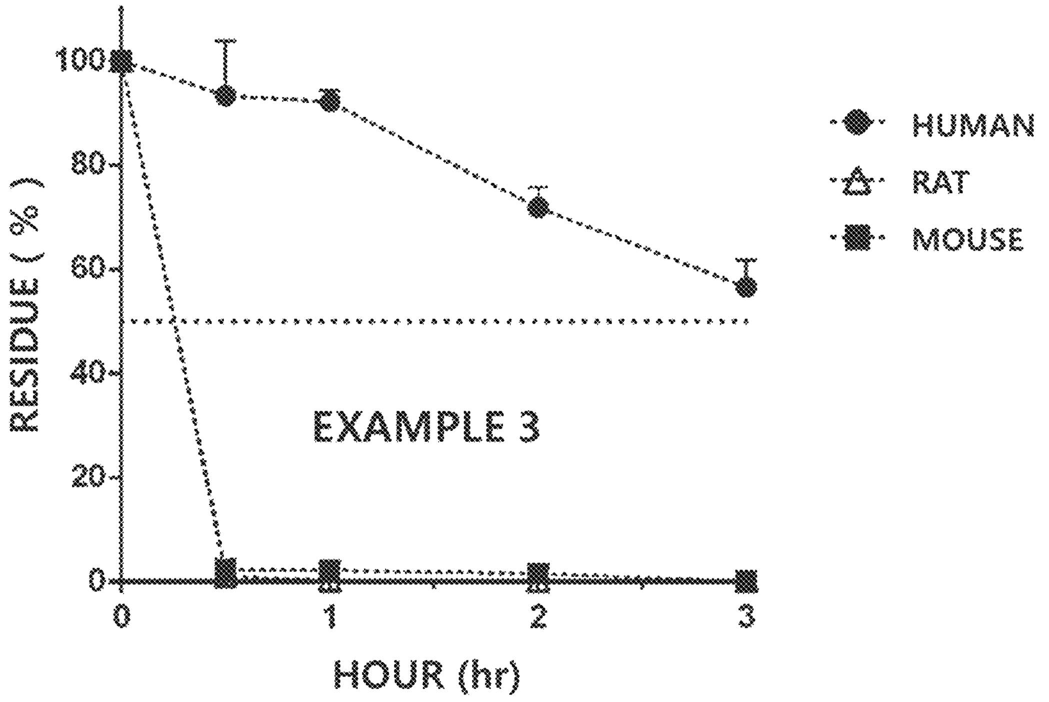
Figure 3C:
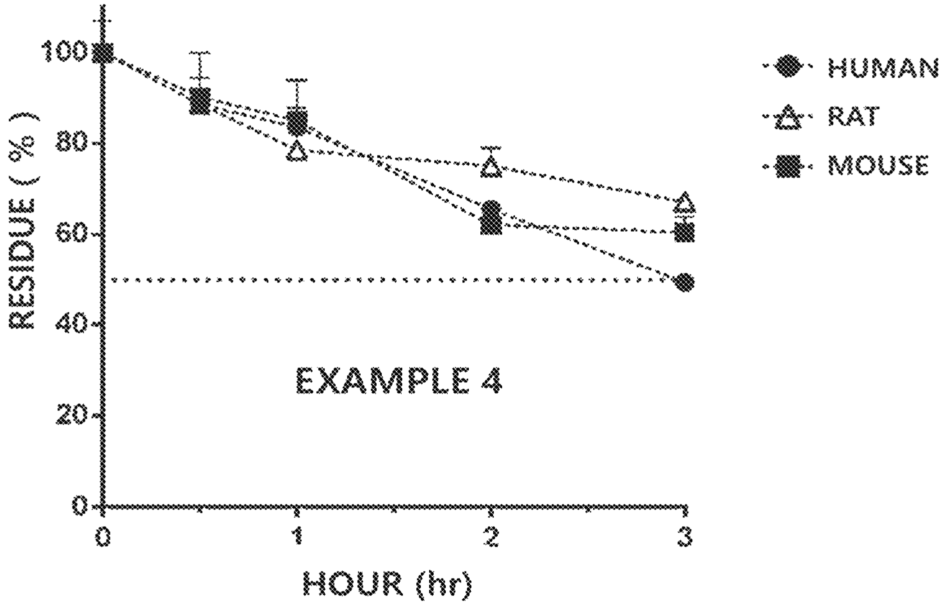
Figure 3D:
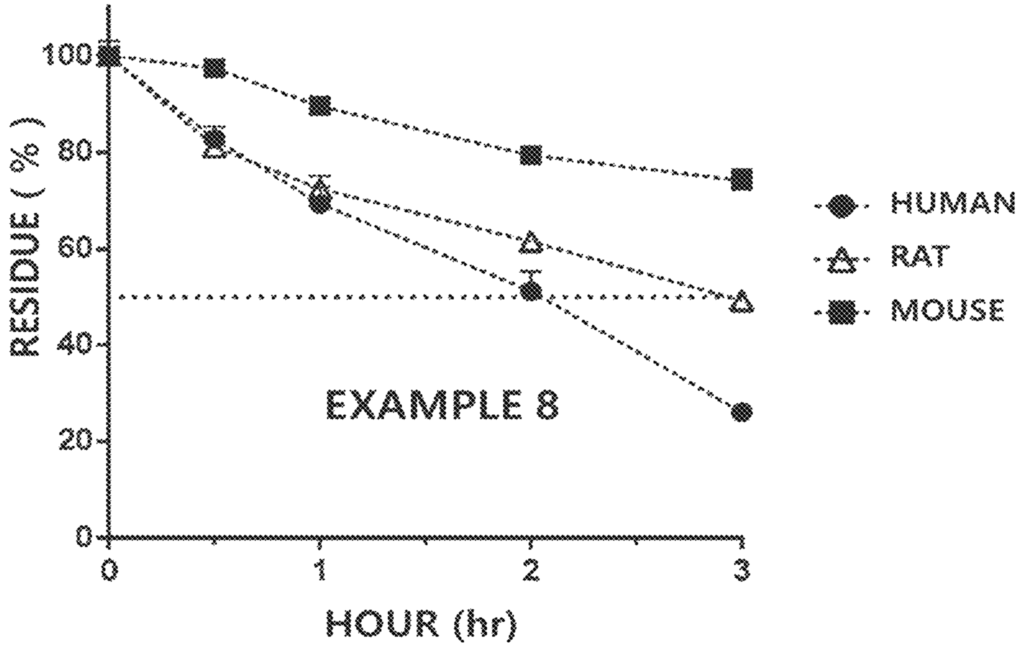
Figure 3E:
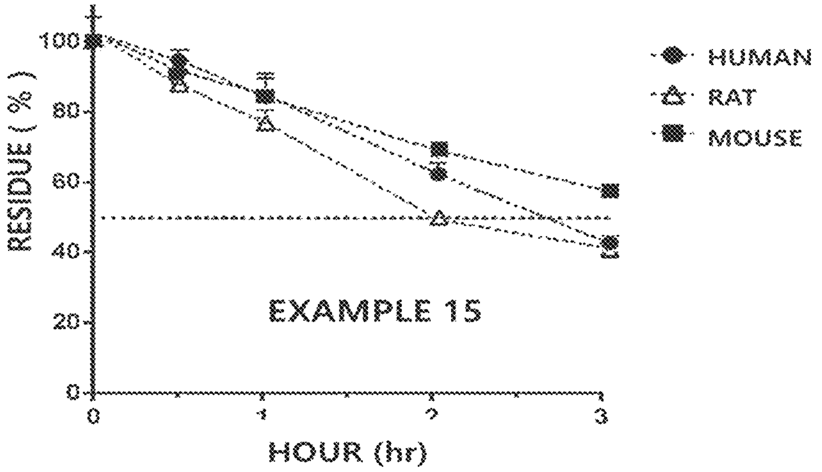
Figure 4A:
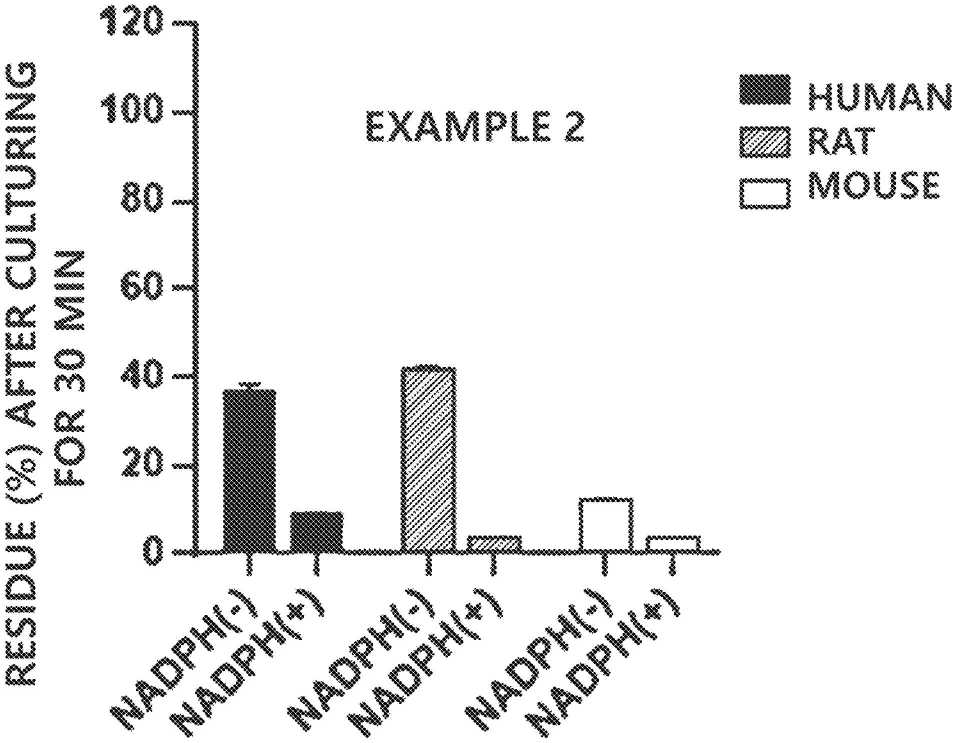
FIGS. 4A to 4E show metabolic stability test results in liver microtubules of the Example compounds according to the present invention.
Figure 4B:
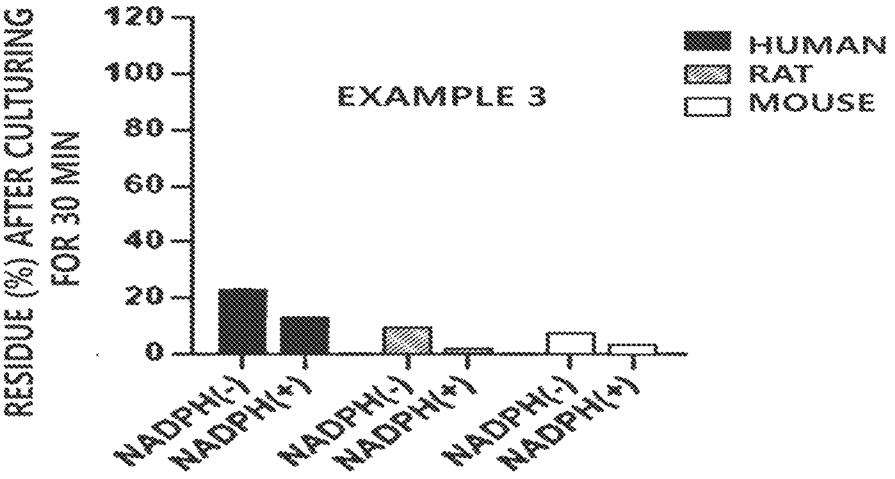
Figure 4C:
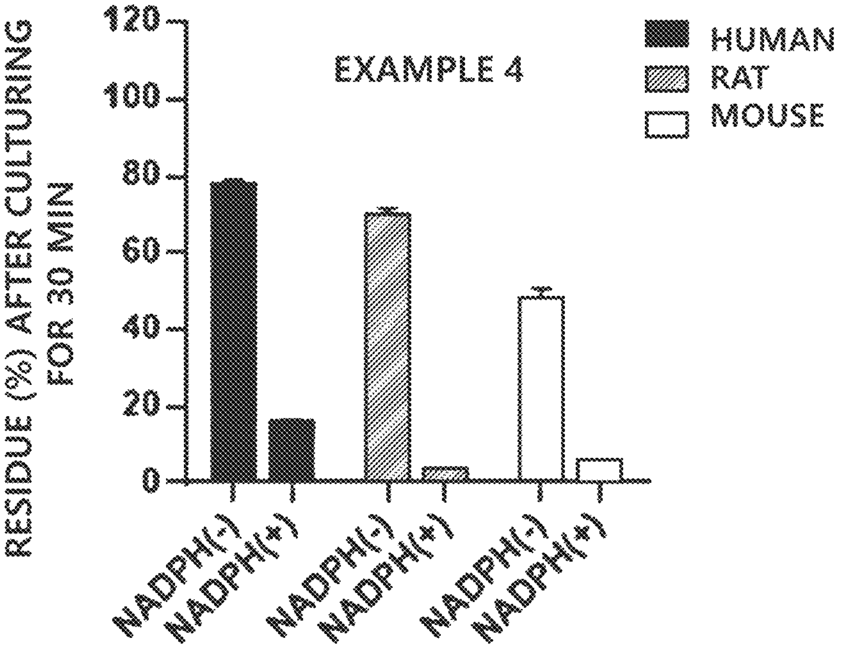
Figure 4D:
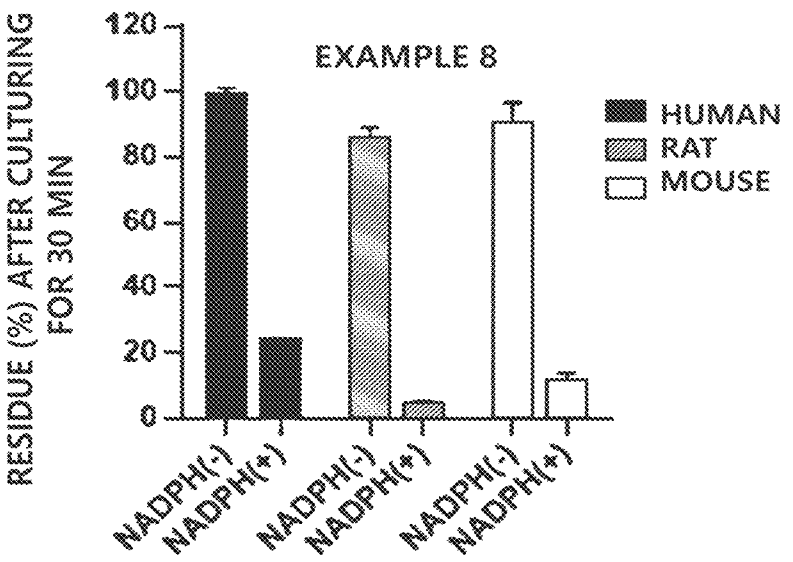
Figure 4E:
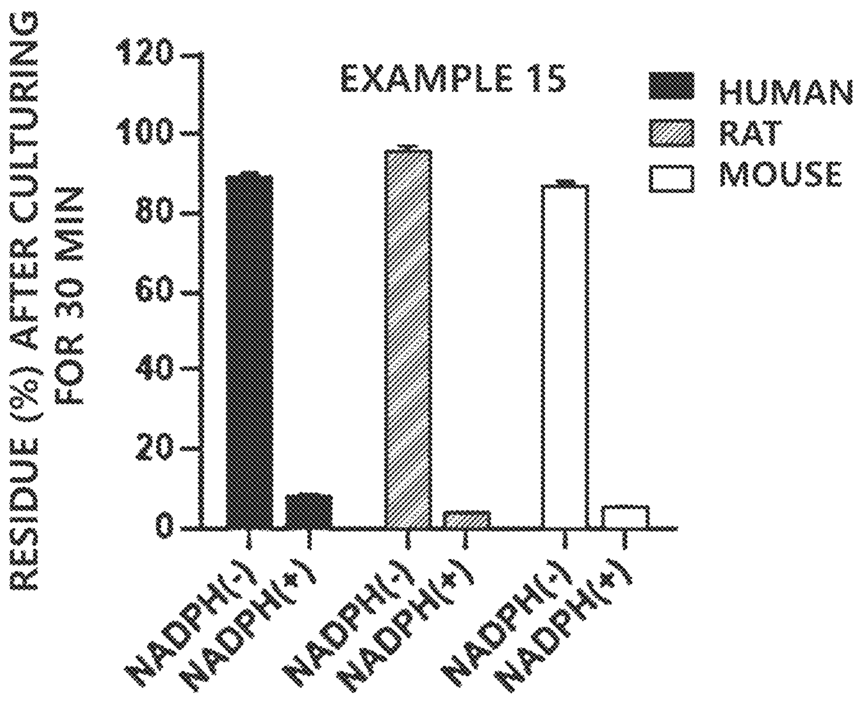

Compared with the solvent control group, reductions in tumor weight of 57.1%, 40.5%, and 26.2% ($p<0.001$) were observed, respectively, in the groups administered with the compounds of Examples 4, 8 and 15 (see FIGS. 2D and 2E).

Experimental Example 5: Stability Test in Plasma

In order to test the stability (in vivo) of the Example compounds according to the present invention, the compounds of Examples 2, 3, 4, 8 and 15 were administered intravenously, and plasma concentrations over time were observed. In addition, procaine was used as a positive control. Plasma stability was measured three times by administering the test compound at a concentration of 5 mM to human, rat, or mouse plasma (90 μL) at 37° C. Results thereof are shown in Table below and FIGS. 3A to 3E.

TABLE 6

| Compound | Plasma | Residue % (180 minutes elapsed) Mean | Standard deviation | $t_{1/2}$ (min) |
|---|---|---|---|---|
| Example 2 | Human | 90.43 | 3.23 | >180 |
| | Rat | 75.82 | 1.08 | >180 |
| | Mouse | 55.82 | 2.07 | >180 |
| Example 3 | Human | 56.52 | 5.22 | >180 |
| | Rat | 0.21 | 0.02 | 4.6 |
| | Mouse | 0.12 | 0.01 | 5.6 |
| Example 4 | Human | 49.41 | 0.39 | >180 |
| | Rat | 67.11 | 1.26 | >180 |
| | Mouse | 60.44 | 3.43 | >180 |
| Example 8 | Human | 26.05 | 0.81 | >180 |
| | Rat | 49.25 | 0.52 | >180 |
| | Mouse | 74.16 | 2.25 | >180 |
| Example 15 | Human | 4.20 | 1.69 | 159.9 |
| | Rat | 41.74 | 3.50 | 133.6 |
| | Mouse | 57.25 | 1.80 | >180 |
| Procaine | Human | 0.45 | 0.03 | |
| | Rat | 1.89 | 0.28 | |
| | Mouse | 1.06 | 0.05 | |

As shown in Table above and FIGS. 3A to 3E, the Example compounds had excellent stability in plasma.

Experimental Example 6: Metabolic Stability Test in Liver Microtubules

The test compounds at a concentration of 1 mi were administered in the presence or absence of NADPH (1 mM) to liver microtubules (0.5 mg protein/mL) of humans, rats and mice, and metabolic stability was tested at 37° C. for 30 minutes. In addition, buspirone was used as a positive control. Results thereof are shown in Table below and FIGS. 4A to 4E.

TABLE 7

| Liver microtubule | Cofactor | Residue (%) after culturing for 30 min Example 2 | Example 3 | Example 4 |
|---|---|---|---|---|
| Human | +NADPH | 8.69 ± 0.44 | 12.34 ± 0.69 | 15.76 ± 0.89 |
| | −NADPH | 36.40 ± 1.90 | 22.26 ± 0.72 | 77.60 ± 1.39 |
| Rat | +NADPH | 2.99 ± 0.64 | 1.39 ± 0.12 | 3.23 ± 0.55 |
| | −NADPH | 41.45 ± 0.93 | 8.53 ± 0.46 | 69.63 ± 1.94 |
| Mouse | +NADPH | 2.84 ± 0.34 | 2.50 ± 0.11 | 5.48 ± 0.04 |
| | −NADPH | 11.59 ± 1.06 | 6.81 ± 0.17 | 47.95 ± 2.93 |
| Buffer | | 77.94 ± 7.04 | 89.02 ± 4.39 | 100.93 ± 11.79 |

TABLE 8

| Liver microtubule | Cofactor | Residue (%) after culturing for 30 min Example 8 | Example 15 | Buspirone |
|---|---|---|---|---|
| Human | +NADPH | 24.11 ± 0.46 | 7.94 ± 0.74 | 2.21 ± 0.03 |
| | −NADPH | 99.18 ± 1.92 | 88.63 ± 1.61 | 91.06 ± 0.40 |
| Rat | +NADPH | 4.55 ± 0.94 | 3.47 ± 0.25 | 0.41 ± 0.02 |
| | −NADPH | 85.58 ± 3.34 | 94.95 ± 1.93 | 93.08 ± 1.21 |
| Mouse | +NADPH | 11.41 ± 2.47 | 4.82 ± 0.52 | 0.32 ± 0.05 |
| | −NADPH | 89.93 ± 6.72 | 86.31 ± 1.72 | 94.74 ± 0.74 |
| Buffer | | 98.98 ± 2.07 | 91.02 ± 2.89 | — |

As shown in Table and FIGS. 4A to 4E, it could be confirmed that the Example compounds had metabolic stability.

Experimental Example 7: Solubility Test

The Example compounds according to the present invention were tested in view of the solubility as follows.

The test substances were accurately weighed and placed in a glass vial. Then, solvent A was added in an amount corresponding to 20% of the desired final solution volume, and the mixture was completely dissolved by treatment with a vortexer and sonication. Next, solvent B in an amount corresponding to 10% or 20% of the final solution volume was added and mixed well. Solvent C in an amount corresponding to 80% of the final solution volume was added dropwise to the mixed solution and mixed. Finally, the mixture was subjected to sonication for 30 seconds. The mixed solution was prepared and used immediately before administration in the experiment.

Solvent A: Dimethylacetamide produced by SigmaAldrich

Solvent B: Cremophor EL produced by SigmaAldrich

Solvent C: 20% HPbCD ((2-Hydroxypropyl)-β-cyclodextrin produced by SigmaAldrich) in deionized water The solubility test conditions and solubility evaluation results are summarized in Table below.

TABLE 9

| Test compound | Animal species | Route of administration | Desired concentration (mg/kg) | Administration volume (mL/kg) | Administration concentration (mg/mL) | Sample amount (mg) | Solvent (mL) | Administration solvent (v/v %) | | Solubility evaluation result |
|---|---|---|---|---|---|---|---|---|---|---|
| Example 4 | Mouse | Peritoneal cavity | 20 | 10 | 2.0 | 2.00 | 1.000 | Solvent A | 20% | Soluble |
| | | | | | | | | Solvent B | 10% | |
| | | | | | | | | Solvent C | 70% | |
| Example 8 | Mouse | Peritoneal cavity | 20 | 10 | 2.0 | 2.00 | 1.000 | Solvent A | 20% | Soluble |
| | | | | | | | | Solvent B | 20% | |
| | | | | | | | | Solvent C | 60% | |
| Example 15 | Mouse | Peritoneal cavity | 20 | 10 | 2.0 | 2.00 | 1.000 | Solvent A | 20% | Soluble |
| | | | | | | | | Solvent B | 20% | |
| | | | | | | | | Solvent C | 60% | |

Experimental Example 8: Pharmacokinetic (PK) Test

Pharmacokinetic (PK) parameters of the Example compounds according to the present invention were determined using male ICR mice as follows (n=3).

Pharmacokinetic (PK) parameters were measured by non-compartmental analysis of plasma concentration-time curves using Kinetica™ 4.4.1 (Thermo Fisher Scientific, USA). Results thereof are shown in Table below and FIGS. 5A to 5C. In Table below, "F" parameter was calculated using $AUC_{last}$, "N/A" indicates the phrase not applicable, and "NC" indicates the phrase not calculated.

TABLE 10

| | | Example 4 | | | |
|---|---|---|---|---|---|
| | | Intravenous administration, 5 mg/kg | | Oral administration, 20 mg/kg | |
| Compound Parameters | | Mean | Standard deviation | Mean | Standard deviation |
| $t_{max}$ | hr | N/A | | 0.25 | 0.00 |
| $C_{max}$ | ng/mL | N/A | | 431.00 | 19.29 |
| $AUC_{last}$ | ng*hr/mL | 1479.17 | 120.24 | 284.79 | 44.10 |
| $AUC_{inf}$ | ng*hr/mL | 1502.35 | 112.33 | 295.27 | 51.8 |
| CL | L/hr/kg | 3.34 | 0.25 | 69.14 | 12.1 |
| $V_{ss}$ | L/kg | 0.98 | 0.24 | N/A | |
| $V_z$ | L/kg | 1.88 | 0.58 | N/A | |
| $t_{1/2}$ | hr | 0.39 | 0.10 | 0.4 | 0.1 |
| $MRT_{inf}$ | hr | 0.29 | 0.07 | 0.7 | 0.1 |
| F | % | N/A | | 4.8 | 0.75 |

TABLE 11

| | | Example 8 | | | |
|---|---|---|---|---|---|
| | | Intravenous administration, 5 mg/kg | | Oral administration, 20 mg/kg | |
| Compound Parameters | | Mean | Standard deviation | Mean | Standard deviation |
| $t_{max}$ | hr | N/A | | 0.58 | 0.14 |
| $C_{max}$ | ng/mL | N/A | | 93.87 | 5.19 |
| $AUC_{last}$ | ng*hr/mL | 2377.94 | 112.06 | 96.27 | 9.58 |
| $AUC_{inf}$ | ng*hr/mL | 2386.74 | 112.22 | 102.54 | 8.2 |
| CL | L/hr/kg | 2.10 | 0.10 | 195.92 | 16.1 |
| $V_{ss}$ | L/kg | 0.50 | 0.03 | N/A | |
| $V_z$ | L/kg | 0.85 | 0.05 | N/A | |
| $t_{1/2}$ | hr | 0.28 | 0.01 | 0.4 | 0.0 |
| $MRT_{inf}$ | hr | 0.24 | 0.00 | 0.9 | 0.1 |
| F | % | N/A | | 1.0 | 0.10 |

TABLE 12

| | | Example 15 | | | |
|---|---|---|---|---|---|
| | | IV, 5 mg/kg | | PO, 20 mg/kg | |
| Compound Parameters | | Mean | Standard deviation | Mean | Standard deviation |
| $t_{max}$ | hr | N/A | | 0.25 | 0.00 |
| $C_{max}$ | ng/mL | N/A | | 34.43 | 27.34 |
| $AUC_{last}$ | ng*hr/mL | 1717.55 | 41.34 | 18.00 | 18.40 |
| $AUC_{inf}$ | ng*hr/mL | 1729.14 | 41.24 | NC | NC |
| CL | L/hr/kg | 2.89 | 0.07 | NC | NC |
| $V_{ss}$ | L/kg | 0.71 | 0.02 | N/A | |
| $v_z$ | L/kg | 1.37 | 0.09 | N/A | |

TABLE 12-continued

| | | Example 15 | | | |
|---|---|---|---|---|---|
| | | IV, 5 mg/kg | | PO, 20 mg/kg | |
| Compound Parameters | | Mean | Standard deviation | Mean | Standard deviation |
| $t_{1/2}$ | hr | 0.33 | 0.02 | NC | NC |
| $MRT_{inf}$ | hr | 0.24 | 0.01 | NC | NC |
| F | % | N/A | | 0.3 | 0.27 |

Figure 5A:
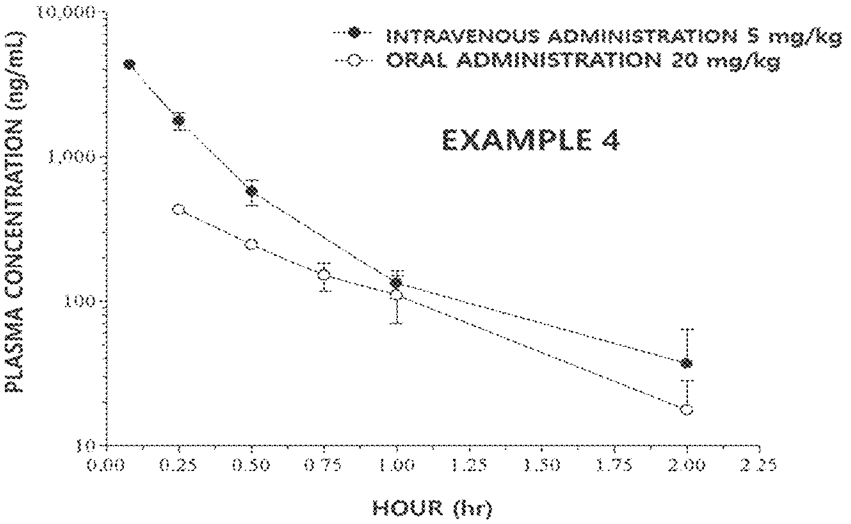
FIGS. 5A to 5C show pharmacokinetic (PK) test results of the Example compounds according to the present invention.
Figure 5B:
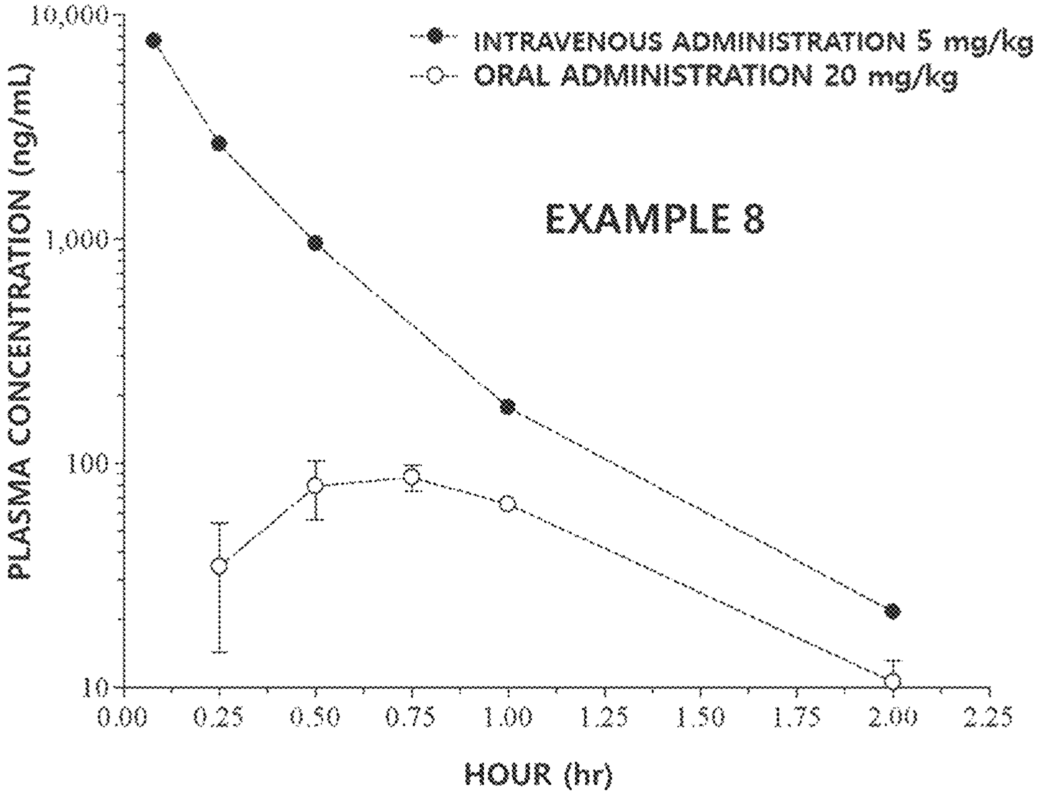
Figure 5C:
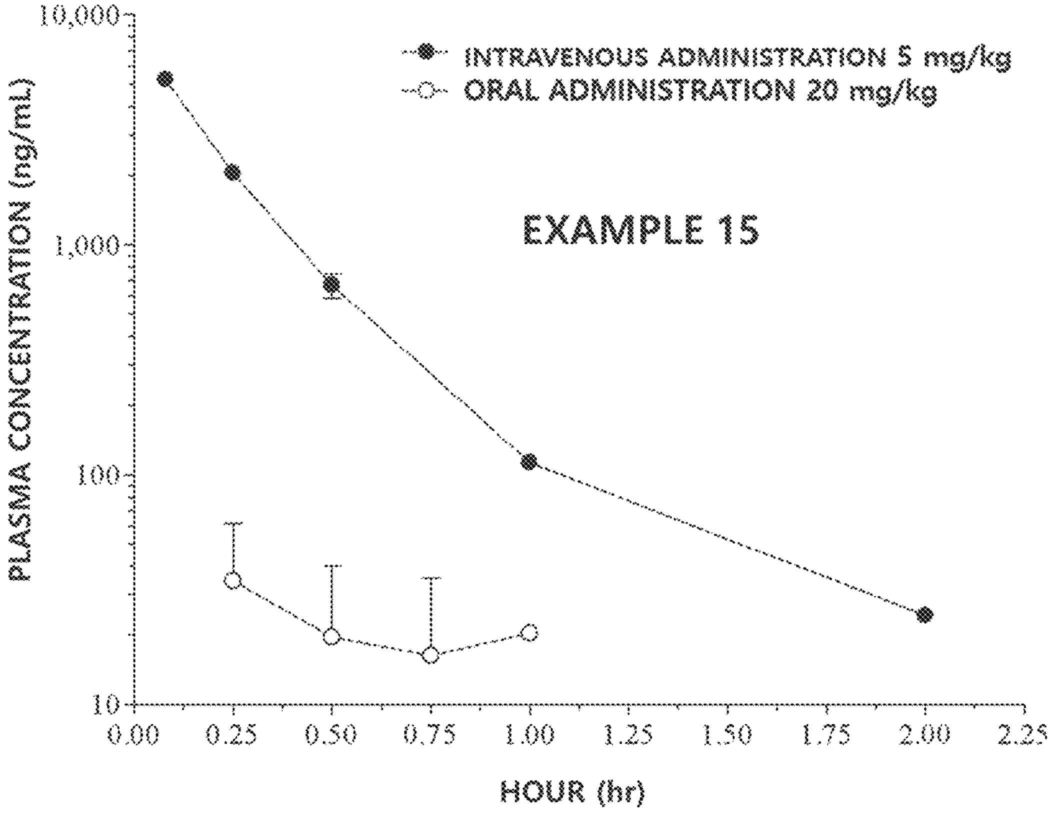

As shown in Table above and FIGS. 5A to 5C, it could be confirmed that the Example compounds had stability that could be used as drugs.

Experimental Example 9: Confirmation of Inhibitory Effect on Cancer Metastasis a. Wound Healing Assay HeLa CCL2 cells were cultured in 6 wells at 100%, wounded with a yellow tip, and treated with 50 nM and 100 nM of the compound of Example 4. In order to observe the effect of the drug, the degree of cell migration was compared and observed by recording the state of the cells before treatment as images, and comparing the cell state before drug treatment with the state of the cells at 24, 36, and 48 hours post the drug treatment. The concentration of the compound of Example 4 treated with the cells was determined by performing MTT assay.

Figure 6A:
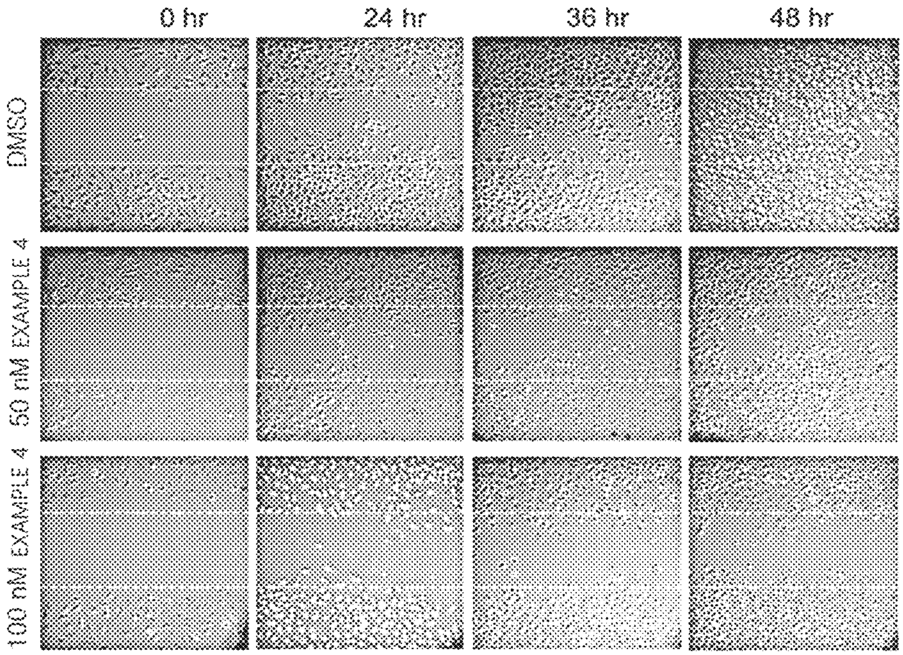
FIGS. 6A and 6B show wound healing assay results of the Example compounds according to the present invention.
Figure 6B:
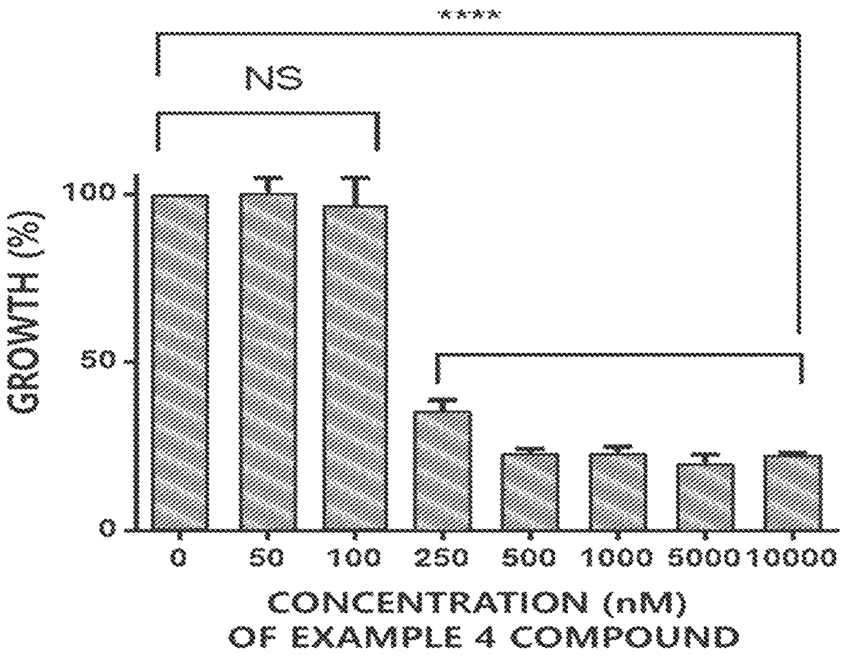

As a result, as shown in FIGS. 6A and 6B, the concentration of the compound of Example 4 up to 100 nM did not have a significant effect on cell growth.

b. In Vitro Invasion Assay

In addition, in order to confirm the efficacy of inhibiting cell migration again, an invasion assay was performed. A trans well chamber for a 24-well plate was prepared, and HeLa CCL2 cells at a density of $5\times10^4$ were put into the upper chamber, treated with 10 nM, 50 nM, 100 nM, and 250 nM of the compound of Example 4, and cultured. Then, after 16 hours, the migrated cells were identified and the number thereof was measured through cell staining.

Figure 7A:
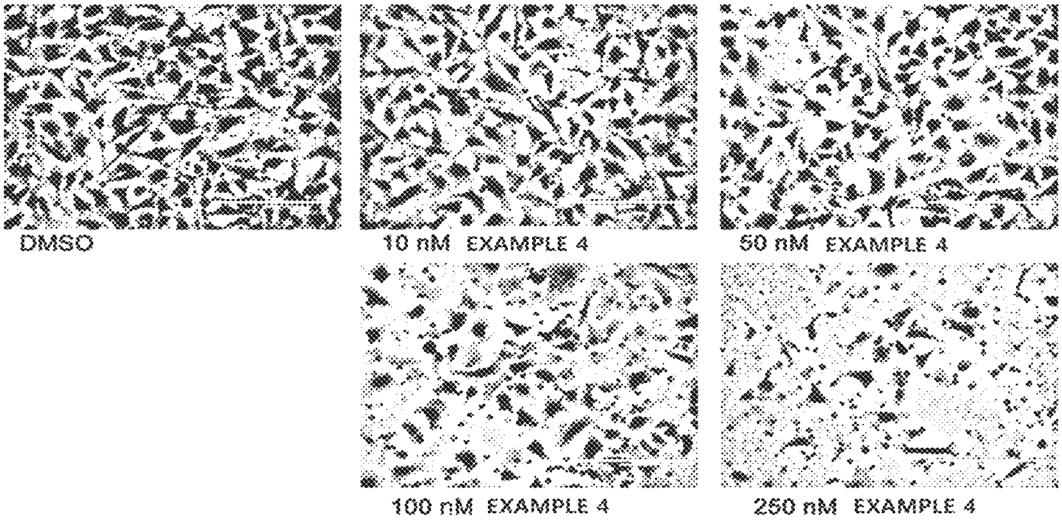
FIGS. 7A and 7B show in vitro invasion assay results of the Example compounds according to the present invention.
Figure 7B:
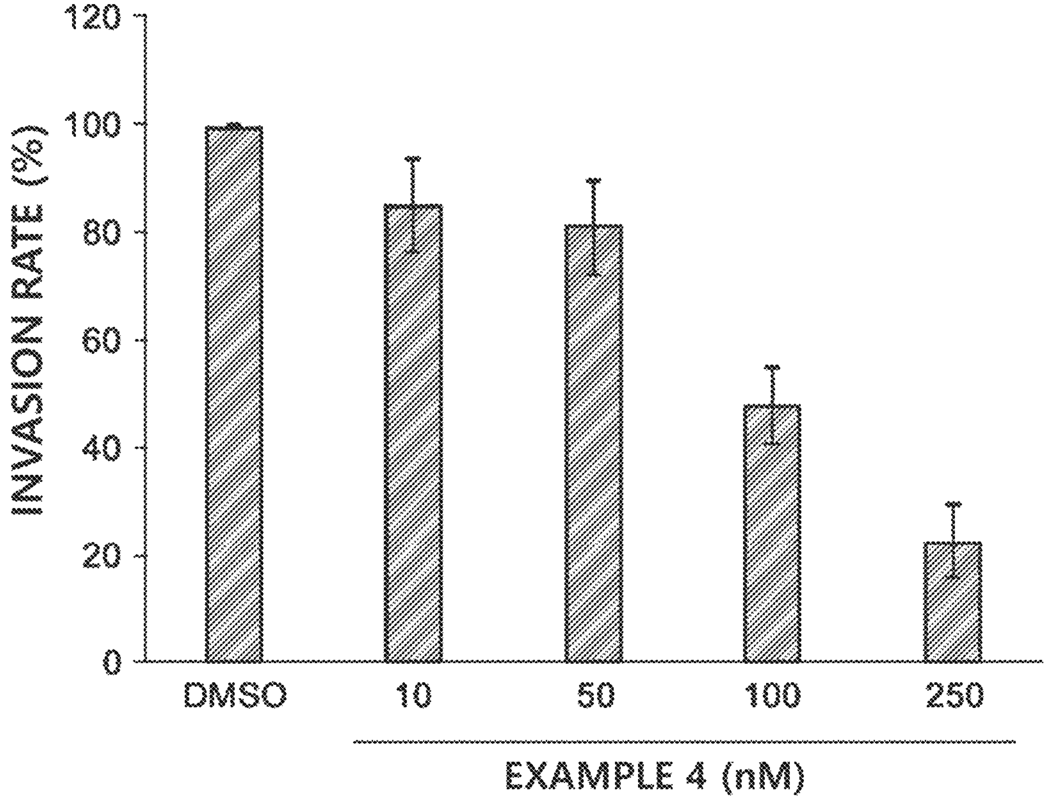

As a result, as shown in FIGS. 7A and 7B, it could be confirmed that the compound of Example 4 according to the present invention had an excellent cancer metastasis inhibitory effect.

Experimental Example 10: Toxicity Evaluation 10.1 Materials and Experimental Procedures a. Mouse All animal experiments and procedures were performed in accordance with ethical standards under the approval of the Institutional Animal Care and Use Committee (IACUC) of the Korea Research Institute of Bioscience and Biotechnology (KRIBB). ICR mice were supplied by Daehan Biolink Co., Ltd (Korea). All mice were housed in sterile animal isolation facilities. All in vivo experiments were performed using 6-8 week old mice.

b. Mouse Toxicity Test

Acute toxicity test of the compound of Example 4 was performed at the Laboratory Animal Resource Center of the Korea Research Institute of Bioscience and Biotechnology. ICR mice (6-8 weeks old) were acclimatized for up to 10 days before the experiment, and then 3 mice were injected with the drugs. The Example compound was mixed with a solvent and injected intraperitoneally, and after drug treatment, clinical symptoms were observed twice within 24 hours, and additional drug treatment was performed up to 10 times as scheduled. The mice were weighed 5 times as scheduled.

c. Open Field Experiment

The experimental apparatus was constructed similarly to that used in the paper described by Reyes-Mendez et al. (2018), and was composed of a black acrylic fence (floor area of 30×30 cm and wall height of 40 cm). The floor surface was divided into 25 squares each having a size of 10×10 cm. For this experiment, mice were placed on the center of the floor and spontaneous activities thereof were recorded for 7 minutes from the top. After the experiment, the experimental apparatus was thoroughly washed with 30% ethanol. Three observers, unaware whether the drug was treated or not, analyzed the first 5 minutes of recorded video to count the number of squares the mouse passed, and add up the time during which the mouse stayed without moving, and the number of times the mouse was groomed or shaken, and the like. Based on the contents analyzed above, the time during which the mouse stayed in the central zone, speed, and total moving distance were calculated. A case where the two-tailed probability value was less than 0.05 ($p<0.05$) was considered statistically significant.

Figure 8A:
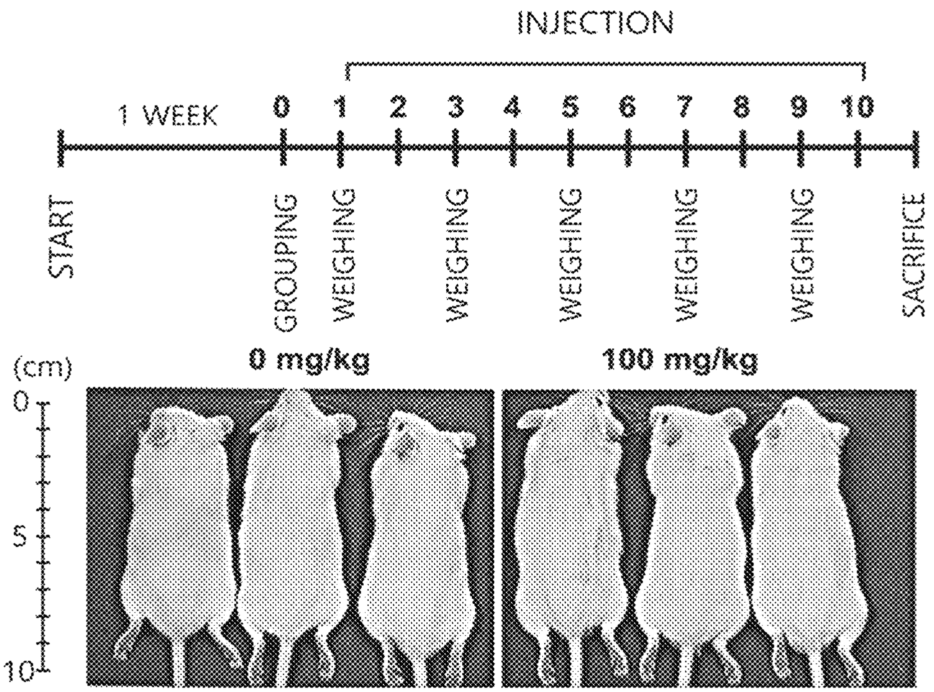
Figure 8B:
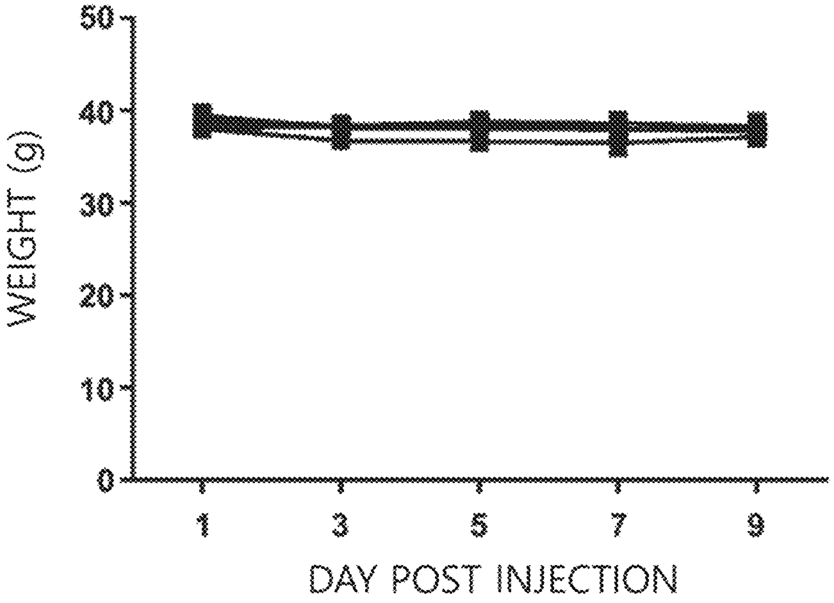

10.2 Results a. Solubility and Toxicity Clinical Evaluation of Example Compound 100 mg/kg of the compound of Example 4 was dissolved in a solvent (N',N'-dimethylacetamide/Kolliphor/2-hydroxypropyl-β-cyclodextrin (10% concentration of distilled water solution)=40:10:50). When the concentration became thicker than that, the reaction solution immediately precipitated. The solution in which the compound of Example 4 was dissolved from 12.5 mg/kg to 100 mg/kg was injected into the peritoneal cavity of mice 10 times a day in a volume of 100 μL (see FIG. 8A). All animals survived to the final day, and no particular problems were seen by visual observation (see Table 13 and FIG. 8A). As a result of weight measurement, no specific effect was observed even when the compound of Example 4 was administered as scheduled (see FIG. 8B).

In addition, as a result of dissecting the mouse and confirming the presence or absence of changes in each organ, there was no change in the size and morphology of each organ, which could be confirmed that the compound of Example 4 did not induce serious toxicity even when administered intraperitoneally 10 times at a concentration of 100 mg/kg.

b. Toxicity Evaluation of Example Compounds Through Animal Behavioral Analysis

Figure 8C:
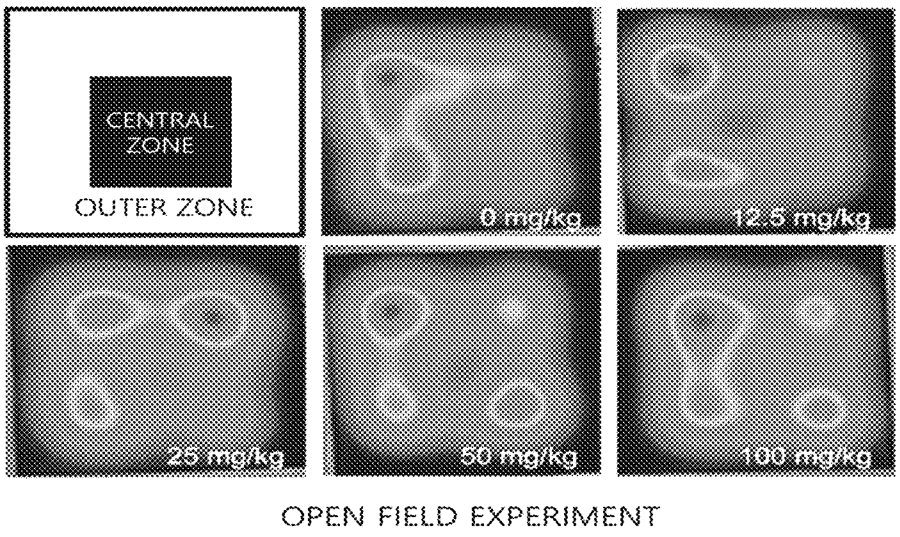
Figure 8D:
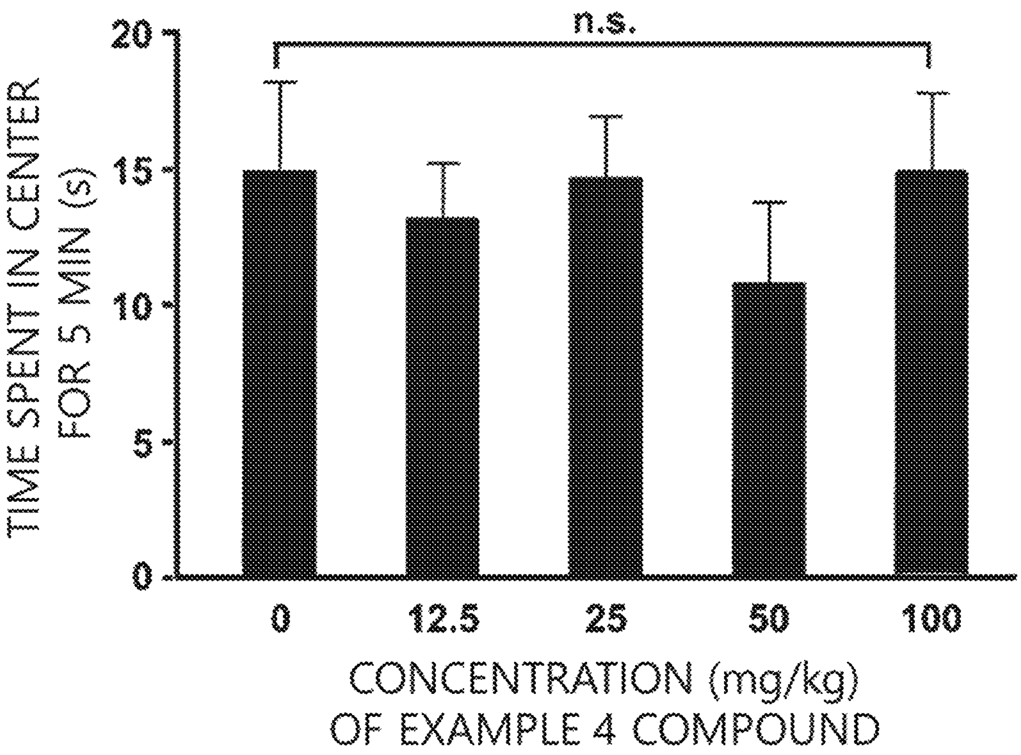
Figure 8E:
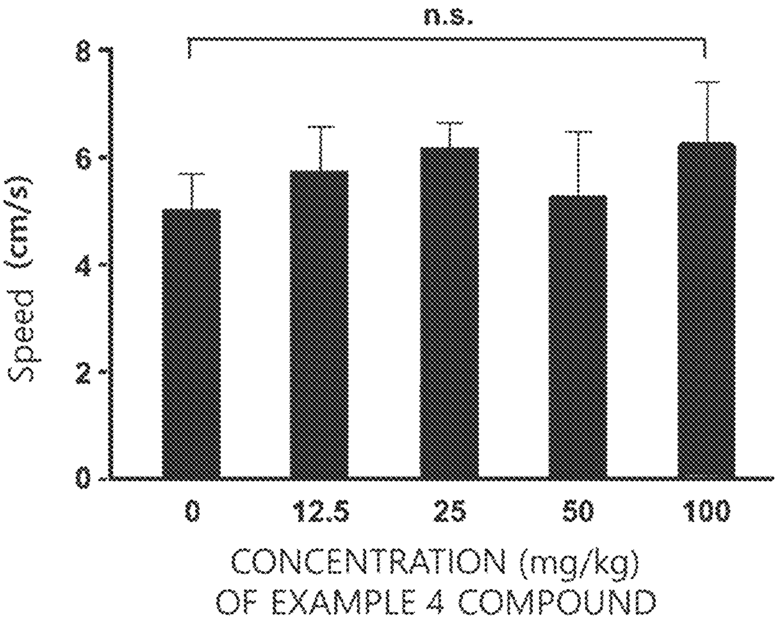
Figure 8F:
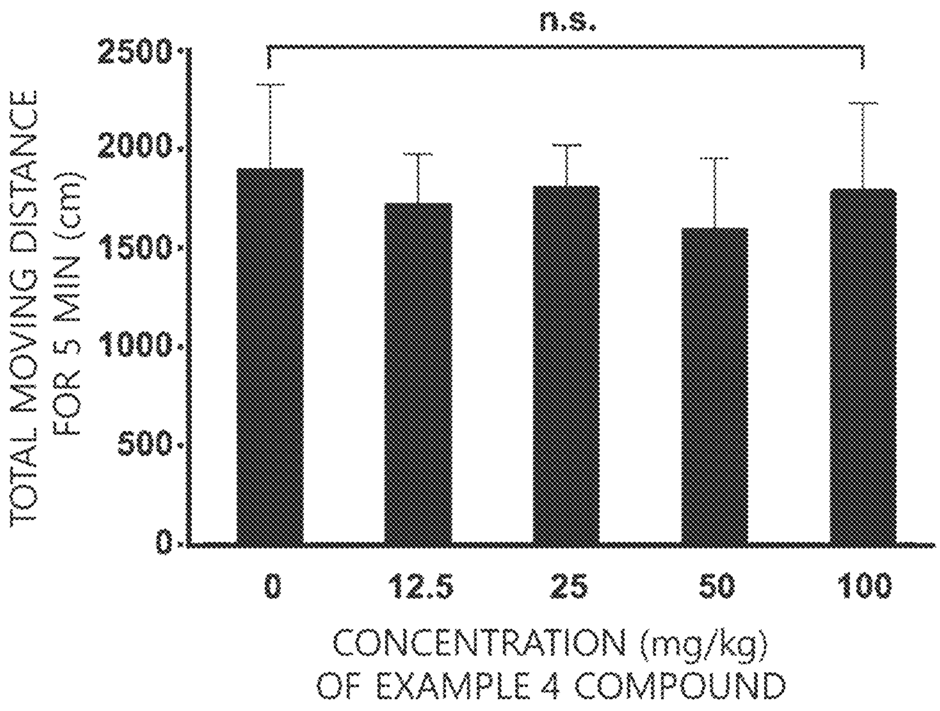

No statistically significant experimental groups were found as results of open-field experiments in mice. As a result of measuring the time during which the mouse stayed in the central zone of the open field (see FIGS. 8C and 8D), the 50 mg/kg test group among the 0-100 mg/kg test group showed a slight decrease in the time during which the mouse stayed in the central zone, but this decrease was not statistically significant (see FIG. 8D).

These results showed that the compound of Example 4 did not affect the behavior of mice in all groups. The fact that there is no significant change between the drug treatment experimental group and the control group as described above is evidence that the compound of Example 4 has no neurological effect on animals.

TABLE 13

| Treatment group (mg/kg, n = 3, i.p.) | Appearance and condition | Behavioral evaluation | Posture | Skin and fur | Survival rate (%) |
|---|---|---|---|---|---|
| 0 mg/kg | Normal | Normal | No change | No change | 100 |
| 12.5 mg/kg | Normal | Normal | No change | No change | 100 |
| 25 mg/kg | Normal | Normal | No change | No change | 100 |
| 50 mg/kg | Normal | Normal | No change | No change | 100 |
| 100 mg/kg | Normal | Normal | No change | No change | 100 |

What is claimed is:

1. A compound of Formula 1:

Formula 1

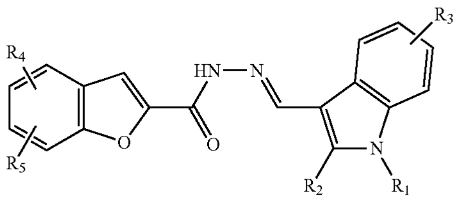

wherein, $R_1$ is H, $C_{1-6}$alkyl, $C_{1-6}$alkoxycarbonyl$C_{1-3}$alkyl, or $C_{1-6}$alkoxy$C_{1-3}$alkyl;

$R_2$ is halogen;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$alkylcarbonylamino, provided that $R_4$ and $R_5$ are not H at the same time, or a stereoisomer or a pharmaceutically acceptable salt thereof.

2. The compound of claim 1, wherein $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$.

3. The compound of claim 1, wherein $R_2$ is Cl, or Br.

4. The compound of claim 1, wherein $R_3$ is H, F, Cl, $—CH_3$, $—OCH_3$, or $—OCF_3$.

5. The compound of claim 1, wherein $R_4$ and $R_5$ are each independently H, Cl, $—CH_3$, $—OCH_3$, or $—NHCOCH_3$, provided that $R_4$ and $R_5$ are not H at the same time.

6. The compound of claim 1, wherein $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$;

$R_2$ is Cl, or Br;

$R_3$ is H, F, Cl, $—CH_3$, $—OCH_3$, or $—OCF_3$; and $R_4$ and $R_5$ are each independently H, Cl, $—CH_3$, $—OCH_3$, or $—NHCOCH_3$, provided that $R_4$ and $R_5$ are not H at the same time.

7. The compound of claim 1, wherein the compound is selected from the group consisting of the following compounds:

(E)-N'-[(2-chloro-1H-indol-3-yl)methylene]-5-methylbenzofuran-2-carbohydrazide;

(E)-N'-[(2-chloro-1-methyl-H-indol-3-yl)methylene]-5-methylbenzofuran-2-carbohydrazide;

Ethyl (E)-2-{2-chloro-3-[(2-(5-methylbenzofuran-2-carbonyl)hydrazinylidene)methyl]-1H-indol-1-yl}acetate;

(E)-N'-[2-chloro-1-(2-ethoxyethyl)-1H-indol-3-yl]methylene-5-methylbenzofuran-2-carbohydrazide;

(E)-N'-[2-bromo-1-(2-ethoxyethyl)-1H-indol-3-yl]methylene-5-methylbenzofuran-2-carbohydrazide;

(E)-N'-[2-chloro-1-(2-methoxyethyl)-1H-indol-3-yl]methylene-5-methylbenzofuran-2-carbohydrazide;

(E)-N'-[2-chloro-1-(2-ethoxyethyl)-5-methoxy-1H-indol-3-yl]methylene-5-methylbenzofuran-2-carbohydrazide;

(E)-N'-[2-chloro-1-(2-ethoxyethyl)-6-methoxy-1H-indol-3-yl]methylene-5-methylbenzofuran-2-carbohydrazide;

(E)-N'-[2-chloro-1-(2-ethoxyethyl)-5-fluoro-1H-indol-3-yl]methylene-5-methylbenzofuran-2-carbohydrazide;

(E)-N'-{[2,5-dichloro-1-(2-ethoxyethyl)-1H-indol-3-yl]methylene}-5-methylbenzofuran-2-carbohydrazide;

(E)-N'-{[2-chloro-1-(2-ethoxyethyl)-5-(trifluoromethoxy)-1H-indol-3-yl]methylene}-5-methylbenzofuran-2-carbohydrazide;

(E)-N'-[2-chloro-1-(2-ethoxyethyl)-5-methyl-1H-indol-3-yl]methylene-5-methylbenzofuran-2-carbohydrazide;

(E)-N'-[2-chloro-1-(2-ethoxyethyl)-1H-indol-3-yl]methylene-5-methoxybenzofuran-2-carbohydrazide;

(E)-N'-[2-chloro-1-(2-ethoxyethyl)-5-methoxy-1H-indol-3-yl]methylene-5-methoybenzofuran-2-carbohydrazide;

(E)-5-chloro-N'-{[2-chloro-1-(2-ethoxyethyl)-1H-indol-3-yl]methylene}benzofuran-2-carbohydrazide;

(E)-N'-{[2-chloro-1-(2-ethoxyethyl)-1H-indol-3-yl]methylene}-4,7-dimethylbenzofuran-2-carbohydrazide;

(E)-N'-[2-chloro-1-(2-ethoxyethyl)-1H-indol-3-yl]methylene-4,6-dimethoxybenzofuran-2-carbohydrazide; and (E)-N'-{2-[2-((2-chloro-1-(2-ethoxyethyl)-1H-indol-3-yl)methylene]hydrazine-1-carbonyl}benzofuran-5-yl)acetamide.

8. A pharmaceutical composition comprising the compound of claim 1 and a pharmaceutically acceptable additive.

9. A method for treating a cell proliferative disease, comprising administering to a subject in need thereof a compound of Formula 1:

Formula 1

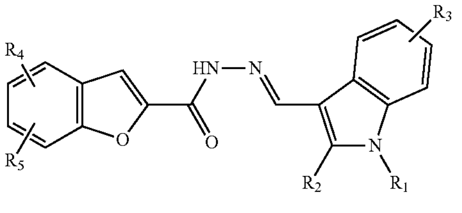

wherein, $R_1$ is H, $C_{1-6}$alkyl, $C_{1-6}$alkoxycarbonyl$C_{1-3}$alkyl, or $C_{1-6}$alkoxy$C_{1-3}$alkyl;

$R_2$ is halogen;

$R_3$ is H, halogen, $C_{1-6}$alkyl, $C_{1-6}$alkoxy, or halo$C_{1-6}$alkoxy; and $R_4$ and $R_5$ are each independently H, halogen, $C_{1-6}$alkyl, $C_{1-6}$alkoxy, or $C_{1-6}$alkylcarbonylamino, provided that $R_4$ and $R_5$ are not H at the same time, or a stereoisomer or a pharmaceutically acceptable salt thereof.

10. The method of claim 9, wherein the cell proliferative disease is cancer.

11. The method of claim 10, wherein the cancer is a solid cancer, a hematologic cancer, or a metastatic cancer.

12. The method of claim 10, wherein the cancer is rectal cancer, breast cancer, lung cancer, stomach cancer, liver cancer, leukemia, glioma, skin cancer, cervical cancer, or metastases derived therefrom.

13. The method of claim 9, wherein the compound inhibits the polymerization of tubulin in microtubules.

14. The method of claim 9, wherein $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$.

15. The method of claim 9, wherein $R_2$ is Cl or Br.

16. The method of claim 9, wherein $R_3$ is H, F, Cl, $—CH_3$, $—OCH_3$, or $—OCF_3$.

17. The method of claim 9, wherein $R_4$ and $R_5$ are each independently H, Cl, $—CH_3$, $—OCH_3$, or $—NHCOCH_3$, provided that $R_4$ and $R_5$ are not H at the same time.

18. The method of claim 9, wherein $R_1$ is H, $—CH_3$, $—CH_2CO_2CH_2CH_3$, $—CH_2OCH_2CH_3$, $—CH_2CH_2OCH_2CH_3$ or $—CH_2CH_2OCH_3$;

$R_2$ is Cl or Br;

$R_3$ is H, F, Cl, $—CH_3$, $—OCH_3$, or $—OCF_3$; and $R_4$ and $R_5$ are each independently H, Cl, $—CH_3$, $—OCH_3$, or $—NHCOCH_3$, provided that $R_4$ and $R_5$ are not H at the same time.

19. The method of claim 9, wherein the compound is selected from the group consisting of the following compounds:

(E)-N'-[(2-chloro-1H-indol-3-yl)methylene]-5-methylbenzofuran-2-carbohydrazide;

(E)-N'-[(2-chloro-1-methyl-1H-indol-3-yl)methylene]-5-methylbenzofuran-2-carbohydrazide;

Ethyl (E)-2-{2-chloro-3-[(2-(5-methylbenzofuran-2-carbonyl)hydrazinylidene)methyl]-1H-indol-1-yl}acetate;

(E)-N'-[2-chloro-1-(2-ethoxyethyl)-1H-indol-3-yl]methylene-5-methylbenzofuran-2-carbohydrazide;

(E)-N'-[2-bromo-1-(2-ethoxyethyl)-1H-indol-3-yl]methylene-5-methylbenzofuran-2-carbohydrazide;

(E)-N'-[2-chloro-1-(2-methoxyethyl)-1H-indol-3-yl]methylene-5-methylbenzofuran-2-carbohydrazide;

(E)-N'-[2-chloro-1-(2-ethoxyethyl)-5-methoxy-1H-indol-3-yl]methylene-5-methylbenzofuran-2-carbohydrazide;

(E)-N'-[2-chloro-1-(2-ethoxyethyl)-6-methoxy-1H-indol-3-yl]methylene-5-methylbenzofuran-2-carbohydrazide;

(E)-N'-[2-chloro-1-(2-ethoxyethyl)-5-fluoro-1H-indol-3-yl]methylene-5-methylbenzofuran-2-carbohydrazide;

(E)-N'-{[2,5-dichloro-1-(2-ethoxyethyl)-1H-indol-3-yl]methylene}-5-methylbenzofuran-2-carbohydrazide;

(E)-N'-{[2-chloro-1-(2-ethoxyethyl)-5-(trifluoromethoxy)-1H-indol-3-yl]methylene}-5-methylbenzofuran-2-carbohydrazide;

(E)-N'-[2-chloro-1-(2-ethoxyethyl)-5-methyl-1H-indol-3-yl]methylene-5-methylbenzofuran-2-carbohydrazide;

(E)-N'-[2-chloro-1-(2-ethoxyethyl)-1H-indol-3-yl]methylene-5-methoxybenzofuran-2-carbohydrazide;

(E)-N'-[2-chloro-1-(2-ethoxyethyl)-5-methoxy-1H-indol-3-yl]methylene-5-methoybenzofuran-2-carbohydrazide;

(E)-5-chloro-N'-{[2-chloro-1-(2-ethoxyethyl)-1H-indol-3-yl]methylene}benzofuran-2-carbohydrazide;

(E)-N'-{[2-chloro-1-(2-ethoxyethyl)-1H-indol-3-yl]methylene}-4,7-dimethylbenzofuran-2-carbohydrazide;

(E)-N'-[2-chloro-1-(2-ethoxyethyl)-1H-indol-3-yl]methylene-4,6-dimethoxybenzofuran-2-carbohydrazide; and (E)-N'-{2-[2-((2-chloro-1-(2-ethoxyethyl)-1H-indol-3-yl)methylene]hydrazine-1-carbonyl}benzofuran-5-yl)acetamide.

* * * * *